United States Patent
Boggs et al.

(10) Patent No.: US 7,319,109 B2
(45) Date of Patent: Jan. 15, 2008

(54) FARNESOID X RECEPTOR AGONISTS

(75) Inventors: Sharon D Boggs, Durham, NC (US);
Jon L Collins, Durham, NC (US);
Stephen M Hyatt, Durham, NC (US);
Patrick R Maloney, Durham, NC (US)

(73) Assignee: Smith Kline Beecham Corporation, Philadelphia, PA (US)

( * ) Notice: Subject to any disclaimer, the term of this patent is extended or adjusted under 35 U.S.C. 154(b) by 227 days.

(21) Appl. No.: 10/535,228

(22) PCT Filed: Nov. 12, 2003

(86) PCT No.: PCT/US03/35808

§ 371 (c)(1),
(2), (4) Date: May 17, 2005

(87) PCT Pub. No.: WO2004/048349

PCT Pub. Date: Jun. 10, 2004

(65) Prior Publication Data

US 2006/0258725 A1    Nov. 16, 2006

Related U.S. Application Data

(60) Provisional application No. 60/428,374, filed on Nov. 22, 2002.

(51) Int. Cl.
*C07D 261/06* (2006.01)
*A61K 31/42* (2006.01)
*A61K 31/422* (2006.01)

(52) U.S. Cl. ....... 514/378; 548/247
(58) Field of Classification Search ........ 548/247, 548/126, 127
See application file for complete search history.

(56) References Cited

U.S. PATENT DOCUMENTS

| | | | |
|---|---|---|---|
| 6,187,797 B1 | 2/2001 | Pruitt et al. | |
| 6,187,814 B1 | 2/2001 | Elias et al. | |

FOREIGN PATENT DOCUMENTS

| | | | |
|---|---|---|---|
| EP | 312867 A1 | 4/1989 | |
| GB | 2293360 A | 3/1996 | |
| JP | 11263775 A | * 9/1999 | |
| WO | WO-98/57951 A | 12/1998 | |
| WO | WO 00/37077 | 6/2000 | |
| WO | WO-00/59902 A | 10/2000 | |
| WO | WO-00/64876 A | 11/2000 | |
| WO | WO-01/19778 A1 | 3/2001 | |
| WO | WO-01/25210 A2 | 4/2001 | |
| WO | WO 03/015771 | 2/2003 | |

OTHER PUBLICATIONS

Schulman et al. Chemistry & Biology 2004, 11, 639-646.*
Bishop-Bailey et al. PNAS 2004, 101(10), 3668-3673.*
Caron et al. Endocrinology 2006, 147(9), 4022-4024.*
Claudel et al. Arteriosclerosis, Thrombosis, and Vascular Biology 2005, 25, 2020-2030.*
BM Forman. et al; Identification of a nuclear receptor that is activated by farnesol metabolites; Cell; 1995; 81; 687-693.
DJ Mangelsdorf, et al.; The RXR heterodimers and orphan receptors; Cell; 1995; 83: 841-850.
DW Russell, et al.; Nuclear Orphan Receptors Control Cholesterol Catabolism; Cell; 1999; 97; 539-542.
Hofmann, AF; The Continuing Importance of Bile Acids in Liver and Intestinal Disease; Arch Intern Med; 1999; 159; 2647-2658.
Maloney, P. et al.; Identification of a Chemical Tool for the Orphan Nuclear Receptor FXR; J Med Chem; 2000; 43/16; 2971-2974.
Neuberger J; Primary Billary Cirrhosis; Lancet: 1997: 350; 875-879.
Sinal, et al.; Targeted Disruption of the Nuclear Receptor FXR/BAR Impairs Bile Acid and Lipid Homeostasis; Cell; 2000; 102/6; 731-744.
W Seol, et al.; Isolation of proteins that interact specifically with the retinoid X receptor, two novel orphan receptors; Mol Endocrinol; 1995; 9; 72-85.

* cited by examiner

*Primary Examiner*—Rebecca Anderson
*Assistant Examiner*—Jason M Nolan
(74) *Attorney, Agent, or Firm*—Alice P. Bradney

(57) ABSTRACT

The invention relates to a compound of formula (I):

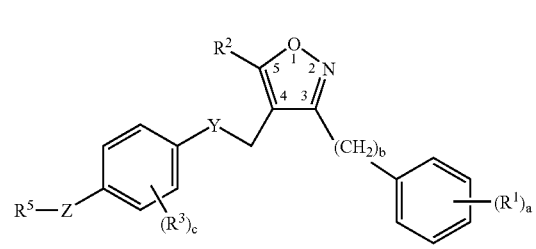

wherein all variables are as defined herein and to pharmaceutical compositions, methods of using, and processes for preparing the same.

23 Claims, No Drawings

FARNESOID X RECEPTOR AGONISTS

CROSS REFERENCES TO RELATED APPLICATIONS

This application is a 371 Application of PCT/US2003/035808, filed 12 Nov. 2003, which claims priority to U.S. application Ser. No. 60/428,374, filed 22 Nov. 2002.

BACKGROUND OF THE INVENTION

The present invention relates to Farnesoid X receptors (FXR). More particularly, the present invention relates to compounds useful as agonists for FXR, pharmaceutical formulations comprising such compounds, and therapeutic use of the same.

FXR is an orphan nuclear receptor initially identified from a rat liver cDNA library (B M. Forman, et al., Cell 81:687-693 (1995)) that is most closely related to the insect ecdysone receptor. FXR is a member of the nuclear receptor family of ligand-activated transcription factors that includes receptors for the steroid, retinoid, and thyroid hormones (D J. Mangelsdorf, et al., Cell 83:841-850 (1995)). Northern and in situ analysis show that FXR is most abundantly expressed in the liver, intestine, kidney, and adrenal (B M. Forman, et al., Cell 81:687-693 (1995) and W. Seol, et al., Mol. Endocrinol. 9:72-85 (1995)). FXR binds to DNA as a heterodimer with the 9-cis retinoic acid receptor (RXR). The FXR/RXR heterodimer preferentially binds to response elements composed of two nuclear receptor half sites of the consensus AG(G/T)TCA organized as an inverted repeat and separated by a single nucleotide (IR-1 motif) (B M. Forman, et al., Cell 81:687-693 (1995)). An early report showed that rat FXR is activated by micromolar concentrations of farnesoids such as farnesol and juvenile hormone (B M. Forman, et al., Cell 81:687-693 (1995)). However, these compounds failed to activate the mouse and human FXR, leaving the nature of the endogenous FXR ligand in doubt. Several naturally-occurring bile acids bind to and activate FXR at physiological concentrations (PCT WO 00/37077, published 29 Jun. 2000)). As discussed therein, the bile acids that serve as D(R ligands include chenodeoxycholic acid (CDCA), deoxycholic acid (DCA), lithocholic acid (LCA), and the taurine and glycine conjugates of these bile acids.

Bile acids are cholesterol metabolites that are formed in the liver and secreted into the duodenum of the intestine, where they have important roles in the solubilization and absorption of dietary lipids and vitamins. Most bile acids (~95%) are subsequently reabsorbed in the ileum and returned to the liver via the enterohepatic circulatory system. The conversion of cholesterol to bile acids in the liver is under feedback regulation: Bile acids down-regulate the transcription of cytochrome P450 7a (CYP7a), which encodes the enzyme that catalyzes the rate limiting step in bile acid biosynthesis. There are data to suggest that FXR is involved in the repression of CYP7a expression by bile acids, although the precise mechanism remains unclear (D W. Russell, Cell 97:539-542 (1999)). In the ileum, bile acids induce the expression of the intestinal bile acid binding protein (IBABP), a cytoplasmic protein which binds bile acids with high affinity and may be involved in their cellular uptake and trafficking. Two groups have now demonstrated that bile acids mediate their effects on IBABP expression through activation of FXR, which binds to an IR-1 type response element that is conserved in the human, rat, and mouse IBABP gene promoters (14; 17). Thus FXR is involved in both the stimulation (IBABP) and the repression (CYP7a) of target genes involved in bile acid and cholesterol homeostasis.

SUMMARY OF THE INVENTION

As a first aspect, the present invention provides a compound of formula (I):

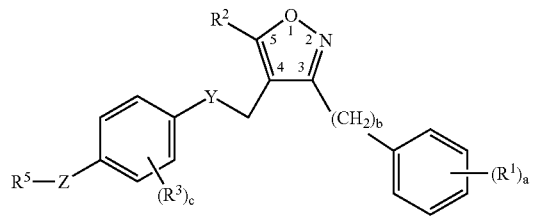

wherein:

a is 1-5;

each $R^1$ is the same or different and is independently selected from the group consisting of halo, alkyl, alkenyl, —$OR^6$, —$S(O)_jR^6$, —$NR^6R^7$, —$R^4OR^6$, —$R^4S(O)_jR^6$, —$R^4NR^6R^7$ and cyano;

b is 0-3;

$R^2$ is selected from the group consisting of alkyl, alkenyl, $C_{3-6}$cycloalkyl, $C_{3-6}$cycloalkenyl, —$OR^6$, —$NR^6R^7$, —$R^4OR^6$, —$R^4NR^6R^7$, cyano and nitro;

Y is —O— or —N($R^8$)—;

c is 0-4;

each $R^3$ is the same or different and is independently selected from the group consisting of halo, alkyl, alkenyl, alkynyl, cycloalkyl, cycloalkenyl, —$OR^6$, —$COR^6$, —$CO_2R^6$, —$CH(R^6)OR^7$, —$S(O)_jR^6_1$, —$NR^6R^7$, —$R^4$cycloalkyl, —$R^4OR^6$, —$R^4COR^6$, —$R^4CO_2R^6$, —$R^4S(O)_jR^6$, —$R^4NR^6R^7$ and cyano Z is selected from the group consisting of —O—$R^4$—, —$R^4$—O—, —$S(O)_j$—$R^4$—, —$R^4$—$S(O)_j$—, —N($R^8$)—$R^4$—, —$R^4$—N($R^8$)—, —C(O)N($R^8$)—, —C(O)$R^4$N($R^8$)—, —$S(O)_jN(R^8)$— and —$S(O)_jR^4N(R^8)$—;

each $R^4$ is the same or different and is independently selected from the group consisting of alkylene and alkenylene;

$R^5$ is selected from the group consisting of $R^6$O—, $R^6O_2C$—, and

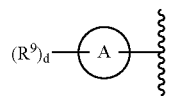

wherein Ring A is aryl or a 5-12 membered heterocycle or heteroaryl;

d is 0-4;

each $R^9$ is the same or different and is independently selected from the group consisting of halo, alkyl, alkenyl, alkynyl, cycloalkyl, —$OR^6$, —$COR^6$, —$CO_2R^6$, —$CH(R^6)OR^7$, —$S(O)_jR^6$, —$NR^6R^7_1$, —$R^4$cycloalkyl, —$R^4OR^6$, —$R^4COR^6$, —$R^4CO_2R^6$, —$R^4S(O)_jR^6$, —$R^4NR^6R^7$, cyano, 5-9 membered heterocycle and 5-9 membered heteroaryl;

each $R^6$ and $R^7$ are the same or different and are each independently selected from the group consisting of H, alkyl, alkenyl, $C_{3-6}$cycloalkyl and $C_{3-6}$cycolalkenyl;

$R^8$ is H or alkyl; and each f is the same or different and is independently selected from the group consisting of 0, 1 and 2;

or a pharmaceutically acceptable salt, solvate or physiologically functional derivative thereof.

In a second aspect, the present invention provides a pharmaceutical composition comprising a compound of formula (I). The pharmaceutical composition may further comprise a pharmaceutically acceptable carrier or diluent.

In a third aspect, the present invention provides a method for the treatment or prophylaxis of a condition mediated by FXR in a subject. The method comprises administering to the subject a therapeutically effective amount of a compound of formula (I).

In a fourth aspect, the present invention provides a method for the treatment or prophylaxis of cardiovascular disease in a subject The method comprises administering to the subject a therapeutically effective amount of a compound of formula (I). The cardiovascular disease may be selected from the group consisting of atherosclerosis and hypercholesterolemia.

In a fifth aspect, the present invention provides a method for the treatment or prophylaxis of cholestatic liver disease. The method comprises administering to the subject a therapeutically effective amount of a compound of formula (I).

In a sixth aspect, the present invention provides a method for the treatment or prophylaxis of organ fibrosis in a subject. The method comprises administering to the subject a therapeutically effective amount of a compound of formula (I).

In a seventh aspect, the present invention provides a method for increasing HDL cholesterol in a subject. The method comprises administering to the subject a therapeutically effective amount of a compound of formula (I).

In an eighth aspect, the present invention provides a method for lowering triglycerides in a subject. The method comprises administering to the subject a therapeutically effective amount of a compound of formula (I).

In a ninth aspect, the present invention provides a radiolabeled compound of formula (I).

In a tenth aspect, the present invention provides a process for preparing a compound of formula (I). The process comprises the steps of:

a) reducing a compound of formula (X):

X followed by chorination to prepare a compound of formula (XI):

XI and b) reacting the compound of formula (XI) with a compound of formula (XII):

$R^5\text{-}Z^1$  XII wherein $Z^1$ is —O—, —S(O)$_f$— or —N($R^8$)—;

to prepare a compound of formula (I-A):

I-A

In another aspect, the present invention provides another process for preparing a compound of formula (I). The process comprises the steps of:

a) rearranging the carbonyl functionality of the compound of formula (X):

X followed by hydrolysis to prepare a compound of formula (XIII):

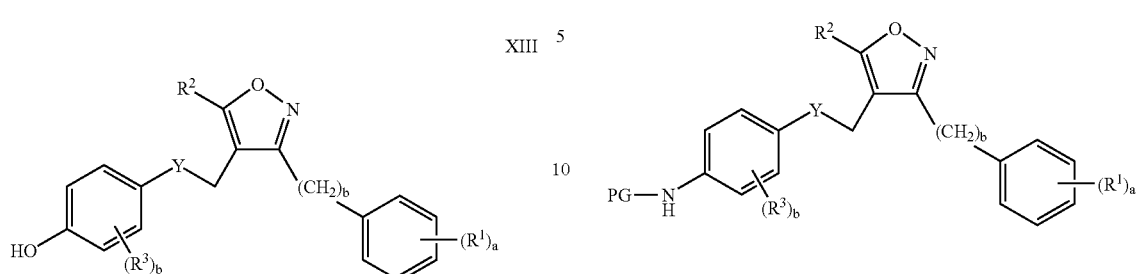

XIII and b) reacting the compound of formula (XIII) with a suitable electrophile to prepare a compound of formula (I-B):

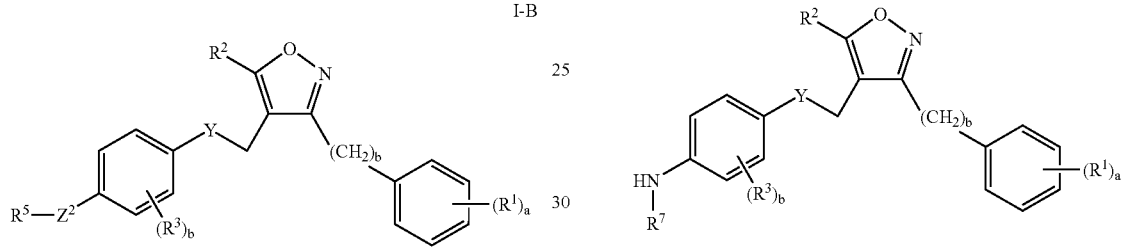

I-B wherein $Z^2$ is —$R^4$—O—.

In another aspect, the present invention provides another process for preparing a compound of formula (I). The process comprises the steps of:

a) reacting a protected compound of formula (XV):

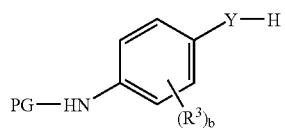

XV wherein PG is a protecting group;

with a compound of formula (VI):

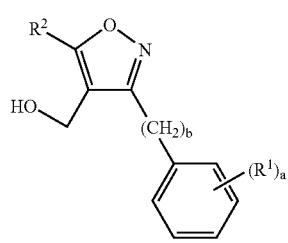

VI to prepare a compound of formula (XVI):

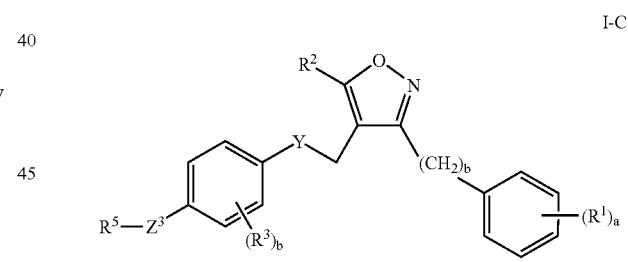

XVI b) optionally alkylating the compound of formula (XVI), followed by deprotecting the compound of formula (XVI) to prepare a compound of formula (XVII):

XVII and c) reacting the compound of formula (XVII) with a suitable electrophile to prepare a compound of formula (I-C):

I-C wherein $Z^3$ is selected from the group consisting of —$R^4$—O—, —$R^4$—S(O)$_f$—, —$R^4$—N($R^8$)—, —CON($R^8$)—, —C(O)$R^4$N($R^8$)—, —S(O)$_f$N($R^8$)— and —S(O)$_f$$R^4$N($R^8$)—.

In another aspect, the present invention provides a compound of formula (I) for use in therapy. The present invention also provides a compound of formula (I) for use in the treatment or prophylaxis of a condition mediated by FXR in a subject; a compound of formula (I) for use in the treatment or prophylaxis of cardiovascular disease in a subject; a compound of formula (I) for use in the treatment or prophylaxis of atherosclerosis in a subject; a compound of formula (I) for use in the treatment or prophylaxis of hypercholesterolemia in a subject; a compound of formula (I) for use in the treatment or prophylaxis of cholestatic liver disease in a subject; a compound of formula (I) for use in the treatment or prophylaxis of organ fibrosis; a compound of formula (I) for use in increasing HDL cholesterol in a subject; and a compound of formula (I) for use in lowering triglycerides in a subject.

In another aspect, the present invention provides the use of a compound of formula (I) for the preparation of a medicament for the treatment or prophylaxis of a condition mediated by FXR in a subject; the use of a compound of formula (I) for the preparation of a medicament for the treatment or prophylaxis of cardiovascular disease in a subject; the use of a compound of formula (I) for the preparation of a medicament for the treatment or prophylaxis of atherosclerosis in a subject; the use of a compound of formula (I) for the preparation of a medicament for the treatment or prophylaxis of hypercholesterolemia in a subject; the use of a compound of formula (I) for the preparation of a medicament for the treatment or prophylaxis of cholestatic liver disease in a subject; the use of a compound of formula (I) for the preparation of a medicament for the treatment or prophylaxis of organ fibrosis in a subject; the use of a compound of formula (I) for the preparation of a medicament for increasing HDL cholesterol in a subject; and the use of a compound of formula (I) for the preparation of a medicament for lowering triglycerides in a subject.

In another aspect, the present invention provides a pharmaceutical-composition comprising a compound of formula (I) for use in the treatment or prophylaxis of a condition mediated by FXR.

Further aspects of the present invention are described in the description of particular embodiments, examples, and claims which follow.

DETAILED DESCRIPTION OF THE PREFERRED EMBODIMENTS

As used herein, "a compound of the invention" or "a compound of formula (I)" means a compound of formula (I) or a pharmaceutically acceptable salt, solvate, or physiologically functional derivative thereof. Similarly, with respect to isolatable intermediates such as for example, compounds of formula (X), (XI), (XIII), (XV) and (XVI), the phrase "a compound of formula (number)" means a compound having that formula or a pharmaceutically acceptable salt, solvate or physiologically functional derivative thereof.

As used herein, the term "alkyl" refers to aliphatic straight or branched saturated hydrocarbon chains containing 1-8 carbon atoms. Examples of "alkyl" groups as used herein include but are not limited to methyl, ethyl, n-propyl, isopropyl, n-butyl, isobutyl, t-butyl, pentyl, hexyl, octyl and the like. The term "alkyl" also refers to halo substituted alkyl, including trihaloalkyl, such as trifluoromethyl and trifluoroethyl among others.

The term "alkylene" refers to a straight or branched alkyl bridge, i.e., the group -alkyl-, wherein alkyl is as defined above.

As used herein, the term "halo" refers to any halogen atom ie., fluorine, chlorine, bromine or iodine.

As used herein, the term "alkenyl" refers to an aliphatic straight or branched unsaturated hydrocarbon chain containing 2-8 carbon atoms and at least one and up to three carbon-carbon double bonds. Examples of "alkenyl" groups as used herein include but are not limited to ethenyl and propenyl. The term "alkenyl" also refers to halo substituted alkenyl.

The term "alkenylene" refers to a straight or branched alkenyl bridge, i.e., the group -alkenyl-, wherein alkenyl is as defined above.

As used herein, the term "alkynyl" refers to an aliphatic straight or branched unsaturated hydrocarbon chain containing 2-8 carbon atoms and at least one and up to three carbon-carbon triple bonds. Examples of "alkynyl" groups as used herein include but are not limited to propynyl. The term "alkynyl" also refers to halo substituted alkynyl.

As used herein, the term "cycloalkyl" refers to a non-aromatic monocyclic carbocyclic ring having from 3 to 8 carbon atoms (unless a different number of atoms is specified) and no carbon-carbon double bonds. "Cycloalkyl" includes by way of example cyclopropyl, cyclobutyl, cyclopentyl, cyclohexyl, cycloheptyl and cyclooctyl. "Cycloalkyl" also includes substituted cycloalkyl. The cycloalkyl may optionally be substituted on any available carbon with one or more substituents selected from the group consisting of halo, alkyl (including haloalkyl), alkenyl (including haloalkenyl), —OH, —O-alkyl, —NH$_2$, —NH(alkyl) —N(alkyl)$_2$, —CN, —NO$_2$ and —N$_3$. As will be appreciated by those skilled in the art, the number of possible substituents on the cycloalkyl ring will depend upon the size of ring. Particular cycloalkyl groups include C$_{3-6}$cycloalkyl and substituted C$_{3-6}$cycloalkyl.

As used herein, the term "cycloalkenyl" refers to a non-aromatic monocyclic carbocyclic ring having from 3 to 8 carbon atoms (unless a different number of atoms is specified) and from 1 to 3 carbon-carbon double bonds. "Cycloalkenyl" includes by way of example cyclopropenyl, cyclobutenyl, cyclopentenyl, cyclohexenyl, cycloheptenyl and cyclooctenyl. "Cycloalkenyl" also includes substituted cycloalkenyl. The cycloalkenyl may optionally be substituted on any available carbon with one or more substituents selected from the group consisting of halo, alkyl (including haloalkyl), alkenyl (including haloalkenyl), —OH, —O-alkyl, —NH$_2$, —NH(alkyl) —N(alkyl)$_2$, —CN, —NO$_2$ and —N$_3$. As will be appreciated by those skilled in the art, the number of possible substituents on the cycloalkenyl ring will depend upon the size of ring. Particular cycloalkenyl groups include C$_{3-6}$cycloalkenyl and substituted C$_{3-6}$cycloalkenyl.

The term "aryl" as used herein refers to an aromatic carbocyclic group selected from the group consisting of phenyl, 1-naphthyl and 2-naphthyl. As will be appreciated by those skilled in the art, the number of possible substituents on the aryl ring will depend upon the size of ring. For example, when the aryl ring is phenyl, the aryl ring may have up to 5 substituents selected from the foregoing list One skilled in the art will readily be able to determine the maximum number of possible substituents for a 1-naphthyl or 2-naphthyl ring. A particular aryl according to the invention is phenyl, which may be substituted as described above.

The term "heterocycle" refers to a monocyclic saturated or partially unsaturated, non-aromatic ring and fused bicyclic non-aromatic ring, having the specified number of members in the ring and being comprised of carbon and 1, 2 or 3 heteroatoms selected from N, O and S. Examples of particular heterocyclic groups include but are not limited to tetrahydrofuran, dihydropyran, tetrahydropyran, pyran, oxetane, thietane, 1,4-dioxane, 1,3-dioxane, 1,3-dioxalane, piperidine, piperazine, tetrahydropyrimidine, pyrrolidine, morpholine, thiomorpholine, thiazolidine, oxazolidine, tetrahydrothiopyran, tetrahydrothiophene, and the like. The term "heterocycle" also refers to substituted heterocycle wherein the heterocyclic ring bears one or more substituents selected from the group consisting of halo, alkyl, alkenyl, —OH, —Oalkyl, —NH$_2$, —NH(alkyl), —N(alkyl)$_2$, —NO$_2$ and —CN. As will be appreciated by those skilled in the art, the number of possible substituents on the heterocyclic ring will depend upon the size of ring. There are no restrictions on the positions of the optional substituents in the heterocycles. Thus, the term encompasses rings having a substituent attached to the ring through a heteroatom, particularly through N. One skilled in the art will readily be able to determine the maximum number and locations of possible substituents for any given heterocycle. Particular heterocycles according to the include piperidine and piperizine, either of which may be substituted as described above.

The term "heteroaryl" refers to an aromatic monocyclic ring or a fused bicyclic ring wherein at least one ring is aromatic, having the specified number of members in the ring, and being comprised of carbon and 1, 2 or 3 heteroatoms selected from N, O and S. Examples of particular heteroaryl groups include but are not limited to furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, and indazole. The term "heteroaryl" also refers to substituted heteroaryls wherein the heteroaryl ring bears one or more substituents selected from the group consisting of halo, alkyl, alkenyl, —OH, —Oalkyl, —NH$_2$, —NH(alkyl), —N(alkyl)$_2$, —NO$_2$ and —CN. As will be appreciated by those skilled in the art, the number of possible substituents on the heteroaryl ring will depend upon the size of ring. There are no restrictions on the positions of the optional substituents in heteroaryls. Thus, the term encompasses rings having a substituent attached to the ring through a heteroatom. One skilled in the art will readily be able to determine the maximum number and locations of possible substituents for any given heteroaryl. A preferred heteroaryl according to the invention is pyridine, which may be substituted as described above.

The term "members" (and variants thereof e.g., "membered") in the context of heterocyclic and heteroaryl rings refers to the total atoms, carbon and heteroatoms N, O and/or S, which form the ring. Thus, an example of a 6-membered heterocyclic ring is piperidine and an example of a 6-membered heteroaryl ring is pyridine.

As used herein, the term "optionally" means that the subsequently described event(s) may or may not occur, and includes both event(s) that occur and events that do not occur.

The present invention relates to compounds of formula (I):

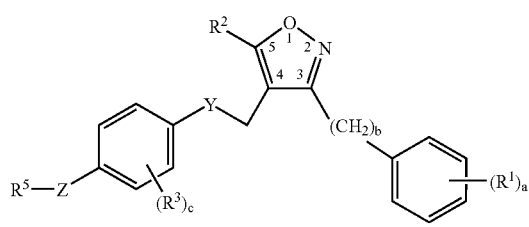

wherein:
a is 1-5;
each $R^1$ is the same or different and is independently selected from the group consisting of halo, alkyl, alkenyl, —OR$^6$, —S(O)$_f$R$^6$, —NR$^6$R$^7$, —R$^4$OR$^6$, —R$^4$S(O)$_f$R$^6$, —R$^4$NR$^6$R$^7$ and cyano;
b is 0-3;
$R^2$ is selected from the group consisting of alkyl, alkenyl, C$_{3-6}$cycloalkyl, C$_{3-6}$cycloalkenyl, —OR$^6$, —NR$^6$R$^7$, —R$^4$OR$^6$, —R$^4$NR$^6$R$^7$, cyano and nitro;
Y is —O— or —N(R$^8$)—,
c is 0-4;
each $R^3$ is the same or different and is independently selected from the group consisting of halo, alkyl, alkenyl, alkynyl, cycloalkyl, cycloalkenyl, —OR$^6$, —COR$^6$, —CO$_2$R$^6_1$, —CH(R$^6$)R$^7_1$, —S(O)$_f$R$^6$, —NR$^6$R$^7$, —R$^4$cycloalkyl, —R$^4$OR$^6$, —R$^4$CO$_2$R$^6$, —R$^4$S(O)$_f$R$^6$, —R$^4$NR$^6$R$^7$ and cyano;
Z is selected from the group consisting of —O—R$^4$—, —R$^4$—O—, —S(O)$_f$R$^4$—, —R$^4$—S(O)$_f$—, —N(R$^8$)—R$^4$—, —R$^4$—N(R$^8$)—, —C(O)N(R$^8$)—, —C(O)R$^4$N(R$^8$)—, —S(O)$_f$N(R$^8$)— and —S(O)$_f$R$^4$N(R$^8$)—;
each $R^4$ is the same or different and is independently selected from the group consisting of alkylene and alkenylene;
$R^5$ is selected from the group consisting of R$^6$O—, R$^6$O$_2$C—, and

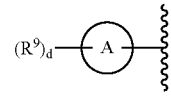

wherein Ring A is aryl or a 5-12 membered heterocycle or heteroaryl;
d is 0-4;
each $R^9$ is the same or different and is independently selected from the group consisting of halo, alkyl, alkenyl, alkynyl, cycloalkyl, —OR$^6$, —COR$^6$, —CO$_2$R$^6$, —CH(R$^6$)OR$^7$, —S(O)$_f$R$^6$, —NR$^6$R$^7$, —R$^4$cycloalkyl, —R$^4$OR$^6$, —R$^4$COR$^6$, —R$^4$CO$_2$R$^6$, —R$^4$S(O)$_f$R$^6$, —R$^4$NR$^6$R$^7$, cyano, 5-9 membered heterocycle and 5-9 membered heteroaryl;
each $R^6$ and $R^7$ are the same or different and are each independently selected from the group consisting of H, alkyl, alkenyl, C$_{3-6}$cycloalkyl and C$_{3-6}$cycolalkenyl;
$R^8$ is H or alkyl; and
each f is the same or different and is independently selected from the group consisting of 0, 1 and 2;

or a pharmaceutically acceptable salt, solvate or physiologically functional derivative thereof.

In the compounds of formula (I) the group(s) $R^1$ may be bonded in the ortho, meta or para positions. In one embodiment, the compound of formula (I) is defined wherein a is 1-2. In one particular embodiment, a is 2. In one particular embodiment, a is 2 each $R^1$ is in the ortho position.

In one embodiment, the compounds of formula (I) are defined wherein each $R^1$ is the same or different and is independently selected from the group consisting of halo and —OR$^6$, or any subset thereof. In a particular embodiment, each $R^1$ is the same or different and is independently selected from the group consisting of halo and —O-alkyl, or any subset thereof. More specifically, in one embodiment, each $R^1$ is the same or different and is independently selected from the group consisting of Cl, F, and —O—CF$_3$, or any subset thereof.

In one embodiment, the compounds of formula (I) are defined wherein b is 0 or 1. In one particular embodiment, b is 0. In one particular embodiment, b is 1.

In one embodiment of the present invention, $R^2$ is selected from the group consisting of alkyl and $C_{3-6}$cycloalkyl. In one particular embodiment, $R^2$ is alkyl. More specifically, particular groups defining $R^2$ are selected from the group consisting of methyl, ethyl, isopropyl, and cyclopropyl, or any subset thereof. In one particular embodiment, $R^2$ is isopropyl.

In one embodiment, the compounds of formula (I) are defined wherein Y is —O—. In another particular embodiment, the compounds of formula (I) are defined wherein Y is —N($R^8$)—. In one embodiment wherein Y is —N($R^8$)—, $R^8$ is selected from the group consisting of H and methyl.

In one embodiment, the compounds of formula (I) are defined wherein c is 0-2. In one particular embodiment, c is 1. In another embodiment, c is 0.

In the embodiment wherein c is 1, 2, 3 or 4, the compounds of formula (I) are defined wherein each $R^3$ is the same or different and is independently selected from the group consisting of halo and alkyl, or any subset thereof. More specifically, in one embodiment each $R^3$ is the same or different and is independently selected from the group consisting of Cl and methyl.

In one embodiment, the compounds of formula (I) are defined wherein Z is selected from the group consisting of —O—$R^4$—, —$R^4$—O—, —S(O)$_f$—$R^4$—, —N($R^8$)—$R^4$—, —$R^4$—N($R^8$)—, —C(O)N($R^8$)—, —C(O)$R^4$N($R^8$)—, —S(O)$_f$N($R^8$)— and —S(O)$_f$$R^4$N($R^8$)—, or any subset thereof. In a particular embodiment, Z is selected from the group consisting of —O—$R^4$—, —N($R^8$)—$R^4$—, —$R^4$—N($R^8$)—, —C(O)N($R^8$)— and —S(O)$_f$N($R^8$)—. More particularly, Z is selected from the group consisting of —O—$R^4$—, —$R^4$—N($R^8$)—and —S(O)$_f$N($R^8$)—.

Specific examples of groups defining Z may be selected from the group consisting of —O—$CH_2$—, —$CH_2$—O—, —S—$CH_2$—, —NH—$CH_2$—, —$CH_2$—NH—, —N($CH_3$)—$CH_2$—, —$CH_2$—N($CH_3$)—, —CH=CH—$CH_2$—N($CH_3$)—, —CH($CH_2$)—$CH_2$—N($CH_3$)—, —$CH_2$—CH=CH—$CH_2$—N($CH_3$)—, —($CH_2$)$_3$—N($CH_3$)—, —($CH_2$)$_4$—N($CH_3$)—, —($CH_2$)$_5$—N($CH_3$)—, —C(O)N(H)—, —C(O)N($CH_3$)—, —C(O)—$CH_2$—N($CH_3$)—, —S(O)$_2$N(H)—, —S(O)$_2$N($CH_3$)— and —S(O)$_2$N($CH_2$$CH_3$)—, or any subset thereof. In one particular embodiment, Z is selected from the group consisting of —NH—$CH_2$—, —$CH_2$—NH—, —N($CH_3$)—$CH_2$—, —$CH_2$—N($CH_3$)—, —C(O)N(H)— and —C(O)N($CH_3$)—, or any subset thereof.

In one embodiment the compounds of formula (I) are defined wherein $R^5$ is selected from the group consisting of $R^6O_2C$—, and

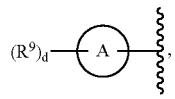

or any subset thereof. In one embodiment, the compounds of formula (I) are defined wherein $R^5$ is $R^6O_2C$—. In one particular embodiment, $R^5$ is $R^6O_2C$—, wherein $R^6$ is selected from the group consisting of H and alkyl.

In another particular embodiment, $R^5$ is

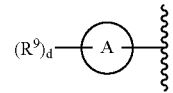

(the "Ring A moiety").

In one embodiment wherein $R^5$ is the Ring A moiety, Ring A is selected from the group consisting of phenyl, furan, thiophene, pyrrole, oxazole, thiazole, imidazole, pyrazole, isoxazole, pyran, pyridine, pyrimidine, piperidine, dioxane, morpholine, thiomorpholine, pyridazine, pyrazine, piperizine, indole, isoindole, benzofuran, benzothiophene, benzimidazole, benzooxadiazole, quinoline and isoquinoline, or any subset thereof. In a particular embodiment wherein $R^5$ is the Ring A moiety, Ring A is selected from the group consisting of phenyl and furan. In one particular embodiment wherein $R^5$ is the Ring A moiety, Ring A is phenyl.

In one embodiment wherein $R^5$ is the Ring A moiety, d is 0, 1 or 2. In one particular embodiment d is 1.

In one embodiment wherein $R^5$ is the Ring A moiety and d is 1 or more, each $R^9$ is the same or different and is independently selected from the group consisting of halo, alkyl, —$OR^6$, —$CO_2R^6$, —S(O)$_f$$R^6$, —$R^4OR^6$, cyano and 5-9 membered heteroaryl. More particularly, in one embodiment wherein $R^5$ is the Ring A moiety and d is 1 or more, each $R^9$ is the same or different and is independently selected from the group consisting of halo, alkyl, —O-alkyl, —$R^4$—OH, —$R^4$-Oalkyl, —COOH, —COOalkyl, —S(O)$_2$alkyl, cyano and thiadiazole. Specific examples of particular groups defining $R^9$ are selected from the group consisting of Cl, $CH_3$, —$CH_2OH$, —$CO_2H$, —$CO_2CH_3$, —$CO_2CH_2CH_3$, —$OCH_3$, —S(O)$_2$$CH_3$, cyano and thiadiazole. In one particular embodiment wherein $R^5$ is the Ring A moiety and d is 1 or more, each $R^9$ is the same or different and is independently selected from the group consisting of —$CO_2H$ and —$CO_2$alkyl (e.g., —$CO_2CH_3$).

Specific examples of particular compounds of the present invention are selected from the group consisting of:

3-{[(4-{[3-(2,6-Dichlorophenyl)-5-isopropylisoxazol-4-yl]methoxy}-2-methylphenyl)-(methyl)amino]methyl}benzoic acid;

Methyl 4-[(4-{[3-(2,6-dichlorophenyl)-5-isopropyl-4-isoxazolyl]methoxy}-2-dimethylanilino)methyl]benzoate;

3-[{(2-Chloro-4-{[3-(2,6-dichlorophenyl)-5-isopropylisoxazol-4-yl]methoxy}-phenyl)amino]methyl}benzoic acid;

5-[(4-{[3-(2,6-Dichlorophenyl)-5-isopropyl-4-isoxazolyl]methoxy}-2-dimethyl-anilino)methyl]-2-furoic acid;

4-[(4-{[3-(2,6-Dichlorophenyl)-5-isopropyl-4-isoxazolyl]methoxy}-2-dimethyl-anilino)methyl]benzoic acid;

Methyl 2-[(4-{[3-(2,6-dichlorophenyl)-5-isopropyl-4-isoxazolyl]methoxy}-2-dimethylanilino)methyl]-3-furoate;

N-(2,1,3-Benzoxadiazol-5-ylmethyl)-4-{[3-(2,6-dichlorophenyl)-5-isopropyl-4-isoxazolyl]methoxy}-N,2-dimethylaniline;

N-(4-{[3-(2,6-Dichlorophenyl)-5-isopropyl-4-isoxazolyl]methoxy}-2-methylphenyl)-N-methyl-N-[4-(1,2,3-thiadiazol-4-yl)benzyl]amine;

4-[(4-{[3-(2,6-Dichlorophenyl)-5-isopropyl-4-isoxazolyl]methoxy}-2-dimethyl-anilino)methyl]benzonitrile;

2-[(4-{[3-(2,6-Dichlorophenyl)-5-isopropyl-4-isoxazolyl]methoxy}-2-dimethyl-anilino)methyl]-3-furoic acid;

{3-[(4-{[3-(2,6-Dichlorophenyl)-5-isopropyl-4-isoxazolyl]methoxy}-2-dimethylanilino)methyl]phenyl}methanol;

{4-[(4-{[3-(2,6-Dichlorophenyl)-5-isopropyl-4-isoxazolyl]methoxy}-2-dimethylanilino)methyl]phenyl}methanol;

3-(4-{[3-(2,6-Dichlorobenzyl)-5-ethyl-4-isoxazolyl]methoxy)-2-dimethylanilino)methyl]benzoic acid;

3-{[({5-Isopropyl-3-(2,4,6-trichlorophenyl)isoxazol-4-yl]methoxy) -2-methylphenyl)-(methyl)amino]methyl}benzoic acid;

3-[(4-{[3-(2,6-Dichlorobenzyl)-5-isopropyl-4-isoxazolyl]methoxy}-2-dimethylanilino)methyl]benzoic acid;

3-{[(4-{[3-(2-Chlorobenzyl)-5-isopropylisoxazol-4-yl]methoxy}-2-methylphenyl)-(methyl)-amino]methyl}benzoic acid;

3-[(4-{[5-Cyclopropyl-3-(2,6-dichlorobenzyl)-4-isoxazolyl]methoxy}-2-dimethylanilino)methyl]benzoic acid;

5-{[4-({5-Isopropyl-3-[2-(trifluoromethoxy)phenyl]-4-isoxazolyl }methoxy)-2-dimethylanilino]methyl}-2-furoic acid;

4-{[4-({5-Isopropyl-3-[2-(trifluoromethoxy)phenyl]-4-isoxazolyl }methoxy)-2-dimethylanilino]methyl}benzoic acid;

3-{[4-({5-Isopropyl-3-[2-(trifluoromethoxy)phenyl]-4-isoxazolyl}methoxy)-2-dimethylanilino]methyl}benzoic acid;

Methyl 5-{[4-({5-isopropyl-3-[2-(trifluoromethoxy)phenyl]-4-isoxazolyl}methoxy)-2-dimethylanilino]methyl}-2-furoate;

Methyl 4-{[4-({5-isopropyl-3-[2-(trifluoromethoxy)phenyl]-4-isoxazolyl}methoxy)-2-dimethylanilino]methyl}benzoate;

4-{[(2-Chloro-4-{[3-(2,6-dichlorophenyl)-5-isopropylisoxazol-4-yl]methoxy}phenyl)-amino]carbonyl}benzoic acid;

Methyl 3-[(2-chloro-4-{[3-(2,6-dichlorophenyl)-5-isopropyl-4-isoxazolyl]methoxy}-anilino)carbonyl]benzoate;

Methyl 4-[(2-chloro-4-{[3-(2,6-dichlorophenyl)-5-isopropyl-4-isoxazolyl]methoxy}-anilino)carbonyl]benzoate;

3-[(4-{[3-(2,6-Dichlorophenyl)-5-isopropyl-4-isoxazolyl]methoxy}-2-methylanilino)-carbonyl]benzoic acid;

4-[(4-{[3-(2,6-Dichlorophenyl)-5-isopropyl-4-isoxazolyl]methoxy}-2-methylanilino)-carbonyl]benzoic acid;

3-[(2-Chloro-4-{[3-(2,6-dichlorophenyl)-5-isopropyl-4-isoxazolyl]methoxy}-anilino)carbonyl]benzoic acid;

3-[(4-{[3-(2,6-Dichlorophenyl)-5-isopropyl-4-isoxazolyl]methoxy}-2-dimethylanilino)carbonyl]benzoic acid;

3-[(2-Chloro-4-{[3-(2,6-dichlorophenyl)-5-isopropyl-4-isoxazolyl]methoxy}-methylanilino)carbonyl]benzoic acid;

4-[(2-Chloro-4-{[3-(2,6-dichlorophenyl)-5-isopropyl-4-isoxazolyl]methoxy}-methylanilino)carbonyl]benzoic acid;

3-{[4-({5-Isopropyl-3-[2-(trifluoromethoxy)phenyl]-4-isoxazolyl}methoxy)-2-dimethylanilino]carbonyl}benzoic acid;

3-{[4-({5-Isopropyl-3-[2-(trifluoromethoxy)phenyl]-4-isoxazolyl}methoxy)-2-methylanilino]carbonyl}benzoic acid;

3-{[2-Chloro-4-({5-isopropyl-3-[2-(trifluoromethoxy)phenyl]-4-isoxazolyl}-methoxy)methylanilino]carbonyl}benzoic acid;

Methyl 3-{[(4-{[3-(2,6-dichlorophenyl)-5-isopropylisoxazol-4-yl]methoxy}-2-methylphenyl)(methyl)amino]sulfonyl}benzoate;

Methyl 3-{[(2-chloro-4-{[3-(2,6-dichlorophenyl)-5-isopropylisoxazol-4-yl]methoxy}-2-phenyl)amino]sulfonyl}benzoate;

Methyl 3-{[(4-{[3-(2,6-dichlorophenyl)-5-isopropylisoxazol-4-yl]methoxy}-2-methylphenyl)amino]sulfonyl}benzoate;

Methyl 3-{[(4-{[3-(2,6-dichlorophenyl)-5-isopropylisoxazol-4-yl]methoxy}phenyl)-amino]-sulfonyl}benzoate;

3-{[(4-{[3-(2,6-Dichlorophenyl)-5-isopropylisoxazol-4-yl]methoxy}-2-methylphenyl)-amino]sulfonyl}benzoic acid;

3-{[(4-{[3-(2,6-Dichlorophenyl)-5-isopropylisoxazol-4-yl]methoxy}phenyl)amino]-sulfonyl}benzoic acid;

Methyl 3-{[(2-chloro-4-{[3-(2,6-dichlorophenyl)-5-isopropylisoxazol-4-yl]methoxy}-phenyl)(methyl)amino]sulfonyl}benzoate;

Methyl 3-{[(4-{[3-(2,6-dichlorophenyl)-5-isopropylisoxazol-4-yl]methoxy}phenyl)-(methyl)amino]sulfonyl}benzoate;

Methyl 3-{[(2-chloro-4-{[3-(2,6-dichlorophenyl)-5-isopropylisoxazol-4-yl]methoxy}-phenyl)(ethyl)amino]sulfonyl}benzoate; Methyl 3-{[(4-{[3-(2,6-dichlorophenyl)-5-isopropylisoxazol-4-yl]methoxy) -2-methyl-phenyl)(ethyl)amino]sulfonyl}benzoate;

Methyl 3-{[(4-{[3-(2,6-dichlorophenyl)-5-isopropylisoxazol-4-yl]methoxy}phenyl)-(ethyl)-amino]sulfonyl}benzoate;

3-{[(2-Chloro-4-{[3-(2,6-dichlorophenyl)-5-isopropylisoxazol-4-yl]methoxy}-phenyl)-amino]sulfonyl}benzoic acid;

3-{[(2-Chloro-4-{[3-(2,6-dichlorophenyl)-5-isopropylisoxazol-4-yl]methoxy}-phenyl)-(methyl)amino]sulfonyl}benzoic acid;

3-{[(4-{[3-(2,6-Dichlorophenyl)-5-isopropylisoxazol-4-yl]methoxy}-2-methylphenyl)-(methyl)amino]sulfonyl}benzoic acid;

3-{[(4-{[3-(2,6-Dichlorophenyl)-5-isopropylisoxazol-4-yl]methoxy}phenyl)(methyl)-amino]sulfonyl}benzoic acid;

3-{[(2-Chloro-4-[3-(2,6-dichlorophenyl)-5-isopropylisoxazol-4-yl]methoxy}phenyl)-(ethyl)amino]sulfonyl}benzoic acid;

3-{[(4-{[3-(2,6-Dichlorophenyl)-5-isopropylisoxazol-4-yl]methoxy}-2-methylphenyl)-(ethyl)amino]sulfonyl}benzoic acid;

3-{[(4-{[3-(2,6-Dichlorophenyl)-5-isopropylisoxazol-4-yl]methoxy}phenyl)(ethyl)-amino]sulfonyl}benzoic acid;

Methyl 4-[(2-chloro-4-[3-(2,6-dichlorophenyl)-5-isopropyl-isoxazol-4-yl]methoxy}-phenyl)amino]sulfonyl}benzoate;

Methyl 4-{[(4-{[3-(2,6-dichlorophenyl)-5-isopropylisoxazol-4-yl]methoxy}-2-methyl-phenyl)amino]sulfonyl}benzoate;

Methyl 4-{[(4-{[3-(2,6-dichlorophenyl)-5-isopropylisoxazol-4-yl]methoxy}phenyl)-amino]sulfonyl}benzoate;

4-{[(2-Chloro-4-{[3-(2,6-dichlorophenyl)-5-isopropylisoxazol-4-yl]methoxy}phenyl)-amino]sulfonyl}benzoic acid;

4-{[(4-{[3-(2,6-Dichlorophenyl)-5-isopropylisoxazol-4-yl]methoxy)-2-methylphenyl)-amino]sulfonyl}benzoic acid;

4-{[(4-{[3-(2,6-Dichlorophenyl)-5-isopropylisoxazol-4-yl]methoxy}phenyl)amino]-sulfonyl}benzoic acid;

Methyl 4-{[(4-[3-(2,6-dichlorophenyl)-5-isopropylisoxazol-4-yl]methoxy}-2-methyl-phenyl)(methyl)amino]sulfonyl}benzoate;

Methyl 4-{[(4-{[3-(2,6-dichlorophenyl)-5-isopropylisoxazol-4-yl]methoxy}phenyl)-(methyl)amino]sulfonyl}benzoate;

Methyl 4-{[(4-{[3-(2,6-dichlorophenyl)-5-isopropylisox-azol-4-yl]methoxy}phenyl)-(ethyl)amino]sulfonyl}benzoate;
4-{[(2-Chloro-4-{[3-(2,6-dichlorophenyl)-5-isopropylisox-azol-4-yl]methoxy}phenyl)-(methyl)amino]sulfonyl}benzoic acid;
4-{[(4-{[3-(2,6-Dichlorophenyl)-5-isopropylisoxazol-4-yl]methoxy}-2-methylphenyl)-(methyl)amino]sulfonyl}benzoic acid;
4-{[(4-{[3-(2,6-Dichlorophenyl)-5-isopropylisoxazol-4-yl]methoxy}phenyl)(methyl)-amino]sulfonyl}benzoic acid;
4-{[(2-Chloro-4-{[3-(2,6-dichlorophenyl)-5-isopropylisox-azol-4-yl]methoxy}phenyl)-(ethyl)amino]sulfonyl}benzoic acid;
4-{[(4-{[3-(2,6-Dichlorophenyl)-5-isopropylisoxazol-4-yl]methoxy}-2-methylphenyl)-(ethyl)amino]sulfonyl}benzoic acid;
4-{[(4-{[3-(2,6-Dichlorophenyl)-5-isopropylisoxazol-4-yl]methoxy}phenyl)(ethyl)amino]-sulfonyl}benzoic acid;
3-({[2-Chloro-4-({5-isopropyl-3-[2-(trifluoromethoxy)phe-nyl]isoxazol-4-yl}methoxy)-phenyl]amino}sulfonyl)ben-zoic acid;
3-({[4-({5-Isopropyl-3-[2-(trifluoromethoxy)phenyl]isox-azol-4-yl}methoxy)-2-methyl-phenyl]amino]sulfonyl)benzoic acid;
Methyl 3-{[[2-chloro-4-({5-isopropyl-3-[2-(trifluo-romethoxy)phenyl]-isoxazol-4-yl}methoxy)phenyl](me-thyl)amino]sulfonyl}benzoate;
Methyl 3-{[[4-({5-isopropyl-3-[2-(trifluoromethoxy)phe-nyl]isoxazol-4-yl}methoxy)-2-methylphenyl](methyl)amino]sulfonyl}benzoate;
3-{[[2-Chloro-4-({5-isopropyl-3-[2-(trifluoromethoxy)phe-nyl]isoxazol-4-yl}methoxy)-phenyl](methyl)amino]sulfonyl}benzoic acid;
3-{[[4-({5-Isopropyl-3-[2-(trifluoromethoxy)phenyl]isox-azol-4-yl}methoxy)-2-methyl-phenyl](methyl)amino]sulfonyl}benzoic acid;
3-{[(4-{[3-(2,6-Dichlorobenzyl)-5-ethylisoxazol-4-yl]methoxy}-2-methylphenyl)(methyl)-amino]sulfonyl}benzoic acid;
Methyl 4-[(2-chloro-4-{[3-(2,6-dichlorophenyl)-5-isopro-pylisoxazol-4-yl]methoxy}-benzyl)oxy]benzoate;
Methyl 3-[(2-chloro-4-{[3-(2,6-dichlorophenyl)-5-isopro-pylisoxazol-4-yl]methoxy}-benzyl)-oxy]benzoate;
3-[(2-Chloro-4-{[3-(2,6-dichlorophenyl)-5-isopropylisox-azol-4-yl]methoxy}-benzyl)oxy]-benzoic acid;
3-[(2-Chloro-4-{[3-(2,6-dichlorophenyl)-5-isopropylisox-azol-4-yl]methoxy}-benzyl)thiol-benzoic acid;
3-[(4-{[3-(2,6-Dichlorophenyl)-5-isopropylisoxazol-4-yl]methoxy}-2methylbenzyl)-oxy]-benzoic acid;
3-[(4-{[3-(2,6-Dichlorophenyl)-5-isopropylisoxazol-4-yl]methoxy}-2-methylbenzyl)-thio]-benzoic acid;
4-1(2-Chloro-4-{[3-(2,6-dichlorophenyl)-5-isopropylisox-azol-4-yl]methoxy}benzyl)-oxy]benzoic acid;
4-[(2-Chloro-4-{[3-(2,6-dichlorophenyl)-5-isopropylisox-azol-4-yl]methoxy}benzyl)-thio]-benzoic acid;
Methyl 3-{[2-chloro-4-({5-isopropyl-3-[2-(trifluo-romethoxy)-phenyl]isoxazol-4-yl}methoxy)benzyl]oxy}benzoate;
Methyl 3-{[4-({5-isopropyl-3-[2-(trifluoromethoxy)phenyl]isoxazol-4-yl}methoxy)-2-methylbenzyl]oxy}benzoate;
3-{[2-Chloro-4-({5-isopropyl-3-[2-(trifluoromethoxy)phe-nyl]isoxazol-4-yl}methoxy)-benzyl]oxy}benzoic acid;
3-{[4-({5-Isopropyl-3-[2-(trifluoromethoxy)phenyl]isox-azol-4-yl}methoxy)-2-methyl-benzyl]oxy}benzoic acid;
3-[(2-Chloro-4-{[3-(2,6-dichlorobenzyl)-5-ethylisoxazol-4-yl]methoxy}benzyl)oxy]-benzoic acid;
Methyl 3-{[2-chloro-4-({5-isopropyl-3-[2-(trifluoro-meth-oxy)phenyl]isoxazol-4-yl}methoxy)benzyl]thio}benzoate;
Methyl 3-{[4-({5-isopropyl-3-[2-(trifluoromethoxy)phenyl]isoxazol-4-yl}methoxy)-2-methylbenzyl]thio}benzoate;
3-{[2-Chloro-4-({5-isopropyl-3-[2-(trifluoromethoxy)phe-nyl]isoxazol-4-yl}methoxy)-benzyl]thio}benzoic acid;
3-{[4-({5-Isopropyl-3-[2-(trifluoromethoxy)phenyl]isox-azol-4-yl}methoxy)-2-methyl-benzyl]thio}benzoic acid;
Methyl 3-[(2-chloro-4-{[3-(2,6-dichlorophenyl)-5-isopro-pylisoxazol-4-yl]methoxy}benzyl)(methyl)amino]ben-zoate;
3-[(2-Chloro-4-{[3-(2,6-dichlorophenyl)-5-isopropylisox-azol-4-yl]methoxy}benzyl)-(methyl)amino]benzoic acid;
3-[(2-Chloro-4-{[3-(2,6-dichlorophenyl)-5-isopropylisox-azol-4-yl]methoxy}benzyl)-amino]benzoic acid;
Ethyl 3-{[2-chloro-4-({5-isopropyl-3-[2-(trifluoromethoxy)phenyl]-4-isoxazolyl}-methoxy)benzyl]amino}benzoate;
3-{[2-Chloro-4-({5-isopropyl-3-[2-(trifluoromethoxy)phe-nyl]-4-isoxazolyl}methoxy)-benzyl]amino}benzoic acid;
3-[[2-Chloro-4-({5-isopropyl-3-[2-(trifluoromethoxy)phe-nyl]-4-isoxazolyl}methoxy)-benzyl](methyl)amino]ben-zoic acid;
Methyl 4-[(4-[3-(2,6-dichlorophenyl)-5-isopropylisoxazol-4-yl]methoxy}-2-methylphenoxy)methyl]benzoate;
Methyl 3-[(2-chloro-4-{[3-(2,6-dichlorophenyl)-5-isopro-pylisoxazol-4-yl]methoxy}-phenoxy)methyl]benzoate;
Methyl 3-[(4-{[3-(2,6dichlorophenyl)-5-isopropylisoxazol-4-yl]methoxy}-2-methyl-phenoxy)methyl]benzoate;
3-[(2-Chloro-4-{[3-(2,6-dichlorophenyl)-5-isopropylisox-azol-4-yl]methoxy}phenoxy)-methyl]benzoic acid;
3-[(4-{[3-(2,6-Dichlorophenyl)-5-isopropylisoxazol-4-yl]methoxy}-2-methylphenoxy)-methyl]benzoic acid; and
Methyl 4-[(4-{[3-(2,6-dichlorophenyl)-5-isopropylisoxazol-4-yl]methoxy}-2-methyl-phenoxy)methyl]benzoate, or a pharmaceutically acceptable salt, solvate or physiologically functional derivative thereof.

Certain compounds of formula (I) may exist in stereoisomeric forms (e.g. they may contain one or more asymmetric carbon atoms). The individual stereoisomers (enantiomers and diastereomers) and mixtures of these are included within the scope of the present invention. The present invention also covers the individual isomers of the compounds represented by formula (I) as mixtures with isomers thereof in which one or more chiral centers are inverted.

The present invention contemplates and includes all combinations and subsets of the particular groups defined above.

Suitable pharmaceutically acceptable salts according to the present invention will be readily determined by one skilled in the art and will include, for example, acid addition salts prepared from inorganic acids such as hydrochloric, hydrobromic, phosphoric, metaphosphoric, nitric, sulphonic, and sulfuric acids, and organic acids such as acetic, benzenesulphonic, benzoic, citric, ethanesulphonic, fumaric, gluconic, glycollic, isothionic, lactic, lactobionic, maleic, malic, methanesulphonic, succinic, p-toluenesulfonic, salicylic, tartaric, trifluoroacetic, formic, malonic, naphthalene-2-sulfonic, sulfamic, decanoic, orotic, 1-hydroxy-2-naphthoic, cholic, and pamoic. In one embodiment, the compounds of formula (I) are in the form of the hydrochloride salt When used in medicine, the salts of a compound of formula (I) should be pharmaceutically acceptable, but pharmaceutically unacceptable salts may conveniently be used to prepare the corresponding free base or pharmaceutically acceptable salts thereof.

As used herein, the term "solvate" refers to a crystal form containing the compound of formula (I) or a pharmaceutically acceptable salt thereof and either a stoichiometric or a non-stoichiometric amount of a solvent Solvents, by way of example, include water, methanol, ethanol, or acetic acid. Hereinafter, reference to a compound of formula (I) is to any physical form of that compound, unless a particular form, salt or solvate thereof is specified.

The term "physiologically functional derivative" as used herein refers to any pharmaceutically acceptable derivative of a compound of the present invention, for example, an ester or an amide of a compound of formula (I), which upon administration to an animal, particularly a mammal, such as a human, is capable of providing (directly or indirectly) a compound of the present invention or an active metabolite thereof. See for example, Burger's Medicinal Chemistry And Drug Discovery, 5th Edition, Vol 1: Principles And Practice.

Processes for preparing pharmaceutically acceptable salts, solvates and physiologically functional derivatives of the compounds of formula (I) are conventional in the art. See, e.g., Burger's Medicinal Chemistry And Drug Discovery 5th Edition, Vol 1: Principles And Practice.

As will be apparent to those skilled in the art, in the processes descibed below for the preparation of compounds of formula (I), certain intermediates, may be in the form of pharmaceutically acceptable salts, solvates or physiologically functional derivatives of the compound. Those terms as applied to any intermediate employed in the process of preparing compounds of formula (I) have the same meanings as noted above with respect to compounds of formula (I). Processes for preparing pharmaceutically acceptable salts, solvates and physiologically functional derivatives of such intermediates are known in the art and are analogous to the process for preparing pharmaceutically acceptable salts, solvates and physiologically functional derivatives of the compounds of formula (I).

In one embodiment, the compounds of formula (I) are FXR agonists. As used herein, the term "FXR agonist" refers to compounds which exhibit a $pEC_{50}$ greater than 4 in the FXR Affinity Binding Assay described below. More particularly, FXR agonists are compounds which exhibit a $pEC_{50}$ greater than 5 in the FXR Affinity Binding Assay described below.

The compounds of formula (I) are useful in therapy in subjects such as mammals, and particularly humans. In particular, the compounds of formula (I) is useful in the treatment or prophylaxis of a condition mediated by FXR in a subject such as a mammal, particularly a human. Conditions mediated by FXR include but are not limited to cardiovascular diseases, lipid-related diseases, disorders of the liver such as cholestatic liver disease and organ fibrosis. Thus the compounds of formula (I) are useful in the treatment or prophylaxis of cardiovascular disease in a subject such as a mammal, particularly a human. For example, the compounds of formula (I) are useful in the treatment or prophylaxis of atherosclerosis, arteriosclerosis, hypercholesterolemia or hyperlipidemia in a subject such as a mammal, particularly a human.

The compounds of formula (I) are also useful for the treatment or prophylaxis of lipid-related diseases. The compounds of the present invention increase the flow of bile acid. Increased flow of bile acids improves the flux of bile acids from the liver to the intestine. See, C. Sinal, Cell 102: 731-744 (2000). FXR null mice demonstrate that FXR plays a central role in bile acid homeostasis, and is therefore critical to lipid homeostasis by virtue of the regulation of enzymes and transporters that are critical to lipid catabolism and excretion. FXR therefore is an important target for the treatment of a number of cholestatic liver diseases and other lipid-related diseases and conditions. The compounds of formula (I) are therefore useful for the treatment or prophylaxis cholestatic liver disease. The compounds of formula (I) are also useful for the treatment or prophylaxis of gall stones.

The compounds of formula (I) are useful for the treatment or prophylaxis of organ fibrosis. Fibrotic disorders can be characterized as acute or chronic, but share the common characteristic of excessive collagen accumulation and an associated loss of function as normal tissue is replaced or displaced by fibrotic tissue. Acute forms of fibrosis include response to trauma, infections, surgery, burns, radiation and chemotherapy. Chronic forms of fibrosis may be due to viral infection, diabetes, obesity, fatty liver, hypertension, scleroderma and other chronic conditions that induce fibrosis.

Organs that are most commonly affected by fibrosis include liver, kidney and lung. Fibrosis may also occur in the heart, and in structures of the eyes. Organ fibrosis can cause the progressive loss of organ function. Retroperitoneal fibrosis (including idiopathic retroperitoneal fibrosis) may not originate from any major organ, but can involve and adversely affect the function of organs such as the kidneys.

Accordingly, as used herein, the term fibrosis refers to all recognized fibrotic disorders, including fibrosis due to pathological conditions or diseases, fibrosis due to physical trauma ('traumatic fibrosis'), fibrosis due to radiation damage, and fibrosis due to exposure to chemotherapeutics. As used herein, the term "organ fibrosis" includes but is not limited to liver fibrosis, fibrosis of the kidneys, pulmonary fibrosis, cardiac fibrosis, and fibrosis of ocular structures. "Traumatic fibrosis" includes but is not limited to fibrosis secondary to surgery (surgical scarring), accidental physical trauma, burns, and hypertrophic scarring.

As used herein, "liver fibrosis" includes liver fibrosis due to any cause, including but not limited to virally-induced liver fibrosis such as that due to hepatitis B and C; exposure to alcohol (alcoholic liver disease), pharmaceutical compounds, oxidative stress, cancer radiation therapy or industrial chemicals; and diseases such as primary biliary cirrhosis, fatty liver, obesity, non-alcoholic steatohepatitis, cystic fibrosis, hemochromatosis, and auto-immune hepatitis. Current therapy in liver fibrosis is primarily directed at removing the causal agent, e.g., removing excess iron (hemochromatosis), viral load (chronic viral hepatitis), or exposure to toxins (alcoholic liver disease). Anti-inflammatory drugs such as corticosteroids and colchicine are also known for use in treating inflammation that can lead to liver fibrosis. Other strategies for treating liver fibrosis are under development (see, e.g., Murphy et al., Expert Opin. Investig. Drugs 11:1575 (2002); Bataller and Brenner, Semin. Liver Dis. 21:437 (2001)).

The response of the liver to hepatocellular damage, similar to wound healing in other tissues, includes inflammation and tissue remodeling, with associated changes in the quantity and quality of the extracellular matrix. Progressive accumulation of extracellular matrix proteins, including collagen types I and III, eventually distorts the architecture of the liver by forming a fibrous scar, resulting in disrupted blood flow and an eventual deterioration in hepatic function. Hepatic stellate cells (HSC) have been identified as important mediators of the fibrotic process in the liver, and are believed to be primarily responsible for the synthesis of excess extracellular matrix seen in liver disease. Liver injury can result in quiescent HSCs converting to activated myofibroblast-like cells that proliferate, migrate, recruit inflammatory cells, and synthesize collagens and other extracellular matrix proteins. Various cytokines are reported to activate HSCs, including transforming growth factor B (TGFb). In liver, cholangiocyte production of TGFb is thought to be a key initiating step in the fibrotic process. Following liver injury, HSCs synthesize alpha-smooth muscle actin as part of the migration response, consequently a marked accumulation of alpha-smooth muscle actin (a-SMA) can be seen at areas of active liver fibrogenesis.

As is known in the art, liver fibrosis may be clinically classified into five stages (S0 to S4) of severity, usually based on histological examination of a biopsy specimen. S0 indicates no fibrosis, whereas S4 indicates cirrhosis. While various criteria for staging the severity of liver fibrosis exist, in general early-stages of fibrosis are identified by discrete, localized areas of scarring in one portal (zone) of the liver, whereas later stages of fibrosis are identified by bridging fibrosis (scarring that crosses zones of the liver).

The compounds of formula (I) are particularly useful for the treatment or prophylaxis of liver fibrosis in a mammal, particularly a human.

The compounds of formula (I) are also useful for increasing HDL cholesterol in a subject, such as a mammal, particularly a human. The compounds of formula (I) are useful for lowering triglycerides in a subject, such as a mammal, particularly a human.

The compounds of formula (I) are also useful for the treatment and prophylaxis of skin conditions such as disorders of the skin and mucosa characterized by a disrupted or dysfunctional epidermal barrier and disorders of epidermal differentiation and proliferation. Specific examples of skin conditions which may be treated according to the present invention are selected from the group consisting of development of the skin of premature infants of gestational age less than 33 weeks; atopic dermatitis; seborrheic dermatitis; inflammation to mucous membranes, such as cheilitis, chapped lips, nasal irritation and vulvovaginitis; eczematous dermatitis, such as that resulting from allergic and irritant contact, eczema craquelee, radiation and stasis dermatitis; ulcers and erosions, such as those due to chemical or thermal burns, bullous disorders, vascular compromise and ischemia; ichthyoses; epidermolysis bullosa; psoriasis; hypertrophic scars and keloids; intrinsic aging; dermatoheliosus; mechanical friction blistering; corticosteroid atrophy; and melanoma and non-melanoma skin cancer. The present invention provides a method for the treatment or prophylaxis of an FXR mediated disease or condition in a subject, such as a mammal, particularly a human. In particular, the present invention provides methods for the treatment or prophylaxis of cardiovascular disease including artherosclerosis and hypercholesteremia. The present invention also provides the use of a compound of formula (I) for the preparation of a medicament for the treatment or prophylaxis of a condition mediated by FXR, including cardiovascular disease.

The present invention provides a method for the treatment or prophylaxis of cholestatic liver disease in a subject, such as a mammal, particularly a human. The present invention also provides th use of a compound of formula (I) for the preparation of a medicament for the treatment or prophylaxis of cholestatic liver disease in a subject.

The present invention provides a method for the treatment or prophylaxis of organ fibrosis in a subject, such as a mammal, particularly a human. The present invention also provides th use of a compound of formula (I) for the preparation of a medicament for the treatment or prophylaxis of organ fibrosis in a subject.

The present invention provides a method for increasing HDL-cholesterol in a subject, such as a mammal, particularly a human. The present invention also provides the use of a compound of formula (I) for the preparation of a medicament for increaseing HDL-cholesterol in a subject.

The present invention also provides a method for lowering triglycerides in a subject, such as a mammal, particularly a human. The present invention also provides the use of a compound of formula (I) for the preparation of a medicament for lowering triglycerides in a subject.

The present invention also provides a method for the treatment or prophylaxis of skin conditions, particularly skin conditions mediated by FXR, in a subject such as a mammal, particularly a human. The present invention further provides the use of a compound of formula (I) for the preparation of a medicament for the treatment or prophylaxis of such skin condition in a subject.

All of the methods of the present invention comprise the step of administering a therapeutically effective amount of the compound of formula (I) or a pharmaceutically acceptable salt, solvate or physiologically functional derivative thereof. As used herein, the term "therapeutically effective amount" refers to an amount of the compound of formula (I) which is sufficient to achieve the stated effect Accordingly, a therapeutically effective amount of a compound of formula (I) used in the method for the treatment or prophylaxis of a condition mediated by FXR will be an amount sufficient for the treatment or prophylaxis of the condition mediated by FXR. A therapeutically effective amount of a compound of formula (I) for use in the method for the treatment or prophylaxis of cardiovascular disease will be an amount sufficient for the treatment or prophylaxis of cardiovascular disease. A therapeutically effective amount of a compound of formula (I) for use in the method for the treatment or prophylaxis of organ fibrosis will be an amount sufficient for the treatment or prophylaxis of organ fibrosis.

The amount of a compound of formula (I) or pharmaceutically acceptable salt, solvate or physiologically functional thereof, which is required to achieve the desired biological effect will depend on a number of factors such as the use for which it is intended, the means of administration, the recipient and the severity of the condition or disease being treated, and will be ultimately at the discretion of the attendant physician or veterinarian. In general, a typical daily dose for the treatment or prophylaxis of an FXR mediated disease or condition in a human, for instance, may be expected to lie in the range of from about 0.01 mg/kg to about 100 mg/kg. This dose may be administered as a single unit dose or as several separate unit doses or as a continuous infusion. Similar dosages would be applicable for the treatment of other diseases, conditions and therapies including increasing HDL-cholesterol and lowering triglycerides.

While it is possible that, for use in therapy, a therapeutically effective amount of a compound of formula (I) may be administered as the raw chemical, it is typically presented as the active ingredient of a pharmaceutical composition or formulation. Accordingly, the invention further provides a pharmaceutical composition comprising a compound of the formula (I). The pharmaceutical composition may further comprise one or more pharmaceutically acceptable carriers or diluents. The carrier(s) and/or diluent(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the formula (I) with one or more pharmaceutically acceptable carriers and/or diluents.

Pharmaceutical formulations may be presented in unit dose form containing a predetermined amount of active ingredient per unit dose. Such a unit may contain a therapeutically effective dose of the compound of formula (I) or a fraction of a therapeutically effective dose such that multiple unit dosage forms might be administered at a given time to achieve the desired therapeutically effective dose. Preferred unit dosage formulations are those containing a daily dose or sub-dose, as herein above recited, or an appropriate fraction thereof, of an active ingredient Furthermore, such pharmaceutical formulations may be prepared by any of the methods well known in the pharmacy art.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of active ingredient. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax or the like.

A compound of formula (I) can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

A compound of formula (I) may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research*, 3(6):318 (1986).

Pharmaceutical compositions adapted for topical administration may be formulated as ointments, creams, suspensions, lotions, powders, solutions, pastes, gels, sprays, aerosols or oils.

For treatments of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent.

Pharmaceutical compositions adapted for topical administration in the mouth include lozenges, pastilles and mouth washes.

Pharmaceutical compositions adapted for rectal administration may be presented as suppositories or as enemas.

Pharmaceutical compositions adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient. Pharmaceutical compositions adapted for administration by inhalation include fine particle dusts or mists, which may be generated by means of various types of metered, dose pressurised aerosols, nebulizers or insufflators.

Pharmaceutical compositions adapted for vaginal administration may be presented as pessaries, tampons, creams, gels, pastes, foams or spray formulations. Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the compositions may include other agents conventional in the art having regard to the type of formulation in question, for example those suitable for oral administration may include flavouring agents.

In the above-described methods of treatment and uses, a compound of formula (I) may be employed alone, in combination with one or more other compounds of formula (I) or in combination with other therapeutic agents. Thus, the present invention also encompasses pharmaceutical compositions further comprising one or more therapeutic agents. In one embodiment, the pharmaceutical compositions further comprise one or more lipid-altering agents. Examples of lipid-altering agents include but are not limited to LXR agonsts (such as derivatives of CDCA and LXR agonists described in PCT Publication No. WO02124632 to Glaxo-SmithKline); MHG-CoA reductase inhibitors such as statins (atorvastatin, fluvastatin, pravastatin, lovastatin, cerivastatin, and nisvastatin); squalene epoxidase inhibitors, squalene synthetase inhibitors, bile acid trasport inhibitors (BATi), human peroxisome proliferator activated receptor (PPAR) gamma agonists such as rosiglitazone, troglitazone, and pioglitazone and thiazolidinediones; PPAR alpha agonists such as clofibrate, fenogibrate and gemfibronzil; PPAR dual alpha/gamma agonists; cyclooxygenase-2 (COX-2) inhibitors such as rofecoxib and celecoxib; thrombin inhibitors; acyl-coenzyme A; cholesterol acyltransferase (ACAT) inhibitors including selective ACAT inhibitors; microsomal trilyceride transfer protein (MTP) inhibitors; probucol, niacin; cholester absorption inhibitors; bile acid sequestrants; LDL receptor inducers; platelet aggregation inhibitors such as flycoprotein IIb/IIIa fibrinogen receptor antagonists and aspirin; vitamin B6 and pharmaceutically acceptable salts thereof; vitamine B12; folic acid or a pharmaceutically acceptable salt or ester thereof; antioxidant viramins such as C and E and beta carotene; beta blockers; angiotensin II antagonists such as losartan; antiotensin converting enzyme inhibitors such as enalapril and captopril; calcium channel blockers such as nifedipine and diltiazam; endothelian antagonists; agents other than LXR ligands that enhance ABC1 gene expression; and bisphosphonate compounds such as alendronate sodium.

The methods and uses employing these combinations may comprise the administration of the compound of formula (I) and the other therapeutic agent either sequentially in any order or simultaneously in separate or combined pharmaceutical compositions. When combined in the same composition it will be appreciated that the two compounds must be stable and compatible with each other and the other components of the composition and may be formulated for administration. When formulated separately they may be provided in any convenient formulation, in such a manner as are known for such compounds in the art.

When a compound of formula (I) is used in combination with another therapeutic agent, the dose of each compound may differ from that when the compound is used alone. Appropriate doses will be readily appreciated by those skilled in the art. The appropriate dose of the compound(s) of formula (I) and the other therapeutically active agent(s) and the relative timings of administration will be selected in order to achieve the desired combined therapeutic effect, and are in the within the expertise and discretion of the attendent clinician.

Compounds of the invention can be made according to any suitable method of organic chemistry. According to one method, a compound of formula (I) is prepared using the process depicted in Scheme 1, below.

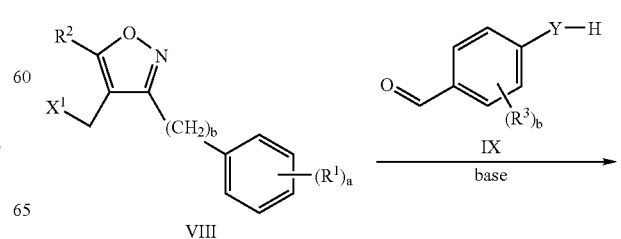

Scheme I

-continued

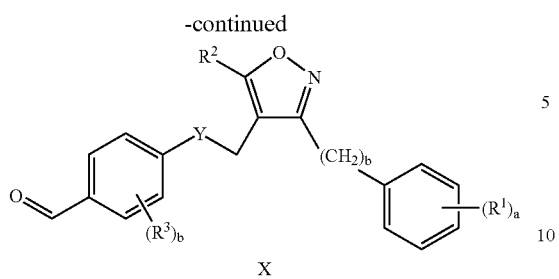

X

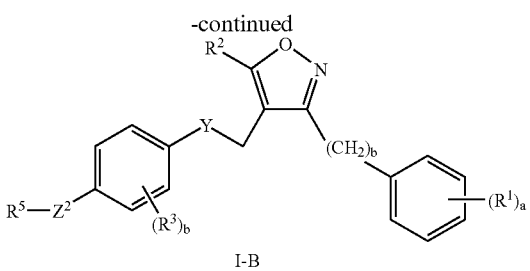

I-B wherein:

$X^1$ is halo;

$Z^1$ is —O—, —S(O)$_f$— or —N(R$^8$)—;

$Z^2$ is —R$^4$—O—;

E is a suitable electrophile of formula R$^5$—R$^4$—; and all other variables are as defined above in connection with the description of compounds of formula (I).

In general, the process of Path A comprises the steps of:

a) reacting a compound of formula (VIII) with a compound of formula (IX) to prepare a compound of formula (X);

b) reducing the compound of formula (X) followed by chlorination to prepare a compound of formula (XI);

c) reacting the compound of formula (XI) with a compound of formula (XII) to prepare a compound of formula (I-A).

More particularly, a compound of formula (I) is prepared by reacting the compound of formula (XI) with a compound of formula (XII) in the presence of a suitable base such as potassium carbonate in a polar aprotic solvent such as N,N-dimethylformamide at ambient temperature.

Optionally, the reaction step may further comprise removing protecting groups to prepare the compounds of formula (I-A). Such deprotection steps may be carried out using techniques well known to those skilled in the art. The compounds of formula (XII) are commercially available or may be prepared using techniques conventional in the art.

The compound of formula (XI) may be prepared by reducing the compound of formula (X) followed by chlorination. The carbonyl functionality of the compound of formula (X) may be reduced using conventional reducing agents such as sodium borohydride, or the like, in a suitable solvent such as methanol, typically at ambient temperature. Chlorination of the resulting alcohol can be achieved by reaction with a chlorine source, such as thionyl chloride, in a suitable solvent such as dichloromethane at ambient temperature.

The process for preparing the compound of formula (X) is described below.

In general, the process of Path B comprises the steps of:

a) reacting a compound of formula (VIII) with a compound of formula (IX) to prepare a compound of formula (X);

b) rearranging the carbonyl functionality of the compound of formula (X) followed by hydrolysis to prepare a compound of formula (XII); and c) reacting the compound of formula (XIII) with a suitable electrophile to to prepare a compound of formula (I-B).

Path A

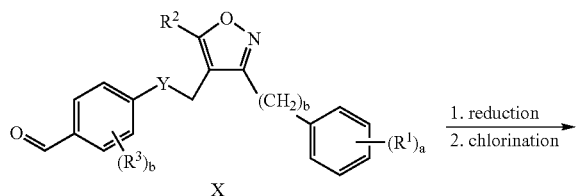

X 1. reduction
2. chlorination

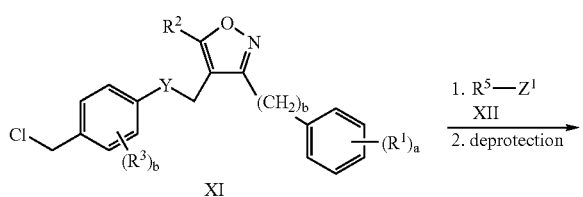

XI

1. R$^5$—Z$^1$
   XII
2. deprotection

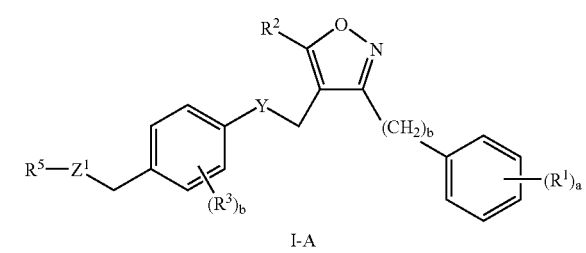

I-A

Path B

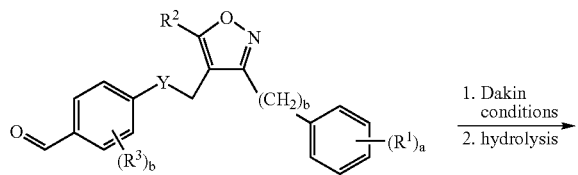

X

1. Dakin conditions
2. hydrolysis

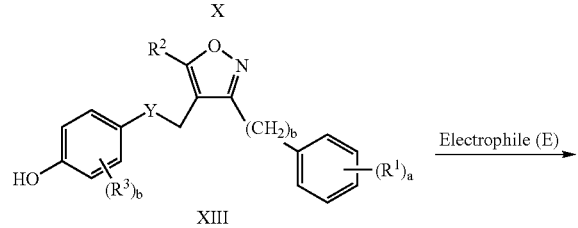

XIII

Electrophile (E)

More particularly, a compound of formula (I) is prepared by treating the compound of formula (XIII) with with a suitable base such as potassium carbonate, in the prescence of a suitable electrophile of formula $R^5$—$R^4$—, in a polar aprotic solvent such as acetone or N,N-dimethylformamide. The choice of suitable electrophiles will depend upon the particular compound of formula (I) that is desired and is within the skill of those in the art. Reagents capable of providing electrophiles suitable for this reaction are commercially available.

Optionally, the reaction step may further comprise removing protecting groups to prepare the compounds of formula (I-B), such as for example where the electrophile contains a protected functionality. Such deprotection steps may be carried out using techniques well known to those skilled in the art.

The compound of formula (XIII) may be prepared by rearranging the carbonyl functionality of the compound of formula (X) followed by hydrolysis, according to the methods described in Leffler, J. E., *Chemistry Reviews* 45:385 (1949). Typically, the rearrangement of the carbonyl functionality is carried out under Dakin conditions. The resulting formate group is then hydrolized to prepare the compound of formula (XIII).

The compound of formula (X) from which both compounds of formula (I-A) and compounds of formula (I-B) are prepared, may be prepared by reacting a nucleophile of formula (IX) with a compound of formula (VIII) in the prescence of a suitable base such as potassium carbonate, in a polar aprotic solvent such asacetone or N,N-dimethylformamide, at ambient temperature. Nucleophiles of formula (IX) are commercially available or may be prepared using techniques conventional in the art.

The compound of formula (VIII) may be prepared by halogenating a compound of formula (VI).

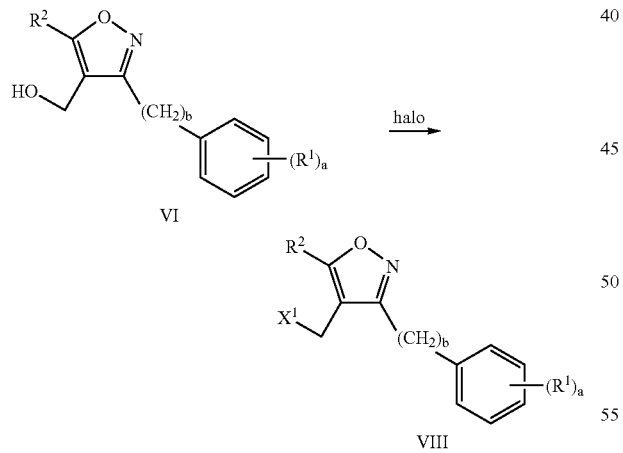

wherein $X^1$ is halo; more particularly chloro; and all other variables are as defined in connection with compounds of formula (I).

Any suitable halogenating reagent conventional in the art may be employed in the instant reaction. Examples of suitable halogenating reagents include but are not, limited to thionyl chloride and triphenylphosphine dichloride. The reaction is typically carried out in a non-polar solvent such as dichloromethane at ambient temperature.

The compound of formula (VI) is prepared by reducing a compound of formula (V).

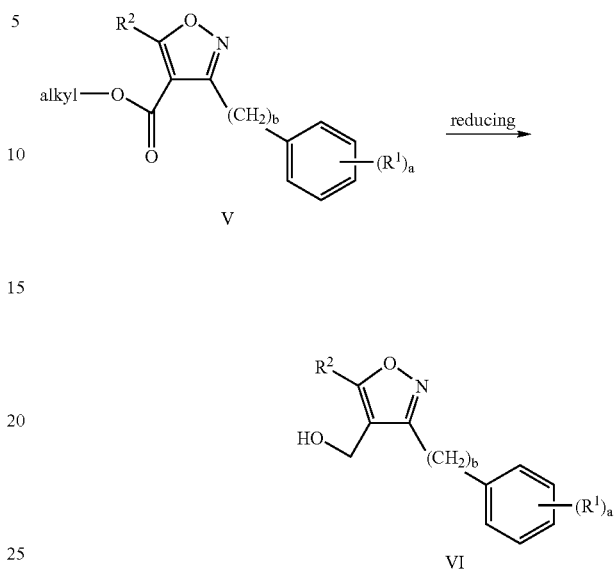

A compound of formula (V) may be treated with a reducing agent such as diisobutyl aluminum hydride, in a suitable solvent such as tetrahydrofuran.

The compound of formula (V) is prepared by chlorinating a compound of formula (III) followed by reaction with an ester of formula (IV) and cyclizing to prepare the compound of formula (V).

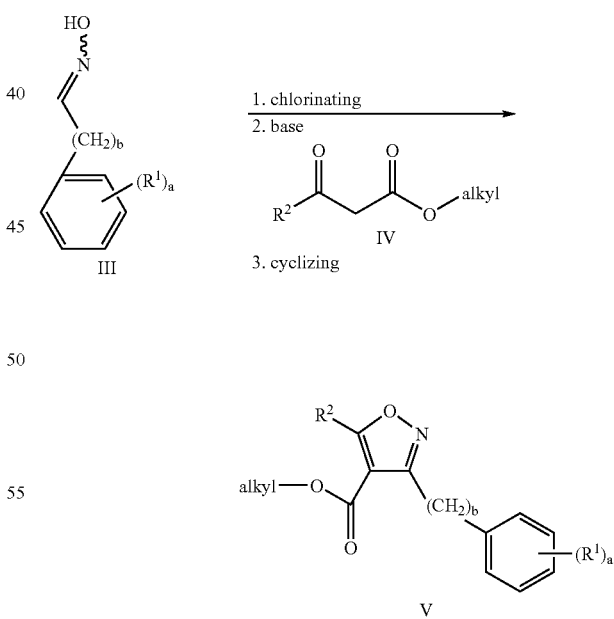

The process is conveniently carried out according to the method described by Doyle, H. P., et. al., *Journal of the Chemical Society* Part V:5838 (1963). Esters of formula (IV) are commercially available or can be prepared using conventional techniques.

The compound of formula (III) is prepared by condensing a compound of formula (II) with hydroxylamine.

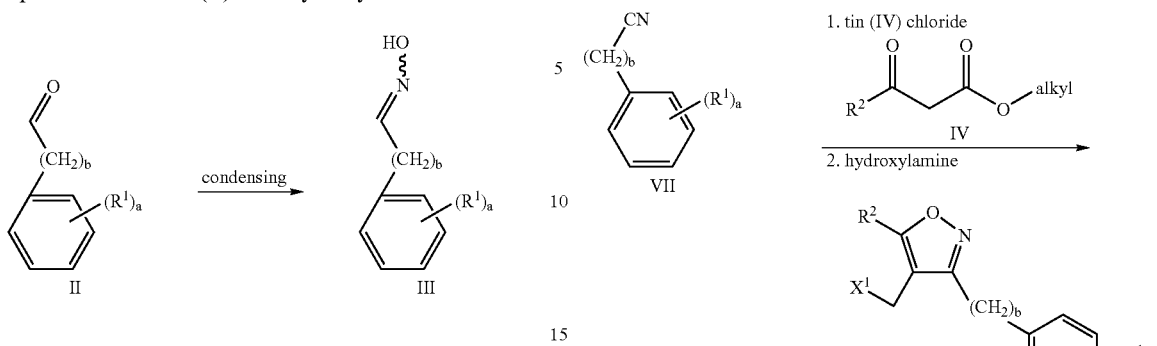

Alternatively, a compound of formula (VIII) may be prepared by reacting a compound of formula (VII) with tin chloride in the presence of a compound of formula (I) followed by hydroxylamine, according to the method described in Singh, B., Lesher, G. Y., *Synthesis*, November 1978.

In another embodiment, a compound of formula (I) is prepared according to the process depicted in Scheme 2 below.

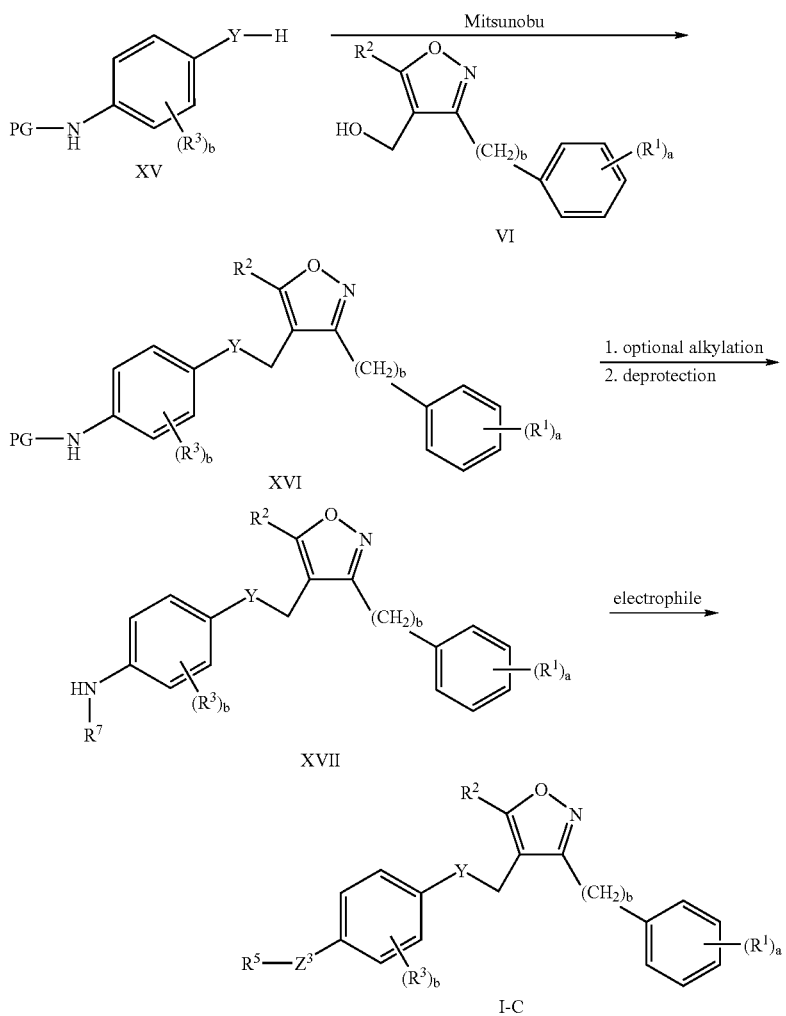

wherein:
PG is a suitable protecting group;
$Z^3$ is selected from the group consisting of —$R^4O$—, —$R^4$—$S(O)_r$—, —$R^4$—$N(R^8)$—, —$CON(R^8)$—, —$C(O)R^4N(R^8)$—, —$S(O)_rN(R^8$— and —$S(O)_rR^4N(R^8)$—; and
all other variables are as defined above in connection with the description of compounds of formula (I).

In general, the process comprises the steps of:
a) reacting a protected compound of formula (XV) with a compound of formula (VI) to prepare a compound of formula (XV));
b) optionally alkylating the compound of formula (XVI), followed by deprotecting the compound of formula (XVI) to prepare a compound of formula (XVII); and
c) reacting the compound of formula (XVII) with a suitable electrophile to prepare a compound of formula (I-C).

More particularly, a compound of formula (I) is prepared by reacting the compound of formula (XVII) with a suitable electrophile. Suitable electrophiles for reaction with the compound of formula (XVII) will be apparent to those skilled in the art. Examples of suitable electrophiles include but are not limited to activated carboxylic acids, sulfonyl halides and alkyl halides. In certain embodiments, it may be advantageous to employ electrophiles having protected functionalities. In such embodiments, the compounds of formula (XVII) may be obtained by carrying out a further deprotecting step to remove the protecting group.

In embodiments wherein the electrophile is derived from a carboxylic acid, the carboxylic acid is typically activated by treatment with a suitable coupling reagent such as a carbodiimide derivative. Reaction of a suitable activated carboxylic acid derivative with a compound of formula (XVII) in dichloromethane at ambient temperature provides a compound of formula (I-C). A compound of formula (I-C) in which the electrophile is derived from a sulfonyl chloride are prepared by reaction of the sulfonyl chloride with a compound of formula (XVII) in the presence of a base such as pyridine or triethylamine, in a solvent such as dioxane, at ambient temperature. A compound of formula (I-C) in which the electrophile is derived from an alkyl halide are prepared by reacting the alkyl halide with a compound of formula (XVIII) in the peresence of a suitable base such as potassium carbonate, in a polar aprotic solvent such as N,N-dimethylformamide, at ambient temperature.

The compound of formula (XVII) is prepared by optionally alkylating the compound of formula (XVI), followed by deprotecting (i.e., removing the protecting group (PG)).

The optional alkylation step is typically carried out in the presence of a strong base such as sodium hydride or the like. Conventional techniques for deprotecting the compound of formula (XVI) or the alkylated compound of formula (XVI) may be employed.

The compound of formula (XVI) is prepared by reacting the protected compound of formula (XV) with a compound of formula (VI). Typically, the reaction of the protected compound of formula (XV) with the compound of formula (VI) is carried out under Mitsunobu conditions. The compound of formula (VI) may be prepared by the methods described above.

The protected compound of formula (XV) may be prepared using conventional techniques for the introduction of a conventional protecting group. Suitable protecting groups include but are not limited to tert-butyloxycarbonyl. The compounds of formula (XV) are commercially available or may be prepared using techniques conventional in the art.

Other general conversion techniques are known in the art for derivatizing an organic compound. Such techniques may be applied to the compounds of formula (I) for the purposes of converting a compound of formula (I) to a different compound of formula (I), and as such they are contemplated by the present invention.

The following examples are intended for illustration only and are not intended to limit the scope of the invention in any way, the present invention being defined by the claims.

In the examples, the following terms have the designated meaning: "h" means hour(s); "N" means normal; "M" means molar; "µM" means micromolar; "mM" means millimolar; "µmol" means micromoles; "mmol" means millimoles; "g" means grams; "mg" means milligrams; "µL" means microliters; and "mL" means milliliter.

EXAMPLES

General Synthesis of Isoxazoles a) 2,6-Dichlorobenzaldehyde oxime

A solution of 2,6-dichlorobenzaldehyde (25 g, 0.14 mole) in ethanol (200 mL) was added to a solution of hydroxylamine hydrochloride (11 g, 0.16 mole) and sodium hydroxide (6.3 g, 0.16 mole) in water (100 mL). The resulting mixture was stirred at 90° C. for 24 hours. The volume was reduced in vacuo by ca 30 mL which induced a precipitate. The flask was then cooled to room temperature and the white solids were collected by filtration and washed with water (2×100 mL). Yield =25.9 g. (96%) of 2,6-dichlorobenzaldehyde oxime.

b) Methyl 3-(2,6-dichlorophenyl)-5-isopropylisoxazole-4carboxylate

A solution of 2,6-dichlorobenzaldehyde oxime (19.8 g, 0.104 mol) in N,N-dimethyl formamide (80 mL) was placed in an ambient temperature water bath and was treated with N-chlorosuccinimide (13.9 g, 0.104 mole). Following dissolution, an exotherm was observed along with a color change to dark yellow. The reaction was stirred an additional hour then the contents were then poured into water (200 mL) and the product extracted with diethyl ether (300 mL). The ethereal layer was washed with water (3×100 mL) and brine (50 mL), then dried over anhydrous magnesium sulfate. After filtering, the solvent was removed in vacuo to yield a yellow oil which was used in the next step without further purification. Separately, a solution of methyl isobutyryl acetate (18 g, 0.125 mol) in tetrahydrofuran (25 mL) at 0° C. was treated with a solution of sodium methoxide (250 mL, 0.5 M in methanol). A solution of the above crude 2,6-dichloro-N-hydroxybenzenecarboximidoyl chloride in tetrahydrofuran (80 mL) was then added dropwise. After stirring at ambient temperature for 16 h the solvent was removed in vacuo. The residue was triturated with water (250 mL) and the resulting solids filtered and washed with water. Yield=22.7 g. (69%) of methyl 3-(2,6-dichlorophenyl)-5-isopropylisoxazole-4-carboxylate.

c) [3-(2,6-Dichlorophenyl)-5-isopropylisoxazol-4-yl]methanol

A solution of 3-(2,6-dichlorophenyl)-4-carbomethoxy-5-isopropyl-isoxazole (8.4 g, 27 mmol) in tetrahydrofuran (60 mL) was cooled to 0° C. under a nitrogen atmosphere while a solution of diisobutylaluminum hydride (38 mL, 1.5M in toluene) was added dropwise. The reaction was allowed to warm slowly to ambient temperature over several hours and stirred at room temperature for 16 h total. The flask was again cooled to 0° C. and methanol (2 mL) was carefully added over a 10 minute period. Water (20 mL) was added dropwise and a gelatinous mixture formed. Sodium hydroxide (30 mL, 2N) was added and the material was filtered over a plug of celite. After the solids were nearly dry, they were extracted with ethyl acetate (4×50 mL) and the filtrates were combined. The organic layer was washed with water (2×50 mL), brine (50 mL), was dried over anhydrous magnesium sulfate, filtered and condensed to a white crystalline solid. Yield=7.1 g. (93%) of [3-(2,6-dichlorophenyl)-5-isopropylisoxazol-4-yl]methanol.

d) 4-(Chloromethyl)-3-(2,6-dichlorophenyl)-5-isopropylisoxazole

A solution of [3-(2,6-dichlorophenyl)-5-isopropylisoxazol-4-yl]methanol (15.2 g, 53.1 mmol) in dichloromethane (50 mL) was treated with thionyl chloride (40.0 mL, 54.8 mmol). The reaction was stirred for 1 hour once vigorous bubbling ceased. The solvent and excess reagent were removed in vacuo. Yield=15.96 g. (99%) of 4 (chloromethyl)-3-(2,6-dichlorophenyl)-5-isopropylisoxazole.

Example 1

3-{[(4-{[3-(2,6-Dichlorophenyl)-5-isopropylisoxazol-4-yl]methoxy}-2-methylphenyl)(methyl)amino]methyl}benzoic acid

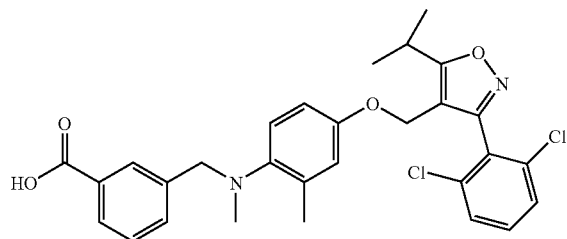

a) tert-Butyl 4-hydroxy-2-methylphenylcarbamate

A solution of 4-amino-3-methylphenol (3.0 g, 24 mmol) in tetrahydrofuran (30 mL) was stirred with di-tert-butyldicarbonate (5.32 g, 24 mmol) for 24 hours at ambient temperature. The solvent was evaporated and the resulting residue was partitioned in diethyl ether and aqueous sodium hydrogensulfate. The organic layer was washed with water (2×50 mL), brine (50 mL), dried over anhydrous magnesium sulfate, filtered and condensed to a residue. Yield=5.4 g. (99%) of tert-butyl 4hydroxy-2-methylphenylcarbamate.

b) tert-Butyl -{[3-(2,6-dichlorophenyl)-5-isopropylisoxazol-4-yl]methoxy}-2-methylphenylcarbamate A solution of tert-butyl 4-hydroxy-2-methylphenylcarbamate (3.0 g, 13.4 mmol), triphenylphosphine (3.53 g, 13.4 mmol), and [3-(2,6-dichlorophenyl)-5-isopropylisoxazol-4-yl]methanol (3.85 g, 13.4 mmol) in dichloromethane (40 mL) at 0° C. was treated with a solution of diisopropylazidodicarboxylate (2.65 mL, 13.4 mmol) in dichloromethane (10 mL) dropwise. The reaction was allowed to stir at 0° C. for 30 minutes, then warmed to ambient temperature for 1 h after which time the solvent was removed in vacuo. The resulting oil was chromatographed on silica gel eluting with 20% ethyl acetate/hexanes. Yield=4.34 g (66%) of tert-butyl 4-{[3-(2,6-dichlorophenyl)-5-isopropylisoxazol-4-yl]methoxy}-2-methylphenylcarbamate.

c) tert-Butyl 4-{[3-(2,6-dichlorophenyl)-5-isopropylisoxazol-4-yl]methoxy}-2-methylphenyl-(methyl)carbamate A solution of tert-butyl 4-{[3-(2,6-dichlorophenyl)-5-isopropylisoxazol-4-yl]methoxy}-2-methylphenylcarbamate (1.23 g, 2.5 mmol) in dimethoxyethane (5 mL) at 0° C. was treated with lithium(bis)trimethylsilylamide (2.6 mL, 2.6 mmol) as a 1.0 molar solution in tetrahydrofuran. After 2 minutes, iodomethane (0.5 mL, 8.1 mmol) was added and the reaction was stirred for 1 h. The reaction was then partitioned with ethyl acetate and aqueous sodium hydrogensulfate. The organic layer was washed with water (2×50 mL), brine (50 mL), dried over anhydrous magnesium sulfate, filtered and condensed to a residue. Yield=1.26 g. (100%) of tert-butyl 4-{[3-(2,6-dichlorophenyl)-5-isopropylisoxazol-4-yl]methoxy}-2-methylphenyl-(methyl)carbamate.

d) N-(4-{[3-(2,6-Dichlorophenyl)-5-isopropylisoxazol-4-yl]methoxy}-2-methylphenyl)-N-methylamine A solution of tert-butyl 4-{[3-(2,6-dichlorophenyl)-5-isopropylisoxazol-4-yl]methoxy}-2-methylphenyl(methyl)carbamate (1.2 g, 2.37 mmol) in dichloromethane (15 mL) was treated with trifluoroacetic acid (1 mL, 13 mmol) and stirred at ambient temperature for 18 h. The solvent was removed in vacuo and the resulting residue was partitioned in ethylacetate and aqueous sodium bicarbonate. The organic layer was washed with brine (50 mL) and was dried over anhydrous magnesium sulfate, filtered, and condensed to a residue. Yield=0.96 g. (100%) of N-(4-{[3-(2,6-dichlorophenyl)-5-isopropylisoxazol-4-yl]methoxy}-2-methyl phenyl)-N-methylamine.

e) Methyl 3-{[(4-{[3-(2,6-dichlorophenyl)-5-isopropylisoxazol-4-yl]methoxy}-2-methylphenyl)(methyl)amino]methyl}benzoate A solution of N-(4-{[3-(2,6-dichlorophenyl)-5-isopropylisoxazol-4-yl]methoxy}-2-methylphenyl)-N-methylamine (0.45 g, 1.1 mmol) in dimethylformamide (4 mL) was treated with potassium carbonate (0.15 g, 1.1 mmol) followed by methyl 3-(bromomethyl)benzoate (0.25 g, 1.1 mmol). After stirring at ambient temperature for 24 h, the reaction was partitioned with ethyl acetate and water. The organic layer was washed with water (2×50 mL), brine (50 mL), dried over anhydrous magnesium sulfate, filtered and condensed to a residue which was chromatographed on silica gel eluting with 20% ethyl acetate/hexanes. Yield=0.43 g. (70%) of methyl 3-{[(4-{[3-(2,6-dichlorophenyl)-5-isopropylisoxazol-4-yl]methoxy}-2-methylphenyl)(methyl)-amino]methyl}benzoate.

f) 3-{[(4-{[3-(2,6-Dichlorophenyl)-5-isopropylisoxazol-4-yl]methoxy}-2-methylphenyl)(methyl)amino]methyl}benzoic acid A solution of methyl 3-{[(4-{[3-(2,6-dichlorophenyl)-5-isopropylisoxazol-4-yl]methoxy}-2-methylphenyl)(methyl)amino]methyl}benzoate (0.42 g, 0.76 mmol) in tetrahydrofuran (4 mL) was stirred vigorously with aqueous lithium hydroxide (2.3 ml, 0.4 M) at ambient temperature for 24 hours. The reaction was concentrated and the aqueous residue was partitioned with ethyl acetate and aqueous sodium hydrogensulfate. The organic layer was washed with brine (50 mL) and was dried over anhydrous magnesium sulfate, filtered, and condensed to a residue which was chromatographed on silica gel eluting with 10% methanol/dichloromethane. Yield=0.12 g. (30%) of 3-{[(4-{[3-(2,6-dichlorophenyl)-5-isopropylisoxazol-4-yl]methoxy}-2-methylphenyl)(methyl)amino]methyl}benzoic acid. $^1$H NMR (CDCl$_3$, 400 MHz) δ 8.02 (s, 1H), 7.91 (d, 1H), 7.55 (d, 1H), 7.38 (m 3H), 7.31 (m, 1H), 6.95 (d, 1H), 6.33 (m, 1H), 6.57 (dd, 1H), 4.67 (s, 2H), 3.97 (s, 2H), 3.91 (s, 3H), 3.31 (m, 1H), 2.49 (s, 3H), 2.33 (s, 3H), 1.40 (d, 6H); MS (ESP+) m/e 539 (MH+).

Example 2

Methyl 4-[(4-{[3-(2,6-dichlorophenyl)-5-isopropyl-4-isoxazolyl]methoxy}-2-dimethylanilino)methyl]benzoate.

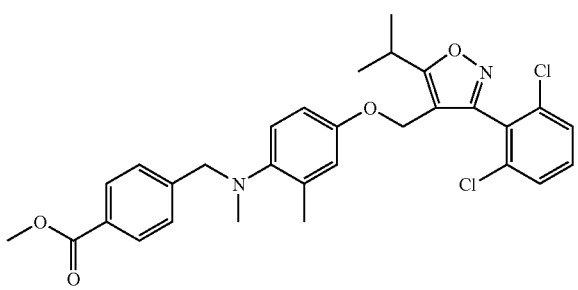

The title compound was prepared from appropriate starting materials using the synthesis described in Example 1.

$^1$HNMR (CDCl$_3$, 400 MHz) δ 7.97 (d, 2H, J=7.99), 7.40 (m, 4H), 7.31 (m, 1H), 6.93 (d, 1H), J=8.67), 6.62 (d, 1H, J=3.06), 6.56 (dd, 1H, J=8.84), 4.66 (s, 2H), 3.98 (s, 2H), 3.90 (s, 3H), 3.31 (m, 1H), 2.50 (s, 3H), 2.31 (s, 3H), 1.40 (d, 6H, J=6.93); MS (ESP+) m/e 553 (M).

Example 3

3-{[(2-Chloro-4-{[3-(2,6-dichlorophenyl)-5-isopropylisoxazol-4-yl]methoxy}phenyl)amino]methyl}benzoic acid

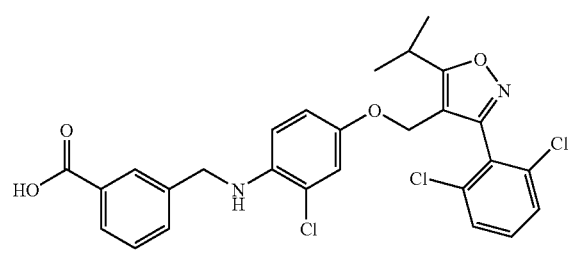

The title compound was prepared from appropriate starting materials using the synthesis described in Example 1.

$^1$H NMR (CDCl$_3$ 400 MHz) δ 8.04 (s, 1H), 7.97 (d, 1H), 7.53 (d, 1H), 7.38 (m, 3H), 7.29 (m, 1H), 6.75 (d, 1H), 6.52 (dd, 1H), 6.40 (d, 1H), 4.61 (s, 2H), 4.35 (s, 2H), (d, 6H); MS (ESP+) m/e 545 (MH$^{30}$).

Example 4

5-[(4-{[3-(2,6-Dichlorophenyl)-5-isopropyl-4-isoxazolyl]methoxy}-2-dimethylanilino)methyl]-2-furoic acid

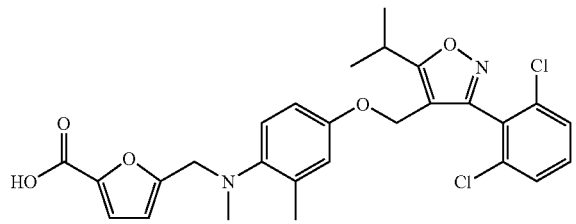

The title compound was prepared from appropriate starting materials using the synthesis described in Example 1.

$^1$HNMR (CDCl$_3$, 400 MHz) δ 7.38 (m, 2H), 7.30 (m, 1H) 7.17 (d, 1H, J=3.43), 6.88 (d, 1H, J=8.56), 6.60 (d, 1H, J=2.90), 6.54 (dd, 1H, J=8.55), 6.24 (d, 1H, J=3.37), 4.66 (s, 2H), 3.99 (s, 2H), 3.30 (m, 1H), 2.62 (s, 3H), 2.26 (s, 3H), 1.39 (d, 6H, J=7.09); MS (ESP+) m/e 529 (M).

Example 5

4-[(4-{[3-(2,6-Dichlorophenyl)-5-isopropyl-4-isoxazolyl]methoxy}-2-dimethylanilino)methyl]benzoic acid

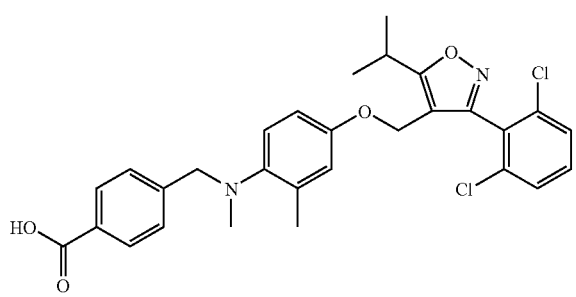

The title compound was prepared from appropriate starting materials using the synthesis described in Example 1.

$^1$HNMR (CDCl$_3$, 400 MHz) δ 8.04 (d, 2H, J=8.48), 7.45 (d, 2H, J=8.25), 7.39 (m, 2H), 7.31 (m, 1H), 6.94 (d, 1H, J=8.60), 6.62 (d, 1H, J=2.75), 6.57 (dd, 1H, J=8.71), 4.67 (s, 2H), 4.01 (S, 2H), 3.31 (m, 1H), 2.52 (s, 3H), 2.32 (s, 3H), 1.40 (d, 6H, J=6.99); MS (ESP+) m/e 539 (M).

Example 6

Methyl 2-[(4-{[3-(2,6-dichlorophenyl)-5-isopropyl-4-isoxazolyl]methoxy}-2-dimethylanilino)methyl]-3-furoate

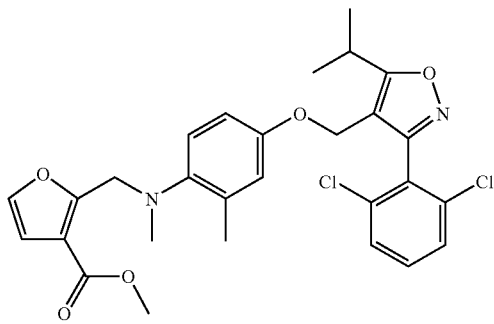

The title compound was prepared from appropriate starting materials using the synthesis described in Example 1.

¹HNMR (CDCl₃, 400 MHz) δ 7.39 (m, 2H), 7.31 (m, 2H), 6.87 (d, 1H, J=8.65), 6.63 (d, 1H), J=1.91), 6.59 (d, 1H, J=2.87), 6.52 (dd,1H, J=8.74), 4.65 (s, 2H), 4.28 (s,2H3.73 (s, 3H), 3.31 (m, 1H), 2.63 (s, 3H), 2.29 (s, 3H), 1.40 (d, 6H, J=6.91); MS (ESP+) m/e 543 (M).

Example 7

N-(2,1,3-Benzoxadiazol-5-ylmethyl)-4-{[3-(2,6-dichlorophenyl)-5-isopropyl-4-isoxazolyl]methoxy}-N,2-dimethylaniline

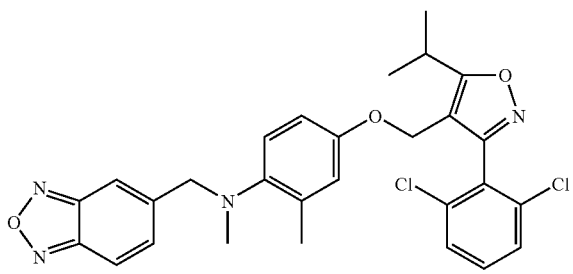

The title compound was prepared from appropriate starting materials using the synthesis described in Example 1.

¹HNMR (CDCl₃, 400 MHz) δ 7.75 (m, 2H), 7.46 (dd, 1H, J=9.29), 7.39 (m, 2H), 7.31 (m, 1H), 6.99 (d, 1H, J=8.63), 6.60 (m, 2H), 4.67 (s, 2H), 4.03 (s, 2H), 3.31 (m, 1H), 2.56 (s, 3H), 2.31 (s, 3H), 1.40 (d, 6H, J=7.05); MS (ESP+) m/e 522 (M-CH₃)

Example 8

N-(4-{[3-(2,6-Dichlorophenyl)-5-isopropyl-4-isoxazolyl]methoxy}-2-methylphenyl)-N-methyl-N-[4-(1,2,3-thiadiazol-4-yl)benzyl]amine

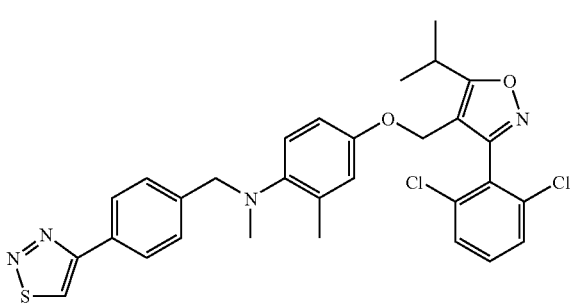

The title compound was prepared from appropriate starting materials using the synthesis described in Example 1.

¹HNMR (CDCl₃, 400 MHz) δ 8.62 (s,1H), 7.98 (d, 2H, J=8.31), 7.48 (d, 2H, J=8.48), 7.39 (m, 2H), 7.31 (m, 1H), 6.96 (d, 1H, J=8.64), 6.63 (d, 1H, J=2.93), 6.58 (dd, 1H, J=8.80), 4.67 (s, 2H), 4.00 (s, 2H), 3.32 (m, 1H), 2.54 (s, 3H), 2.34 (s, 3H) 1.40 (d, 6H, J=7.05); MS (ESP+) m/e 579 (M).

Example 9

4-[(4-{[3-(2,6-Dichlorophenyl)-5-isopropyl-4-isoxazolyl]methoxy}-2-dimethylanilino)methyl]benzonitrile

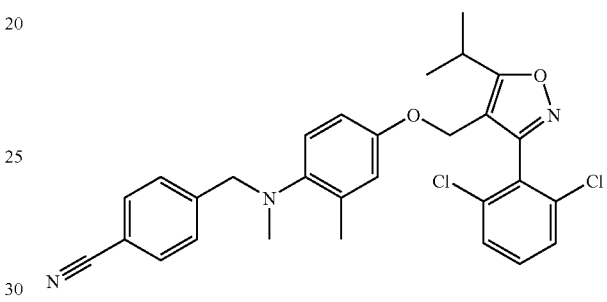

The title compound was prepared from appropriate starting materials using the synthesis described in Example 1.

¹HNMR (CDCl₃, 400 MHz) δ 7.59 (d, 2H, J=8.12), 7.45 (d, 2H,.J=8.13), 7.39 (m, 2H), 7.31 (m, 1H), 6.92 (d, 1H, J=8.62), 6.62 (d, 1H, J=3.04), 6.57 (dd, 1H, J=3.99 (s, 2H), 3.30 (m, 1H), 2.50 (s, 3H), 2.29 (s, 3H), 1.39 (d, 6H, J=7.06).

Example 10

2-[(4-{[3-(2,6-Dichlorophenyl)-5-isopropyl-4-isoxazolyl]methoxy}-2-dimethylanilino)methyl]-3-furoic acid

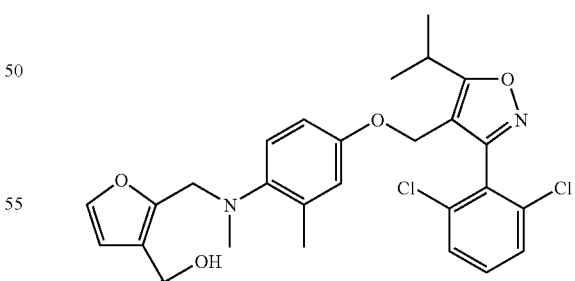

The title compound was prepared from appropriate starting materials using the synthesis described in Example 1.

¹HNMR (CDCl₃, 400 MHz) δ 7.36 (m, 2H), 7.28 (m, 1H), 7.21 (s,1H), 6.97 (d, 1H, J=8.59), 6.72 (s, 1H), 6.56 (m, 2H), 4.66 (s, 2H), 4.25 (s, 2H), 3.28 (m, 1H), 2.58 (s, 3H), 2.26 (s, 3H), 1.38 (d, 6H, J=7.07); MS (ESP+) m/e 529 (M).

Example 11

{3-[(4-{[3-(2,6-Dichlorophenyl)-5-isopropyl-4-isoxazolyl]methoxy}-2-dimethylanilino)methyl]phenyl}methanol

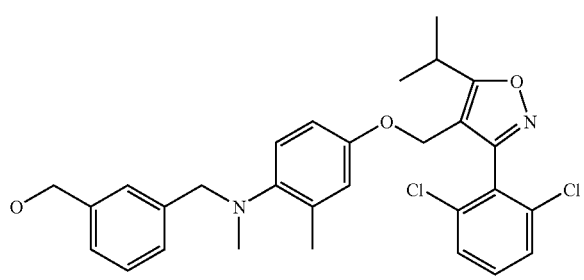

The title compound was prepared from appropriate starting materials using the synthesis described in Example 1.

¹HNMR (CDCl₃, 400 MHz) δ 7.39 (m, 2H), 7.32 (m, 4H), 7.24 (m, 1H), 6.95 (d, 1H, J=8.69), 6.60 (m, 2H), 4.67 (s, 4H), 3.92 (s, 2H), 3.32 (m, 1H), 2.50 (s, 3H), 2.33 (s, 3H), 1.40 (d, 6H, J=6.93); MS (ESP+) m/e 525 (M).

Example 12

{4-[(4-{[3-(2,6-Dichlorophenyl)-5-isopropyl-4-isoxazolyl]methoxy}-2-dimethylanilino)methyl]phenyl}methanol

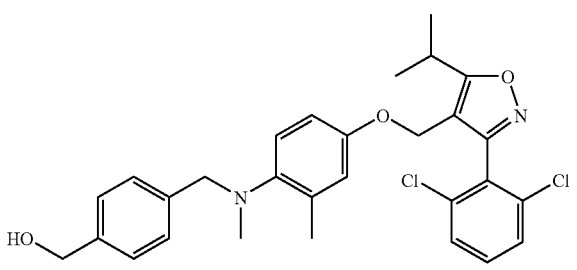

The title compound was prepared from appropriate starting materials using the synthesis described in Example 1.

¹HNMR (CDCl₃, 400 MHz) δ 7.39 (m, 2H), 7.32 (m, 5H), 6.94 (d, 1H, J=8.63), 6.60 (m, 2H), 4.67 (s, 4H), 3.92 (s, 2H), 3.31 (m, 1H), 2.50 (s, 3H), 2.32 (s, 3H), 1.40 (d, 6H, J=7.09); MS (ESP+) m/e 525 (M).

Example 13

3-[(4-{[3-(2,6-Dichlorobenzyl)-5-ethyl-4-isoxazolyl]methoxy}-2-dimethylanilino)methyl]benzoic acid

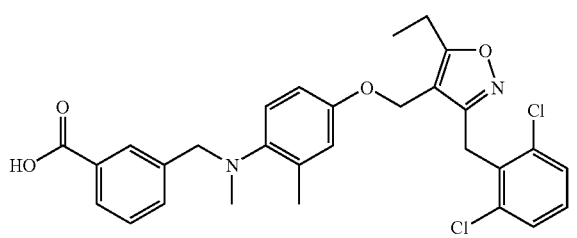

The title compound was prepared from appropriate starting materials using the synthesis described in Example 1.

¹HNMR (CDCl₃, 400 MHz) δ 8.11 (s,1H), 7.99 (d,1H, J=7.75), 7.63 (d, 1H, J=7.65), 7.42 (t, 1H, J=7.76), 7.27 (m, 2H), 7.07 (m, 2H), 6.75 (m, 2H), 4.79 (s, 2H), 4.32 (s, 2H), 4.04 (s, 2H), 2.75 (m, 2H), 2.56 (s, 3H), 2.40 (s, 3H), 1.25 (m, 3H); MS (ESP+) m/e 539 (M).

Example 14

3-{[(4-{[5-Isopropyl-3-(2,4,6-trichlorophenyl)isoxazol-4-yl]methoxy}-2-methylphenyl)-(methyl)amino]methyl}benzoic acid

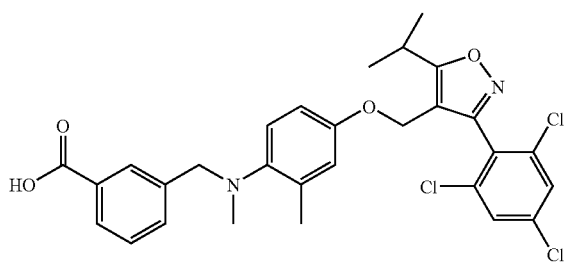

The title compound was prepared from appropriate starting materials using the synthesis described in Example 1.

¹HNMR (CDCl₃, 400 MHz) δ 8.08 (s, 1H), 7.98 (d, 1H), 7.64-7.59 (m, 1H), 7.44-7.38 (m, 3H), 6.99-6.94 (m, 1H), 6.63-6.55 (m, 2H), 4.66 (s, 2H), 4.01 (s, 2H), 3.35-3.24 (m, 1H), 2.53 (s, 3H), 2.34 (s, 3H), 1.39 (d, 6H); MS (AP−) m/e 572 (M⁻).

Example 15

3-[(4-{[3-(2,6-Dichlorobenzyl)-5-isopropyl-4-isoxazolyl]methoxy}-2-dimethylanilino)methyl]benzoic acid

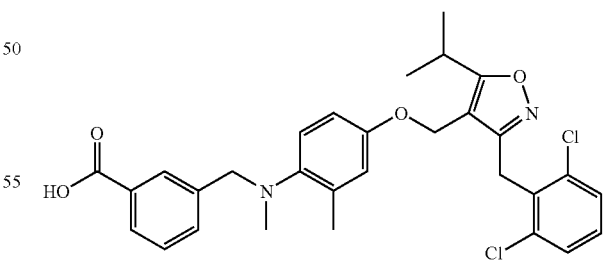

The title compound was prepared from appropriate starting materials using the synthesis described in Example 1.

¹HNMR (CDCl₃, 400 MHz) δ 8.11 (s, 1H), 7.99 (d, 1H, J=7.83), 7.64 (s, 1H), 7.43 (t, 1H), J=7.55), 7.28 (m, 2H), 7.07 (m, 2H), 6.75 (m, 2H), 4.81 (s, 2H), 4.31 (s, 2H), 4.05 (s, 2H), 3.16 (m, 1H), 2.57 (s, 3H), 2.40 (s, 3H), 1.29 (d, 6H, J=6.91); MS (ESP+) m/e 553 (M).

Example 16

3-{[(4-{[3-(2-Chlorobenzyl)-5-isopropylisoxazol-4-yl]methoxy}-2-methylphenyl)(methyl)-amino]methyl}benzoic acid

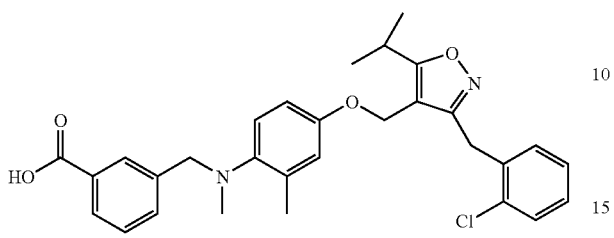

The title compound was prepared from appropriate starting materials using the synthesis described in Example 1.

$^1$HNMR (CDCl$_3$, 400 MHz) δ 8.12 (s, 1H), 8.01 (d, 1H), 7.63 (d, 1H), 7.43 (t, 1H), 7.35-7.31 (m, 1H), 7.23-7.12 (m, 3H), 7.03-6.98 (m, 1H), 6.70-6.66 (m, 1H), 6.65-6.60 (m, 1H), 4.64 (s, 2H), 4.17 (s, 2H), 4.04 (s, 2H), 3.23-3.12 (m, 1H), 2.55 (s, 3H), 2.37 (s, 2.37H), 1.31 (d, 6H); MS (AP+) m/e 520 (M+H$^+$).

Example 17

3-[(4-{[5-Cyclopropyl-3-(2,6-dichlorobenzyl)-4-isoxazolyl]methoxy}-2-dimethylanilino)methyl]benzoic acid

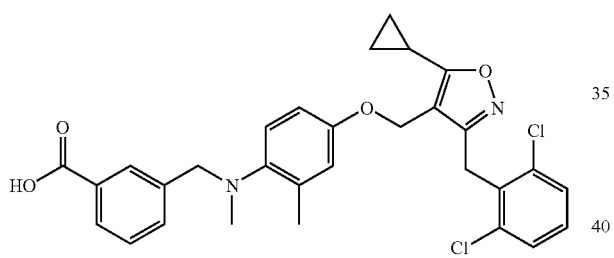

The title compound was prepared from appropriate starting materials using the synthesis described in Example 1.

$^1$HNMR (CDCl$_3$, 400 MHz) δ 8.11 (s, 1H), 7.99 (d, 1H, J=7.57), 7.64 (d, 1H, J=7.59), 7.43 (t, 1H, J=7.58), 7.27 (m, 2H), 7.08 (m, 2H), 6.78 (m, 2H), 4.88 (s, 2H), 4.30 (s, 2H), 4.05(s, 2H), 2.57 (s, 3H), 2.40 (s, 3H), 2.00 (m, 1H), 1.06 (m, 4H); MS (ESP+) m/e 553 (M).

Example 18

5-{[4-({5-Isopropyl-3-[2-(trifluoromethoxy)phenyl]-4-isoxazolyl}methoxy)-2-dimethylanilino]methyl}-2-furoic acid

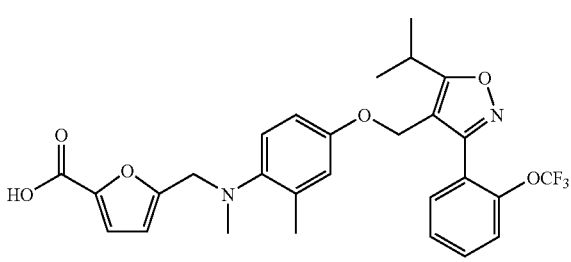

The title compound was prepared from appropriate starting materials using the synthesis described in Example 1.

$^1$HNMR (CDCl$_3$, 400 MHz) δ 7.58 (dd, 1H, J=8.10), 7.50 (m, 1H), 7.37 (m, 2H), 7.22 (d, 1H, J=3.46), 6.91 (d, 1H, J=8.49), 6.61 (d, 1H, J=3.02), 6.56 (dd, 1H, J=8.64), 6.29 (d, 1H, J=3.31), 4.73 (s, 2H), 4.03 (s, 2H), 3.30 (m, 1H), 2.65 (s, 3H), 2.28 (s, 3H), 1.38 (d, 6H, J=7.05); MS (ESP+) m/e 545 (M).

Example 19

4-{[4-({5-Isopropyl-3-[2-(trifluoromethoxy)phenyl]-4-isoxazolyl}methoxy)-2-dimethylanilino]methyl}benzoic acid

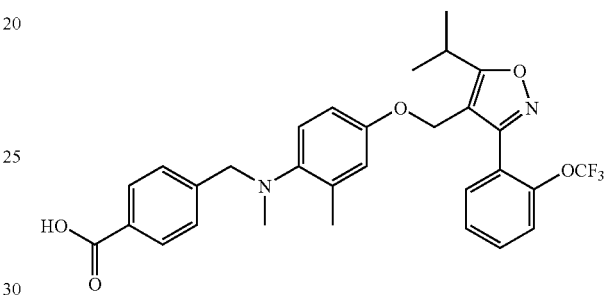

The title compound was prepared from appropriate starting materials using the synthesis described in Example 1.

$^1$HNMR (CDCl$_3$, 400 MHz) δ 8.04 (d, 2H, J=8.26), 7.57 (dd, 1H, J=7.84), 7.48 (m, 3H), 7.37 (m, 2H), 6.96 (d, 1H, J=8.68), 6.63 (d, 1H, J=2.83), 6.58 (dd, 1H, J=8.48), 4.73 (s, 2H), 4.02 (s, 2H), 3.30 (m, 1H), 2.54 (s, 3H), 2.32 (s, 3H), 1.39 (d, 6H, J=7.14);MS (ESP+) m/e 555 (M).

Example 20

3-{[4-({5-Isopropyl-3-[2-(trifluoromethoxy)phenyl]-4-isoxazolyl}methoxy)-2-dimethylanilino]methyl}benzoic acid

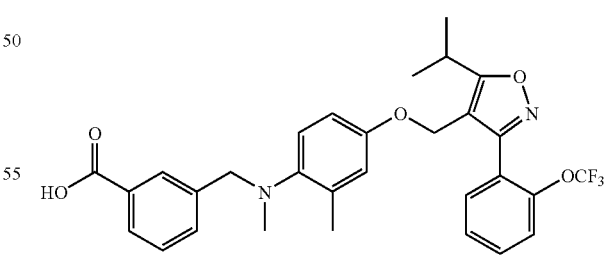

The title compound was prepared from appropriate starting materials using the synthesis described in Example 1.

$^1$HNMR (CDCl$_3$, 400 MHz) δ 8.10 (s, 1H), 7.99(d, 1H, J=7.82), 7.60 (m, 2H), 7.50 (m, 1H), 7.40 (m, 3H), 6.98 (d, 1H, J=8.53), 6.63 (d, 1H, J=2.78), 6.59 (dd, 1H, J=8.34), 4.74 (s, 2H), 4.01 (s, 2H), 3.31 (m, 1H), 2.52 (s, 3H), 2.33 (s, 3H), 1.39 (d, 6H, J=6.82), MS (ESP+) m/e 555 (M).

Example 21
Methyl 5-{[4-({5-isopropyl-3-[2-(trifluoromethoxy)phenyl]-4-isoxazolyl}methoxy)-2-dimethylanilino]methyl}-2-furoate

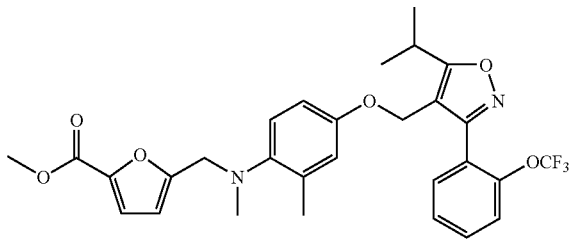

The title compound was prepared from appropriate starting materials using the synthesis described in Example 1.
$^1$HNMR (CDCl$_3$, 400 MHz) δ 7.57 (dd, 1H, J=8.05),7.50 (m, 1H), 7.37 (m, 2H), 7.10 (d, 1H, J=3.30), 6.91 (d, 1H, J=8.71), 6.61 (d, 1H, J=2.90), 6.56 (dd, 1H, J=8.71), 6.23 (d, 1H, J=3.57), 4.72 (s, 2H), 4.00 (s, 2H), 3.87 (s, 3H), 3.30 (m, 1H), 2.63 (s, 3H), 2.27 (s, 3H), 1.38 (d, 6H, J=6.89); MS (ESP+) m/e 559 (M).

Example 22
Methyl 4-{[4-({5-isopropyl-3-[2-(trifluoromethoxy)phenyl]-4-isoxazolyl}methoxy)-2-dimethylanilino]methyl}benzoate

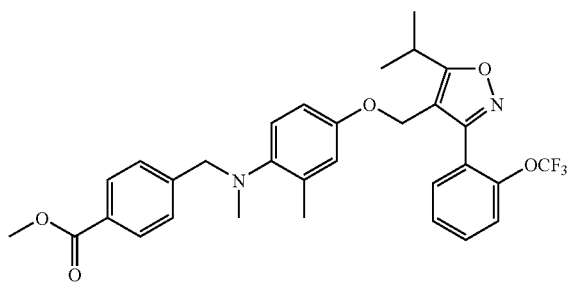

The title compound was prepared from appropriate starting materials using the synthesis described in Example 1.
$^1$HNMR(CDCl$_3$, 400 MHz) δ 7.98 (d, 2H, J=8.14), 7.58 (dd, 1H , 8.14), 7.50 (m, 1H), 7.40 (m, 4H), 6.95 (d, 1H, J=8.54), 6.63 (d, 1H, J=3.05), 6.57 (dd, 1H, J=8.76), 4.73 (s, 2H), 3.99 (s, 2H), 3.90 (s, 3H), 3.30 (m, 1H), 2.51 (s, 3H), 2.31 (s, 3H), 1.39 (d, 6H, J=6.97); MS (ESP+) m/e 591 (M+Na).

Example 23
4-{[(2-Chloro-4-{[3-(2,6-dichlorophenyl)-5-isopropylisoxazol-4-yl]methoxy}phenyl)amino]carbonyl}benzoic acid

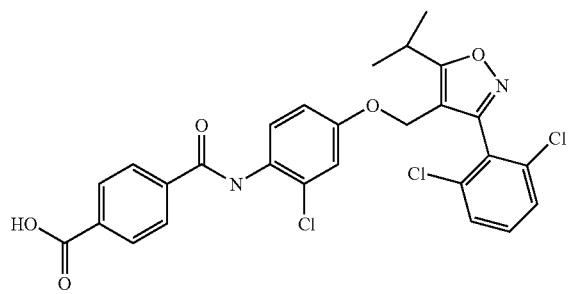

a) 2-Chloro-4{[3(2,6-dichlorophenyl)-5-isopropyl-isoxazol-4-yl]methoxy}aniline.

A mixture of 4-amino-3-chlorophenol (1.14 g, 7.9 mmol), triphenylphosphine (2.08 g, 7.9 mmol), [3-(2,6-dichlorophenyl)-5-isopropylisoxazol-4-yl]methanol (2.27 g, 7.9 mmol) in dichloromethane (20 mL) was treated with diisopropylazidodicarboxylate (1.57 mL, 7.9 mmol) dropwise. After stirring at ambient temperature for 16 h, the material was chromatographed on silica gel eluting with dichloromethane. Yield=1.73 g (53%) of 2-chloro-4-{[3-(2,6-dichlorophenyl)-5-isopropylisoxazol-4-yl]methoxy}aniline.

b) Methyl 4-{[(2-chloro-4-{[3-(2,6-dichlorophenyl)-5-isopropylisoxazol-4-yl]methoxy}phenyl)amino]carbonyl}benzoate.

A mixture of 2-chloro-4-{[3-(2,6-dichlorophenyl)-5-isopropylisoxazol-4-yl]methoxy}aniline (85 mg, 206 μmol), monomethyl terephthalate (37.2 mg, 206 μmol), 1-hydroxybenzotriazole (5.6 mg, 41 μmol) and 1-(3-dimethylaminopropyl)-3-ethylcarbodiimide hydrochloride (39.6 mg, 206 μmol) in dichloromethane (1 mL) was stirred at ambient temperature for 24 h. The reaction was partitioned with ethyl acetate and water. The organic layer was washed sequentially with saturated aqueous sodium hydrogensulfate and brine, then was dried over anhydrous sodium sulfate, filtered, and condensed to a residue which was chromatographed on silica gel eluting with 30% ethyl acetate/hexanes. Yield=65 mg, (55%) of methyl 4-{[(2-chloro-4-{[3-(2,6-dichlorophenyl)-5-isopropylisoxazol-4-yl]methoxy}phenyl)amino]carbonyl}-benzoate.

c) 4-{[(2-Chloro-4-{[3-(2,6-dichlorophenyl)-5-isopropylisoxazol-4-yl]methoxy}phenyl)amino]carbonyl}benzoic acid.

A solution of methyl 4-{[(2-chloro-4-{[3-(2,6-dichlorophenyl)-5-isopropylisoxazol-4-yl]methoxy}phenyl)amino]carbonyl}benzoate (10 mg, 17 μmol) in tetrahydrofuran (150 μL) was stirred vigorously with aqueous lithium hydroxide (104 μL, 0.5M) at ambient temperature for 24 h. The reaction was partitioned with ethyl acetate and then dried over anhydrous sodium sulfate, filtered, and was condensed to a residue.

Yield=9.5 mg (97%) of 4-{[(2-chloro-4-{[3-(2,6-dichlorophenyl)-5-isopropylisoxazol-4-yl]methoxy}phenyl)amino]carbonyl}benzoic acid.
$^1$HNMR (CDCl$_3$, 400 MHz) δ 8.29 (d, 1,H, J=9.05), 8.23 (m, 3H), 7.97 (d, 2H, J=8.33), 7.40 (m, 2H), 7.32 (dd, 1H, J=6.49), 6.83 (d, 1H, J=2.74), 6.75 (dd, 1H, J=6.49), 4.72 (s, 2H), 3.32 (m, 1H), 1.42 (d, 6H, J=7.09); MS (ESP−) m/e 560 (M).

Example 24
Methyl 3-[(2-chloro-4-{[3-(2,6-dichlorophenyl)-5-isopropyl-4-isoxazolyl]methoxy}anilino)carbonyl]benzoate

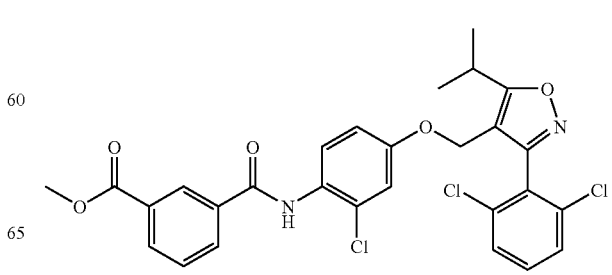

The title compound was prepared from appropriate starting materials using the synthesis described in Example 23.

$^1$HNMR (CDCl$_3$, 400 MHz) δ 8.52 (s, 1H), 8.26 (d, 1H, J=9.05), 8.23 (d, 1H, J=7.62), 8.19 (s, 1H), 8.10 (d, 1H, J=7.78), 7.59 (t, 1H, J=7.78), 7.41 (d, 2H, J=8.10), 7.32 (m, 1H), 6.83 (d, 1H, J=2.87), 6.74 (dd, 1H, J=6.24), 4.72 (s, 2H), 3.96 (s, 3H), 3.32 (m, 1H), 1.42 (d, 6H, J=6.93); MS (ESP+) m/e 573 (MH−).

Example 25

Methyl 4-[(2-chloro-4-{[3-(2,6-dichlorophenyl)-5-isopropyl-4-isoxazolyl]methoxy}anilino)carbonyl]benzoate

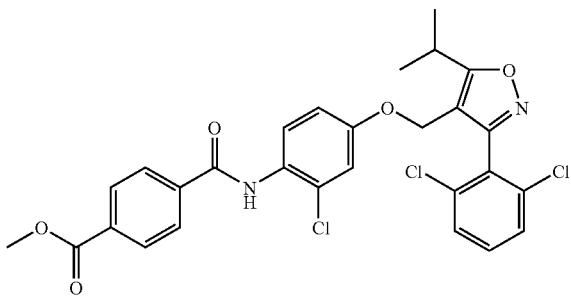

The title compound was prepared from appropriate starting materials using the synthesis described in Example 23.

$^1$HNMR (CDCl$_3$, 400 MHz) δ 8.30 (d, 1H, J=9.21), 8.19 (s, 1H), 8.16 (d, 2H, J=8.72), 7.94 (d, 2H, J=8.61), 7.42 (d, 1H, J=1.49), 7.40 (d, 1H, J=0.72), 7.33 (m, 1 H), 6.83 (d, 1H, J=2.78), 6.75 (dd, 1H, J=6.31), 4.72 (s, 2H), 3.32 (m, 1H), 1.43 (d, 6H, J=7.11); MS (ESP+) m/e 575 (MH+).

Example 26

3-[(4-{[3-(2,6-Dichlorophenyl)-5-isopropyl-4-isoxazolyl]methoxy}-2-methylanilino)carbonyl]benzoic acid

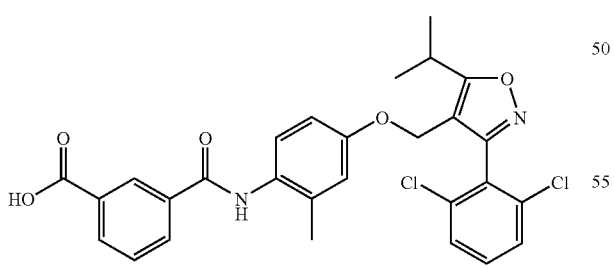

The title compound was prepared from appropriate starting materials using the synthesis described in Example 23.

$^1$HNMR (CDCl$_3$, 400 MHz) δ 8.50 (s, 1H), 8.22 (d, 1H, J=7.84), 8.11 (d, 1H, J=7.36), 7.70 (s,1H), 7.56 (t,1H, J=7.98), 7.47 (d,1H, J=8.94), 7.34 (m, 3H), 6.64 (s, 2H), 4.70 (s, 2H), 3.32 (m, 1H), 2.22 (s, 3H), 1.41 (d, 6H, J=7.03); MS (ESP−) m/e 539 (M).

Example 27

4-[(4-{[3-(2,6-Dichlorophenyl)-5-isopropyl-4-isoxazolyl]methoxy}-2-methylanilino)carbonyl]benzoic acid

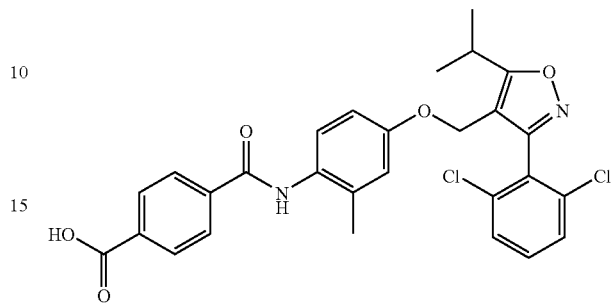

The title compound was prepared from appropriate starting materials using the synthesis described in Example 23.

$^1$HNMR (CDCl$_3$, 400 MHz) δ 8.21 (d, 2H, J=8.16), 7.96 (d, 2H, J=8.16), 7.58 (d, 1H, J=8.78), 7.55 (s, 1H), 7.41 (d, 2H, J=7.83), 7.31 (m, 1H), 6.67 (d, 2H, J=7.26), 4.71 (s, 2H), 3.33 (m,1H), 2.25 (s, 3H), 1.42 (d, 6H, J=7.02); MS (ESP+) m/e 539 (M).

Example 28

3-[(2-Chloro-4-{[3-(2,6-dichlorophenyl)-5-isopropyl-4-isoxazolyl]methoxy}anilino)carbonyl]benzoic acid

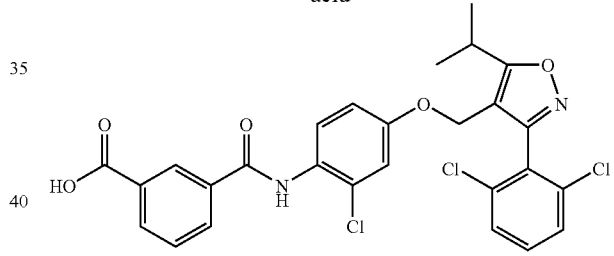

The title compound was prepared from appropriate starting materials using the synthesis described in Example 23.

$^1$HNMR (CD$_3$OD, 400 MHz) δ 8.59 (s,1H), 8.22 (d, 1H, J=8.02),8.15 (d, 1H, J=8.02), 7.62 (t, 1H, J=7.74), 7.48 (m, 4H), 6.91 (d, 1H, J=2.84), 6.78 (dd, 1H, J=5.92), 4.85 (s, 2H), 3.43 (m,1H), 1.41 (d, 6H, J=7.04); MS (ESP−) m/e 560 (M).

Example 29

3-[(4-{[3-(2,6-Dichlorophenyl)-5-isopropyl-4-isoxazolyl]methoxy}-2-dimethylanilino)carbonyl]benzoic acid

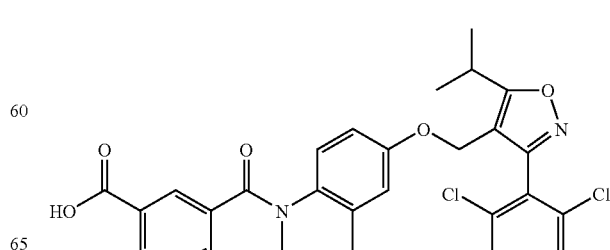

The title compound was prepared from appropriate starting materials using the synthesis described in Example 23.

¹HNMR (CDCl₃, 400 MHz) δ 7.99 (5s, 1H), 7.88 (d,1H, J=7.65), 7.36 (m, 3H), 7.29 (m, 1H), 7.18 (m, 1H), 6.87 (d, 1H, J=8.19), 6.43 (d, 2H, J=8.36), 4.63 (s, 2H), 3.30 (s, 3H), 3.25 (m, 1H), 2.10 (s, 3H), 1.33 (d, 6H, J=7.07); MS (ESP+) m/e 553 (M).

Example 30

3-[(2-Chloro-4-{[3-(2,6-dichlorophenyl)-5-isopropyl-4-isoxazolyl]methoxy}methylanilino)carbonyl]benzoic acid

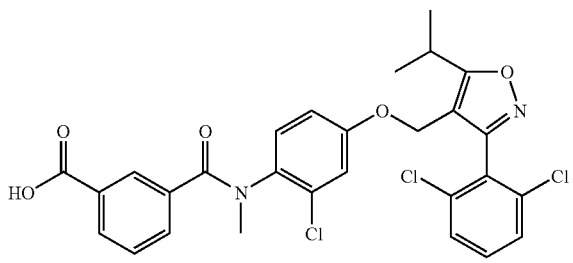

The title compound was prepared from appropriate starting materials using the synthesis described in Example 23.

¹HNMR (CDCl₃, 400 MHz) δ 8.05 (s, 1H), 7.95 (d, 1H, J=8.03),7.53 (d, 1H, J=8.03), 7.38 (d, 1H, J=2.07), 7.36 (s, 1H), 7.30 (m, 2H), 6.98 (d, 1H, J=8.83), 6.68 (d, 1H, J=2.77), 6.51 (dd, 1H, J=8.89), 4.85 (s, 2H), 3.34 (s, 3H), 1.36 (d, 6H, J=6.97); MS (ESP+) m/e 575 (MH+).

Example 31

4-[(2-Chloro-4-{[3-(2,6-dichlorophenyl)-5-isopropyl-4-isoxazolyl]methoxy}methylanilino)carbonyl]benzoic acid

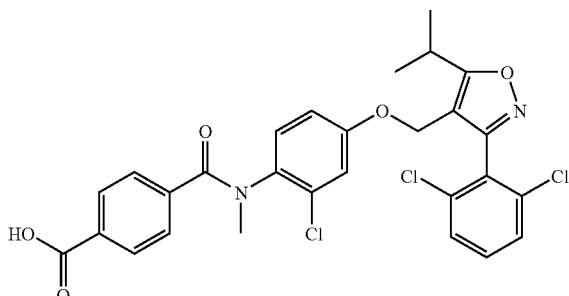

The title compound was prepared from appropriate starting materials using the synthesis described in Example 23.

¹HNMR (CDCl₃, 400 MHz) δ 7.87 (d, 2H, J=8.61), 7.37 (m, 4H), 7.30 (m, 1H), 6.93 (d, 1H, J=8.75), 6.70 (d, 1H, J=2.81), 6.49 (dd, 1H, J=8.90), 4.64 (s, 2H), 3.33 (s, 3H), 3.26 (m, 1H), 1.38 (d, 6H, J=6.97); MS (ESP+) m/e 575 (MH+).

Example 32

3-{[4-({5-Isopropyl-3-[2-(trifluoromethoxy)phenyl]-4-isoxazolyl}methoxy)-2-dimethylanilino]carbonyl}benzoic acid

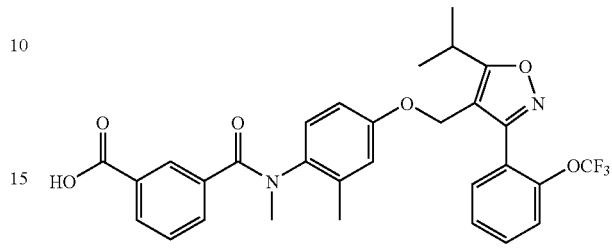

The title compound was prepared from appropriate starting materials using the synthesis described in Example 23.

¹HNMR (CDCl₃, 400 MHz) δ 8.00 (s,1H), 7.94 (d,1H, J=7.84),7.49 (m, 3H), 7.29 (m, 3H), 6.90 (d, 1H, J=9.39), 6.46 (m, 2H), 4.69 (s, 2H), 3.34 (s, 3H), 3.25 (m, 1H), 2.12 (s, 3H), 1.33 (d, 6H, J=6.95); MS (ESP+) m/e 569 (M).

Example 33

3-{[4-({5-Isopropyl-3-[2-(trifluoromethoxy)phenyl]-4-isoxazolyl}methoxy)-2-methylanilino]carbonyl}benzoic acid

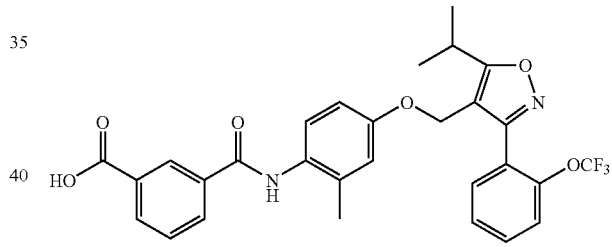

The title compound was prepared from appropriate starting materials using the synthesis described in Example 23.

¹HNMR (CDCl₃, 400 MHz) δ 8.43 (s, 1H), 8.12 (d, 1H, J=7.11), 8.00 (s, 1H), 7.89 (s, 1H), 7.44 (m, 6H), 6.59 (s, 2H), 4.74 (s, 2H), 3.28 (m, 1H), 2.16 (s, 3H), 1.37 (d, 6H, J=7.03); MS (ESP+) m/e 555 (M).

Example 34

3-{[2-Chloro-4-({5-isopropyl-3-[2-(trifluoromethoxy)phenyl]-4-isoxazolyl}methoxy)methylanilino]carbonyl}benzoic acid

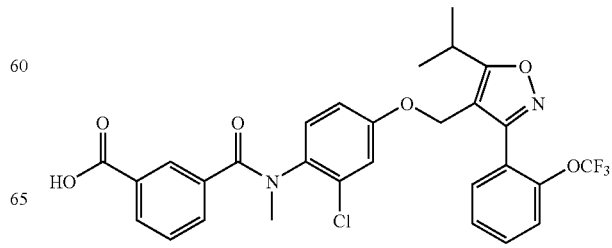

The title compound was prepared from appropriate starting materials using the synthesis described in Example 23.

$^1$HNMR (CDCl$_3$, 400 MHz) δ 8.06 (s, 1H), 7.93(d, 1H, J=7.55), 7.48 (m, 3H,), 7.30 (m, 3H), 6.97 (d, 1H, J=8.80), 6.67 (d, 1H, J=2.79), 6.49 (dd, 1H, J=8.80), 4.69 (s, 2H), 3.33 (s, 3H), 3.22 (m, 1H), 1.33 (d, 6H, J=6.99); MS (ESP+) m/e 589 (M).

Example 35

Methyl 3-{[(4-{[3-(2,6-dichlorophenyl)-5-isopropyl-isoxazol-4-yl]methoxy}-2-methylphenyl)(methyl)amino]sulfonyl}benzoate

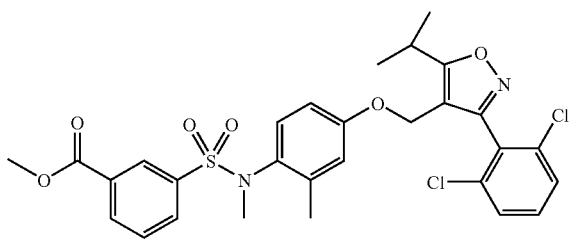

a) Methyl 4-(chlorosulfonyl)benzoate.

A mixture of methyl-4-aminobenzoate (1.0 g, 6.6 mmol) in concentrated hydrochloric acid (15 mL) was maintained at 0° C. as a solution of sodium nitrite (1.12 g, 13.2 mmol) in water (4 mL) was added dropwise with stirring. This reaction was maintained at 0° C. for 30 minutes. In a separate flask, a mixture of copper(I)chloride (89 mg, 0.66 mmol) and glacial acetic acid (9.9 mL) cooled to below room temperature was crude diazonium salt was then added to the second flask portionwise with extreme caution. The mixture was allowed to stir at ambient temperature for 3 h before being poured onto crushed ice. The resulting solid was filtered. Additional product was recovered by extraction of the aqueous filtrate with ethyl acetate. The combined yield of methyl 4-(chlorosulfonyl)benzoate is 0.65 g. (42%).

b) 3-(2,6-Dichlorophenyl)-5-isopropyl-4-[(3-methyl-4-nitrophenoxy)methyl]-isoxazole.

A solution of [3-(2,6-dichlorophenyl)-5-isopropylisoxazol-4-yl]methanol (500 mg, 1.79 mmol) in dimethylformamide (6 mL) at 0° C. was treated with sodium hydride (60% dispersion in oil, 72 mg, 1.8 mmol) and was maintained for 15 minutes before the addition of 5-fluoro-2-nitrotoluene (182 µL, 1.5 mmol). The reaction was then allowed to stir at ambient temperature for 16 h. The product was extracted by partitioning the mixture in diethyl ether (50 mL) and water (50 mL). The aqueoues phase was extracted with diethyl ether (3×50 mL) then the organics were combined and washed with brine (50 mL), dried over anhydrous magnesium sulfate, filtered and and concentrated to yield a crude oil. The product was purified by column chromatography on silica gel eluting with 20% ethyl acetate/hexanes. Yield=379 mg (60%) of 3-(2,6-dichlorophenyl)-5-isopropyl-4-[(3-methyl 4nitrophenoxy)methyl]-isoxazole.

c) 4-{[3-(2,6-Dichlorophenyl)-5-isopropylisoxazol-4-yl]methoxy}-2-methylphenylamine.

A solution of 3-(2,6-dichlorophenyl)-5-isopropyl-4-[(3-methyl-4-nitrophenoxy)methyl]isoxazole (0.36 g, 0.86 mmol) in ethanol (3 mL) was treated with tni(II)chloride (0.71 g, 3.2 mmol) and refluxed overnight. Water (15 mL) was added and the pH adjusted to 10-11 with solid sodium carbonate. The product was then extracted with chloroform; the combined organic layers were washed with brine, dried over anhydrous magnesium sulfate, filtered, and condensed to a residue which was chromatographed on silica gel using 50% ethyl acetateihexane. Yield=0.24 g. (72%) of 4-{[3-(2,6-dichlorophenyl)-5-isopropylisoxazol-4-yl]methoxy}-2-methylphenylamine.

d) Methyl 3-{[(4-{[3-(2,6-dichlorophenyl)-5-isopropylisoxazol-4-yl]methoxy}-2-methylphenyl)amino]sulfonyl}benzoate.

A mixture of 4-{[3-(2,6-dichlorophenyl)-5-isopropylisoxazol-4-yl]methoxy}-2-methylphenylamine (85 mg, 217 µmol), methyl 4-(chlorosulfonyl)benzoate (51 mg, 217 µmol), pyridine (52 µL, 651 µmol), and dioxane (1.1 mL) was stirred at ambient temperature overnight. The reaction was condensed and the resulting residue chromatographed on silica gel eluting with 50% ethyl acetateihexanes. Yield=119 mg (93%) of methyl 3-{[(4-{[3-(2,6-dichlorophenyl)-5-isopropylisoxazol-4-yl]methoxy}-2-methylphenyl)amino]sulfonyl}benzoate.

e) Methyl 3-{[(4-{[3-(2,6-dichlorophenyl)-5-isopropylisoxazol-4-yl]methoxy}-2-methylphenyl)(methyl)amino]sulfonyl}benzoate.

A solution of methyl 3-{[(4-{[3-(2,6-dichlorophenyl)-5-isopropylisoxazol-4-yl]methoxy}-2-methylphenyl)amino]sulfonyl}benzoate (32 mg, 56 µmol) in dimethylformamide (560 µL) was stirred with cesium carbonate (91 mg, 280 µmol) and methyl iodide (17.3 µL, 280 µmol) at 80° C. in a sealed vial. Water (2 mL) was added and the product was extracted with 50% ethyl acetate/hexanes. Yield=31 mg 94%) of methyl 3-{[(4-{[3-(2,6-dichlorophenyl)-5-isopropylisoxazol-4-yl]methoxy}-2-methylphenyl)(methyl)amino]sulfonyl}benzoate.

$^1$H NMR (CDCl$_3$, 400 MHz) δ 8.40-8.36 (m, 1H), 8.29-8.24 (m, 1H), 7.85-7.80 (m, 1H), 7.58 (t, 1H), 7.43-7.37 (m, 2H), 7.35-7.29 (m, 1H), 6.68-6.63 (m, 1H), 6.46-6.37 (m, 2H), 4.67 (s, 2H), 3.94 (s, 3H), 3.37-3.25 (m, 1H), 3.10 (s, 3H), 2.29 (s, 3H), 1.41 (d, 6H); MS (ESP+) m/e 605 (MH$^+$).

Example 36

Methyl 3-{[(2-chloro-4-{[3-(2,6-dichlorophenyl)-5-isopropylisoxazol-4-yl]methoxy}-phenyl)amino]sulfonyl}benzoate

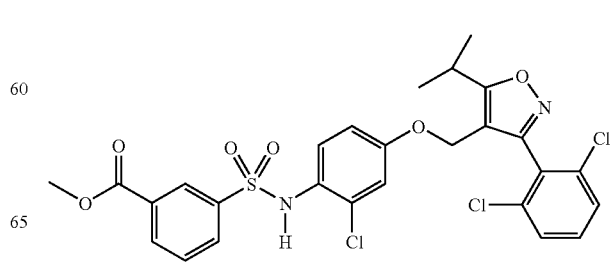

The title compound was prepared from appropriate starting materials using the synthesis described in Example 35.

¹H NMR (CDCl₃, 400 MHz) δ 8.39-8.36 (m, 1H), 8.21-8.17 (m, 1H), 7.82-7.78 (m, 1H), 7.51-7.45 (m, 2H), 7.40-7.36 (m, 2H), 7.34-7.28 (m, 1H), 6.68-6.63 (m, 1H), 6.61-6.58 (m, 1H), 4.66 (s, 2H), 3.90 (s, 3H), 3.31-3.23 (m, 1H), 1.39 (d, 6H); MS (ESP+) (MH⁺).

Example 37

Methyl 3-{[1(4-{[3-(2,6-dichlorophenyl)-5-isopropylisoxazol-4-yl]methoxy}-2-methylphenyl)amino]sulfonyl}benzoate

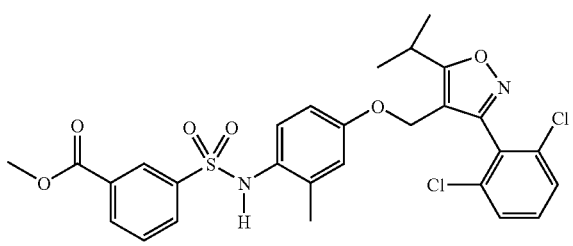

The title compound was prepared from appropriate starting materials using the synthesis described in Example 35.

¹H NMR (CDCl₃, 400 MHz) δ 8.42-8.40 (m, 1H), 8.24-8.20 (m, 1H), 7.81-7.77 (m, 1H), 7.53-7.48 (m, 1H), 7.41-7.37 (m, 2H), 7.34-7.29 (m, 1H), 6.97-6.93 (m, 1H), 6.52-6.48 (m, 2H), 6.11 (s, 1H), 4.67 (s, 2H), 3.92 (s, 3H), 3.34-3.25 (m, 1H), 1.93 (s, 3H), 1.40 (d, 6H); MS (ESP+) m/e 591 (MH⁺).

Example 38

Methyl 3-{[(4-{[3-(2,6-dichlorophenyl)-5-isopropyl-isoxazol-4yl]methoxy}phenyl)amino]-sulfonyl}benzoate

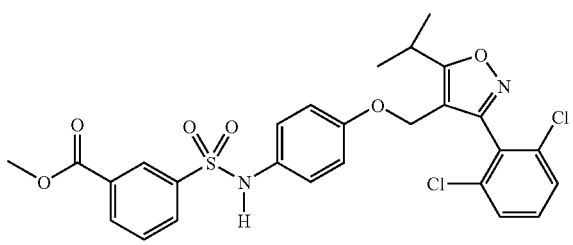

The title compound was prepared from appropriate starting materials using the synthesis described in Example 35.

¹H NMR (CDCl₃, 400 MHz) δ 8.44-8.39 (m, 1H), 8.22-8.16 (m, 1H), 7.84-7.78 (m, 1H), 7.52-7.46 (m, 1H), 7.40-7.36 (m, 2H), 7.33-7.27 (m, 1H), 6.93-6.87 (m, 2H), 6.64-6.58 (m, 2H), 4.67 (s, 2H), 3.91 (s, 3H), 3.34-3.22 (m, 1H), 1.38 (d, 6H); MS (ESP+) m/e 576 (MH⁺).

Example 39

3-{[(4-{[3-(2,6-Dichlorophenyl)-5-isopropylisoxazol-4-yl]methoxy}-2-methylphenyl)-amino]sulfonyl}benzoic acid

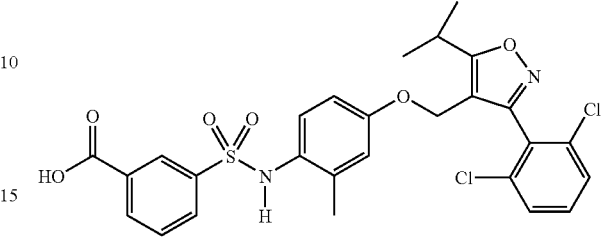

The title compound was prepared from appropriate starting materials using the synthesis described in Example 35.

¹H NMR (CDCl₃, 400 MHz) δ 8.51 (s, 1H), 8.29-8.21 (m,1H), 7.85-7.76 (m, 1H), 7.56-7.47 (m,1H), 7.41-7.35 (m, 2H), 7.34-7.28 (m, 1H), 6.99-6.91 (m, 1H), 6.53-6.42 (m, 3H), 4.67 (s, 2H), 3.35-3.24 (m, 1H), 1.93 (s, 3H), 1.38 (d, 6H); MS (ESP+) m/e 576 (MH⁺).

Example 40

3-{[(4-{[3-(2,6-Dichlorophenyl)-5-isopropylisoxazol-4-yl]methoxy}phenyl)amino]-sulfonyl}benzoic acid

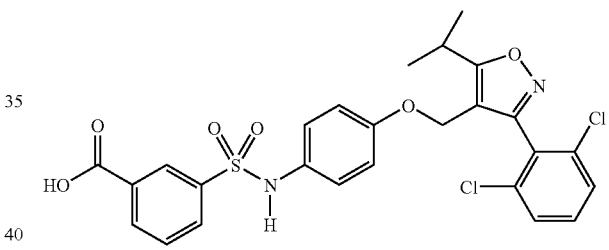

The title compound was prepared from appropriate starting materials using the synthesis described in Example 35.

¹H NMR (CDCl₃, 400 MHz) δ 8.55-8.43 (m, 1H), 8.17-8.05 (m, 1H), 7.81-7.71 (m, 1H), 7.47-7.32 (m, 3H), 7.32-7.26 (m, 1H), 6.96-6.83 (m, 2H), 6.65-6.53 (m, 2H), 4.66 (s, 2H), 3.31-3.21 (m, 1H), 1.35 (d, 6H); MS (ESP+) m/e 562 (MH⁺).

Example 41

Methyl 3-{[(2-chloro-4-{[3-(2,6-dichlorophenyl)-5-isopropylisoxazol-4-yl]methoxy}-phenyl)(methyl)amino]sulfonyl}benzoate

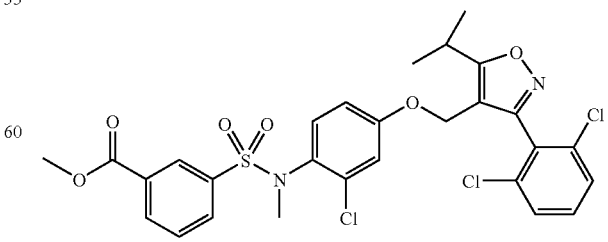

The title compound was prepared from appropriate starting materials using the synthesis described in Example 35.

¹H NMR (CDCl₃, 400 MHz) δ 8.43 (s, 1H), 8.27-8.22 (m, 1H), 7.92-7.87 (m, 1H), 7.60-7.54 (m, 1H), 7.43-7.38 (m, 2H), 7.37-7.30 (m, 1H), 7.09-7.04 (m, 1H), 6.78-6.75 (m, 1H), 6.65-6.60 (m,1H), 4.69 (s, 2H), 3.94 (s, 3H), 3.36-3.24 (m, 1H), 3.18(s, 3H), 1.42 (d, 6H); MS (ESP+) m/e 625 (MH⁺).

Example 42

Methyl 3-{[(4-{[3-(2,6-dichlorophenyl)-5-isopropyl-isoxazol-4-yl]methoxy}phenyl)-(methyl)amino]sulfonyl}benzoate

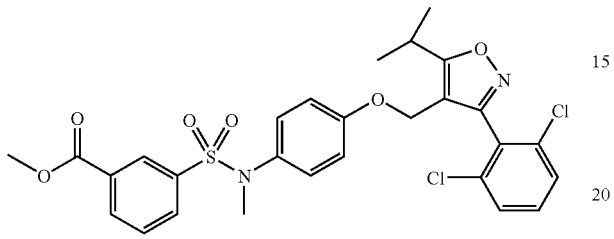

The title compound was prepared from appropriate starting materials using the synthesis described in Example 35.
¹H NMR (CDCl₃, 400 MHz) δ 8.29-8.22 (m, 2H), 7.67-7.62 (m, 1H), 7.55-7.49 (m, 1H), 7.43-7.37 (m, 2H), 7.35-7.30 (m, 1H), 6.93-6.87 (m, 2H), 6.71-6.64 (m, 2H), 4.70 (s, 2H), 3.92 (s, 3H), 3.38-3.25 (m, 1H), 3.14 (s, 3H), 1.41 (d, 6H); MS (ESP+) m/e 590 (MH⁺).

Example 43

Methyl 3-{[(2-chloro-4-{[3-(2,6-dichlorophenyl)-5-isopropylisoxazol-4-yl]methoxy}-phenyl)(ethyl)amino]sulfonyl}benzoate

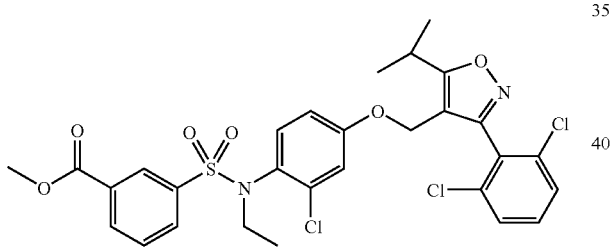

The title compound was prepared from appropriate starting materials using the synthesis described in Example 35.
¹H NMR (CDCl₃, 400 MHz) δ 8.45-8.39 (m, 1H), 8.26-8.19 (m, 1H), 7.91-7.85 (m, 1H), 7.58-7.51 (m, 1H), 7.43-7.38 (m, 2H), 7.36-7.30 (m, 1H), 7.04-6.99 (m, 1H), 6.80-6.75 (m, 1H), 6.67-6.61 (m, 1H), 4.70 (s, 2H), 3.93 (s, 3H), 3.71-3.47 (m, 2H), 3.36-3.24 (m, 1H), 1.42 (d, 6H), 1.07 (t, 3H); MS (ESP+) m/e 639 (MH⁺).

Example 44

Methyl 3-{[(4-{[3-(2,6-dichlorophenyl)-5-isopropyl-isoxazol-4-yl]methoxy}-2-methyl-phenyl)(ethyl)amino]sulfonyl}benzoate

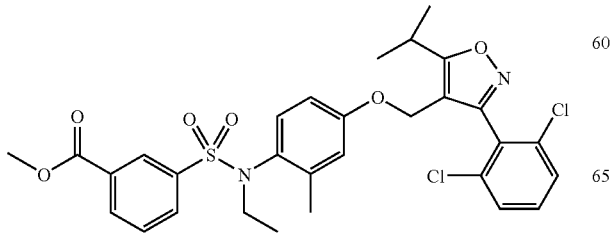

The title compound was prepared from appropriate starting materials using the synthesis described in Example 35.
¹H NMR (CDCl₃, 400 MHz) δ 8.39-8.35 (m, 1H), 8.28-8.22 (m, 1H), 7.83-7.78 (m, 1H), 7.59-7.53 (m, 1H), 7.43-7.38 (m, 2H), 7.36-7.30 (m, 1H), 6.69-6.65 (m, 1H), 6.48-6.42 (m, 1H), 6.42-6.36 (m, 1H), 4.69 (s, 2H), 3.93 (s, 3H), 3.84-3.73 (m, 1H), 3.37-3.20 (m, 2H), 2.28 (s, 3H), 1.42 (d, 6H), 1.02 (t, 3H); MS (ESP+) m/e 619 (MH⁺).

Example 45

Methyl 3-{[(4-{[3-(2,6-dichlorophenyl)-5-isopropyl-isoxazol-4-yl]methoxy}phenyl)(ethyl)-amino]sulfonyl}benzoate

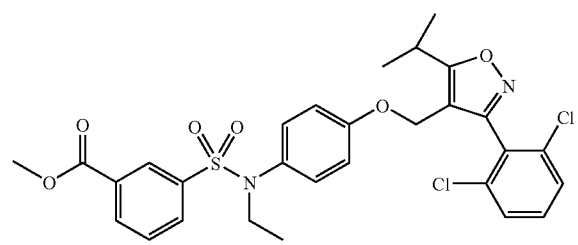

The title compound was prepared from appropriate starting materials using the synthesis described in Example 35.
¹H NMR (CDCl₃, 400 MHz) δ 8.33-8.30 (m, 1H), 8.25-8.20 (m, 1H), 7.74-7.69 (m, 1H), 7.56-7.50 (m, 1H), 7.42-7.38 (m, 2H), 7.35-7.30 (m, 1H), 6.88-6.84 (m, 2H), 6.71-6.66 (m, 2H), 4.71 (s, 2H), 3.93 (s, 3H), 3.56 (q, 2H), 3.37-3.26 (m, 1), 1.41 (d, 3H); MS (ESP+) m/e 605 (M⁺).

Example 46

3-{[(2-Chloro-4-{[3-(2,6-dichlorophenyl)-5-isopropylisoxazol-4-yl]methoxy}phenyl)amino]sulfonyl}benzoic acid

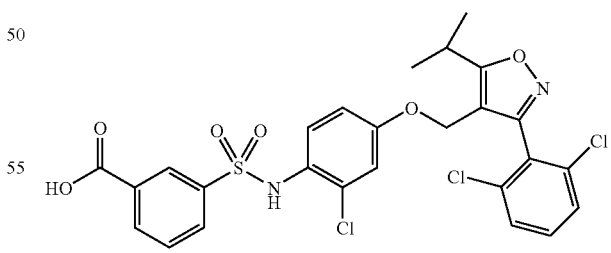

The title compound was prepared from appropriate starting materials using the synthesis described in Example 35.
¹H NMR (CDCl₃, 400MHz) δ 8.35 (s, 1H), 8.02 (d, 1H), 7.92 (t, 2H), 7.48 t, 1H), 7.42 (d, 2H), 7.34 (d, 1H), 6.82 (s, 1H), 6.72 (dd, 1H), 4.73 (s, 2H), 3.33 (m, 1H), 1.42 (d, 6H); MS (ESP+) m/e 595 (MH⁺).

Example 47

3-{[(2-Chloro-4-{[3-(2,6-dichlorophenyl)-5-isopropylisoxazol-4-yl]methoxy}phenyl)-(methyl)amino]sulfonyl}benzoic acid

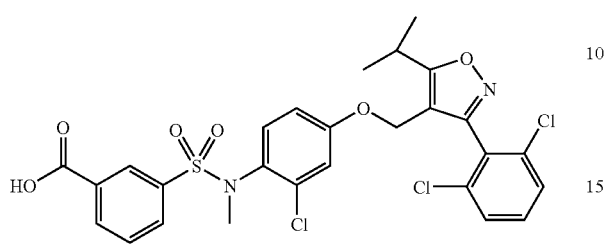

The title compound was prepared from appropriate starting materials using the synthesis described in Example 35.
¹H NMR (CDCl₃, 400 MHz) δ 8.51-8.49 (m, 1H), 8.33-8.29 (m, 1H), 7.99-7.94 (m, 1H), 7.64-7.58 (m, 1H), 7.43-7.38 (m, 2H), 7.36-7.31 (m, 1H), 7.13-7.06 (m, 1H), 6.79-6.74 (m, 1H), 6.67-6.62 (m, 1H), 4.70 (s, 2H), 3.35-3.24 (m, 1H), 3.19 (s, 3H), 1.42 (d, 6H); MS (ESP+) m/e 611 (MH⁺).

Example 48

3-{[(4-{[3-(2,6-Dichlorophenyl)-5-isopropylisoxazol-4-yl]methoxy}-2-methylphenyl)-(methyl)amino]sulfonyl}benzoic acid

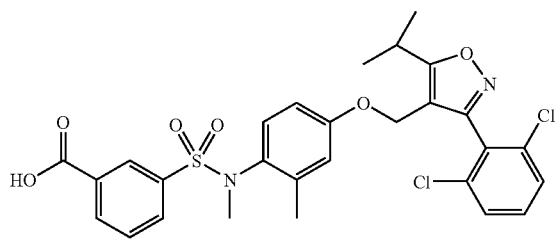

The title compound was prepared from appropriate starting materials using the synthesis described in Example 35.
¹H NMR (CDCl₃, 400 MHz) δ 8.48-8.45 (m, 1H), 8.36-8.31 (m, 1H), 7.92-7.88 (m, 1H), 7.63 (t, 1H), 7.42-7.38 (m, 2H), 7.35-7.30 (m, 1H), 6.68-6.65 (m, 1H), 6.47-6.39 (m, 2H), 4.69 (s, 2H), 3.37-3.25 (m, 1H), 3.12 (s, 3H), 2.31 (s, 3H), 1.41 (d, 6H); MS (ESP+) m/e 590 (MH⁺).

Example 49

3-{[(4-{[3-(2,6-Dichlorophenyl)-5-isopropylisoxazol-4-yl]methoxy}phenyl)(methyl)-amino]sulfonyl}benzoic acid

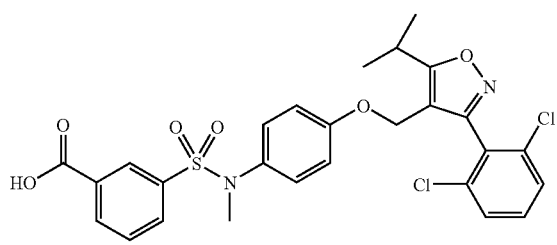

The title compound was prepared from appropriate starting materials using the synthesis described in Example 35.
¹H NMR (CDCl₃, 400 MHz) δ 8.35-8.28 (m, 2H), 7.74-7.69 (m, 1H), 7.60-7.53 (m, 1H), 7.42-7.37 (m, 2H), 7.35-7.29 (m, 1H), 6.94-6.88 (m, 2H), 6.70-6.65 (m, 2H), 4.71 (s, 2H), 3.37-3.25 (m, 1H), 3.15 (s, 3H), 1.40 (d, 6H); MS (ESP+) m/e 576 (MH⁺).

Example 50

3-{[(2-Chloro-4-{[3-(2,6-dichlorophenyl)-5-isopropylisoxazol-4-yl]methoxy}phenyl)-(ethyl) amino]}benzoic acid

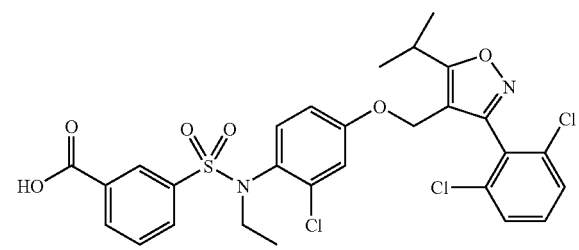

The title compound was prepared from appropriate starting materials using the synthesis described in Example 35.
¹H NMR (CDCl₃, 400 MHz) δ 8.52-8.46 (m, 1H), 8.32-8.26 (m, 1H), 7.97-7.92 (m, 1H), 7.62-7.56 (m, 1H), 7.43-7.38 (m, 2H), 7.37-7.30 (m, 1H), 7.07-7.01 (m, 1H), 6.80-6.76 (m, 1H), 6.67-6.62 (m, 1H), 4.71 (s, 2H), 3.72-3.48 (m, 2H), 3.36-3.24 (m, 1H), 1.42 (d, 6H), 1.08 (t, 3H); MS (ESP+) m/e 625 (MH⁺).

Example 51

3-{[(4-{[3-(2,6-Dichlorophenyl)-5-isopropylisoxazol-4-yl]methoxy}-2-methylphenyl)-(ethyl)amino]}benzoic acid

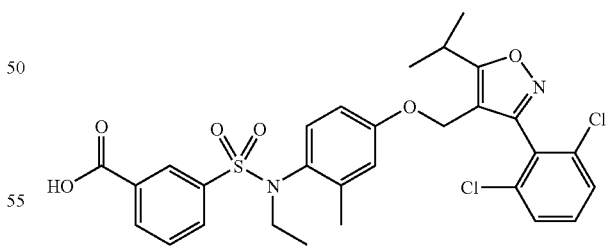

The title compound was prepared from appropriate starting materials using the synthesis described in Example 35.
¹H NMR (CDCl₃, 400 MHz) δ 8.45-8.43 (m, 1H), 8.33-8.27 (m, 1H), 7.89-7.84 (m, 1H), 7.63-7.56 (m,1H), 7.42-7.37 (m, 2H), 7.36-7.29 (m, 1H), 6.69-6.65 (m, 1H), 6.48-6.42 (m, 1H), 6.41-6.36 (m, 1H), 4.70 (s, 2H), 3.84-3.73 (m, 1H), 3.36-3.21 (m, 2H), 2.28 (s, 3H), 1.42 (d, 6H), 1.03 (t, 3H); MS (ESP+) m/e 605 (M^H+).

Example 52

3-{[(4-{[3-(2,6-Dichlorophenyl)-5-isopropylisoxazol-4-yl]methoxy}phenyl)(ethyl)-amino]sulfonyl}benzoic acid

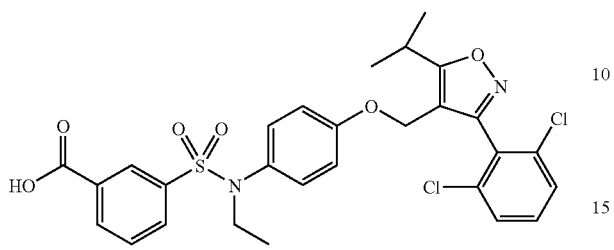

The title compound was prepared from appropriate starting materials using the synthesis described in Example 35.
$^1$H NMR (CDCl$_3$, 400 MHz) δ 8.40-8.37 (m, 1H), 8.31-8.27 (m, 1H), 7.80-7.76 (m, 1H), 7.60-7.54 (m, 1H), 7.42-7.37 (m, 2H), 7.36-7.29 (m, 1H), 6.90-6.84 (m, 2H), 6.72-6.67 (m, 2H), 4.72 (s, 2H), 3.57 (q, 2H), 3.37-3.26 (m, 1H), 1.41 (d, 6H), 1.06 (t, 3H); MS (ESP+) m/e 589 (M$^+$).

Example 53

Methyl 4-{[(2-chloro-4-{[3-(2,6-dichlorophenyl)-5-isopropylisoxazol-4-yl]methoxy}-phenyl)amino]sulfonyl}benzoate

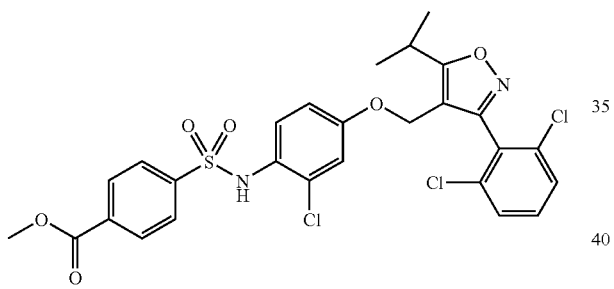

The title compound was prepared from appropriate starting materials using the synthesis described in Example 35.
$^1$H NMR (CDCl$_3$, 400 MHz) δ 8.04 (d, 2H), 7.71 (d, 2H), 7.53-7.47 (m, 1H), 7.42-7.36 (m, 2H), 7.35-7.29 (m, 1H), 6.69-6.59 (m, 3H), 4.66 (s, 2H), 3.93 (s, 3H), 3.34-3.22 (m, 1H), 1.40 (d, 6H); MS (ESP+) m/e 611 (MH$^+$).

Example 54

Methyl 4-{[(4-{[3-(2,6-dichlorophenyl)-5-isopropyl-isoxazol-4-yl]methoxy}-2-methyl-phenyl)amino]sulfonyl}benzoate

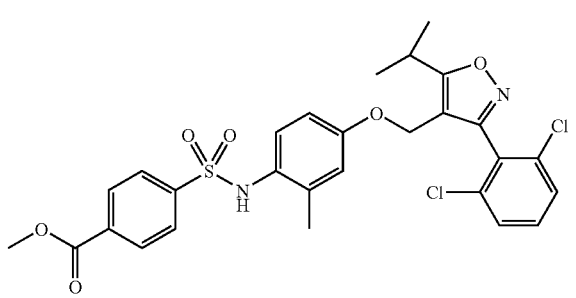

The title compound was prepared from appropriate starting materials using the synthesis described in Example 35.
$^1$H NMR (CDCl$_3$, 400 MHz) δ 8.07 (d, 2H), 7.72 (d, 2H), 7.41-7.36 (m, 2H), 7.34-7.28 (m, 1H), 7.00-6.94 (m, 1H), 6.53-6.46 (m, 2H), 6.19 (s, 1H), 4.66 (s, 2H), 3.94 (s, 3H), 3.36-3.24 (m, 1H), 1.87 (s, 3H), 1.40 (d, 6H); MS (ESP+) m/e 591 (MH$^+$).

Example 55

Methyl 4-{[(4-{[3-(2,6-dichlorophenyl)-5-isopropyl-isoxazol-4-yl]methoxy}phenyl)-amino]sulfonyl}benzoate

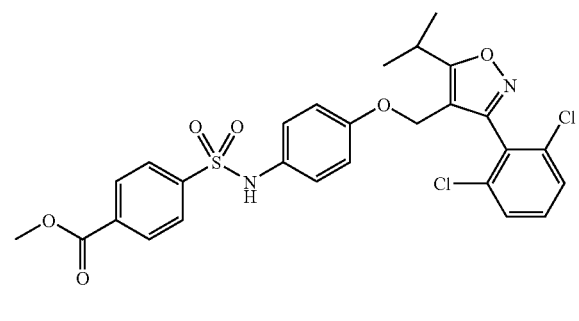

The title compound was prepared from appropriate starting materials using the synthesis described in Example 35.
$^1$H NMR (CDCl$_3$, 400 MHz) δ 8.05 (d, 2H), 7.72 (d, 2H), 7.41-7.35 (m, 2H), 7.33-7.27 (m, 1H), 6.91-6.85 (m, 2H), 6.64-6.59 (m, 2H), 6.50 (s, 1H), 4.66 (s, 2H), 3.93 (s, 3H), 3.33-3.22 (m, 1H), 1.38 (d, 6H); MS (ESP+) m/e 576 (MH$^+$).

Example 56

4-{[(2-Chloro-4-{[3-(2,6-dichlorophenyl)-5-isopropylisoxazol-4-yl]methoxy}phenyl)-amino]sulfonyl}benzoic acid

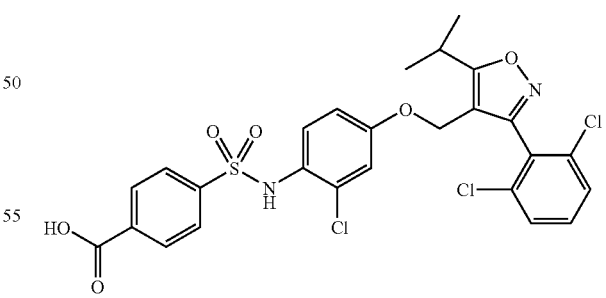

The title compound was prepared from appropriate starting materials using the synthesis described in Example 35.
$^1$H NMR (CDCl$_3$, 400 MHz) δ 8.10 (d, 2H), 7.75 (d, 2H), 7.54-7.49 (m, 1H), 7.42-7.36 (m, 2H), 7.35-7.28 (m, 1H), 6.72-6.59 (m, 3H), 4.67 (s, 2H), 3.34-3.22 (m, 1H), 1.39 (d, 6H); MS (AP+) m/e 597 (MH$^+$).

Example 57

4-{[(4-{[3-(2,6-Dichlorophenyl)-5-isopropylisoxazol-4-yl]methoxy}-2-methylphenyl)-amino]sulfonyl}benzoic acid

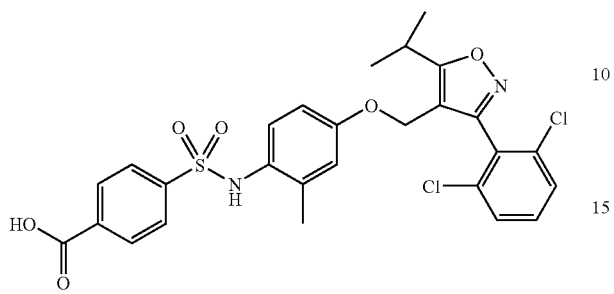

The title compound was prepared from appropriate starting materials using the synthesis described in Example 35.
¹H NMR (CDCl₃, 400 MHz) δ 8.10 (d, 2H), 7.73 (d, 2H), 7.40-7.34 (m, 2H), 7.34-7.27 (m, 1H), 7.00-6.92 (m, 1H), 6.54-6.45 (m, 2H), 6.28-6.18 (m, 1H), 4.67 (s, 2H), 3.35-3.24 (m, 1H), 2.04 (s, 3H), 1.38 (d, 6H); MS (ESP−) m/e 575 (M⁻).

Example 58

4-{[(4-{[3-(2,6-Dichlorophenyl)-5-isopropylisoxazol-4-yl]methoxy}phenyl)amino]-sulfonyl}benzoic acid

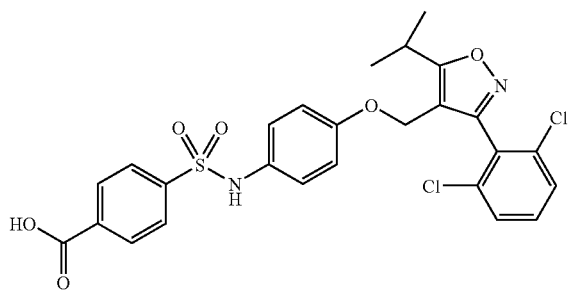

The title compound was prepared from appropriate starting materials using the synthesis described in Example 35.
¹H NMR (CDCl₃, 400 MHz) δ 8.12-7.99 (m, 2H), 7.76-7.64 (m, 2H), 7.40-7.26 (m, 3H), 6.93-6.83 (m, 2H), 6.66-6.56 (m, 2H), 4.67 (s, 2H), 3.32-3.20 (m, 1H), 1.37 (d, 6H); MS (ESP−) m/e 561 (M⁻).

Example 59

Methyl 4-{[(4-{[3-(2,6-dichlorophenyl)-5-isopropyl-isoxazol-4-yl]methoxy}-2-methyl-phenyl)(methyl)amino]sulfonyl}benzoate

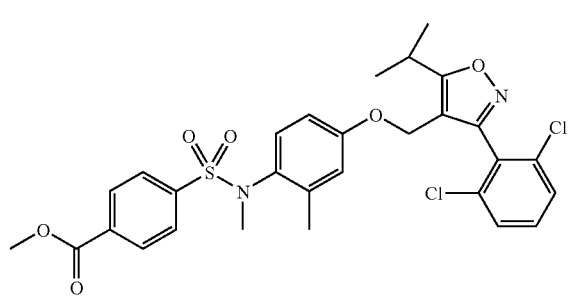

The title compound was prepared from appropriate starting materials using the synthesis described in Example 35.
¹H NMR (CDCl₃, 400 MHz) δ 8.15 (d, 2H), 7.75 (d, 2H), 7.43-7.37 (m, 2H), 7.36-7.29 (m, 1H), 6.68-6.62 (m, 1H), 6.45-6.34 (m, 2H), 4.67 (s, 2H), 3.97 (s,3H), 3.36-3.24 (m, 1H), 3.10 (s, 3H), 2.28 (s, 3H), 1.41 (d, 6H); MS (ESP+) m/e 627 (M+Na⁺).

Example 60

Methyl 4-{[(4-{[3-(2,6-dichlorophenyl)-5-isopropylisoxazol-4-yl]methoxy}phenyl)-(methyl)amino]sulfonyl}benzoate

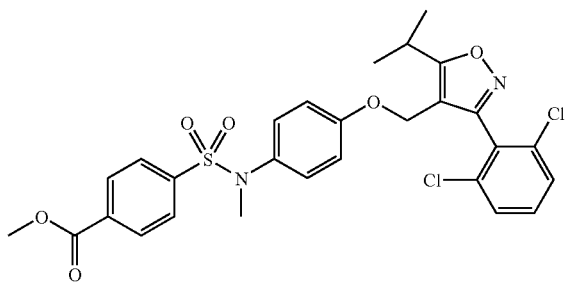

The title compound was prepared from appropriate starting materials using the synthesis described in Example 35.
¹H NMR (CDCl₃, 400 MHz) δ 8.10 (d, 2H), 7.60 (d, 2H), 7.43-7.38 (m, 2H), 7.36-7.29 (m, 1H), 6.91-6.86 (m, 2H), 6.69-6.64 (m, 2H), 4.70 (s, 2H), 3.96 (s, 3H), 3.37-3.25 (m, 1H), 3.12 (s, 3H), 1.41 (d, 6H); MS (ESP+) m/e 613 (M+Na⁺).

Example 61

Methyl 4-{[(4-{[3-(2,6-dichlorophenyl)-5-isopropylisoxazol-4-yl]methoxy}phenyl)-(ethyl)amino]sulfonyl}benzoate

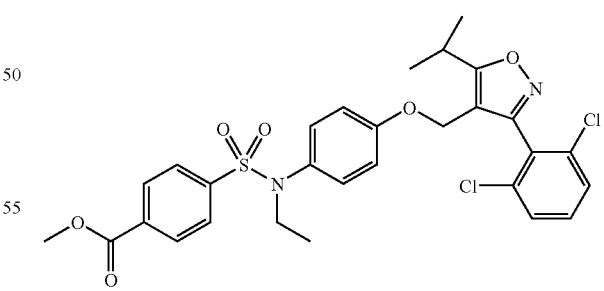

The title compound was prepared from appropriate starting materials using the synthesis described in Example 35.
¹H NMR (CDCl₃, 400 MHz) δ 8.10 (d, 2H), 7.65 (d, 2H), 7.42-7.38 (m, 2H), 7.36-7.30 (m, 1H), 6.84 (d, 2H), 6.68 (d, 2H), 4.70 (s, 2H), 3.96 (s, 3H), 3.54 (q, 2H), 3.36-3.25 (m, 1H), 1.41 (d, 6H), 1.04 (t, 3H); MS (ESP+) m/e 627 (M+Na⁺).

Example 62

4-{[(2-Chloro-4-{[3-(2,6-dichlorophenyl)-5-isopropylisoxazol-4-yl]methoxy}phenyl)-(methyl)amino]sulfonyl}benzoic acid

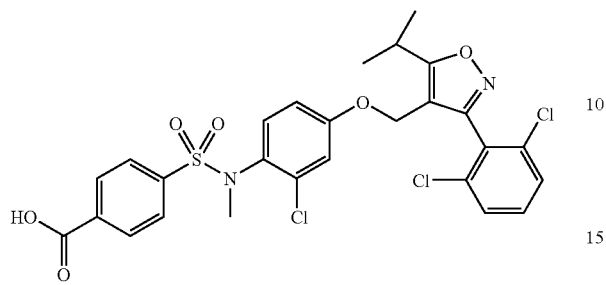

The title compound was prepared from appropriate starting materials using the synthesis described in Example 35.

$^1$H NMR (CDCl$_3$, 400 MHz) δ 8.21 (d, 2H), 7.84 (d, 2H), 7.43-7.38 (m, 2H), 7.37-7.31 (m, 1H), 7.09-7.04 (m, 1H), 6.79-6.75 (m, 1H), 6.67-6.62 (m, 1H), 4.70 (s, 2H), 3.36-3.24 (m, 1H), 3.20 (s, 3H), 1.42 (d, 6H); MS (AP+) m/e 611 (MH$^+$).

Example 63

4-{[(4-{[3-(2,6-Dichlorophenyl)-5-isopropylisoxazol-4-yl]methoxy}-2-methylphenyl)-(methyl)amino]sulfonyl}benzoic acid

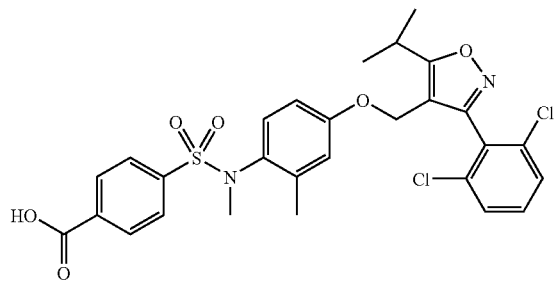

The title compound was prepared from appropriate starting materials using the synthesis described in Example 35.

$^1$H NMR (CDCl$_3$, 400 MHz) δ 8.23 (d, 2H), 7.80 (d, 2H), 7.43-7.38 (m, 2H), 7.36-7.29 (m, 1H), 6.68-6.64 (m, 1H), 6.45-6.37 (m, 2H), 4.68 (s, 2H), 3.37-3.26 (m, 1H), 3.12 (s, 3H), 2.29 (s, 3H), 1.42 (d, 6H); MS (ESP+) m/e 589 (M$^+$).

Example 64

4-{[(4-{[3-(2,6-Dichlorophenyl)-5-isopropylisoxazol-4-yl]methoxy}phenyl)(methyl)-amino]sulfonyl}benzoic acid

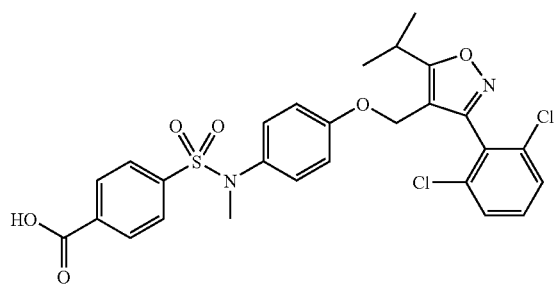

The title compound was prepared from appropriate starting materials using the synthesis described in Example 35.

$^1$H NMR (CDCl$_3$, 400 MHz) δ 8.17 (d, 2H), 7.64 (d, 2H), 7.42-7.38 (m, 2H), 7.36-7.30 (m, 1H), 6.92-6.88 (m, 2H), 6.70-6.65 (m, 2H), 4.71 (s, 2H), 3.37-3.26 (m, 1H), 3.14 (s, 3H), 1.42 (d, 6H); MS (ESP+) m/e 575 (M$^+$).

Example 65

4-{[(2-Chloro-4-{[3-(2,6-dichlorophenyl)-5-isopropylisoxazol-4-yl]methoxy}phenyl)-(ethyl)amino]sulfonyl}benzoic acid

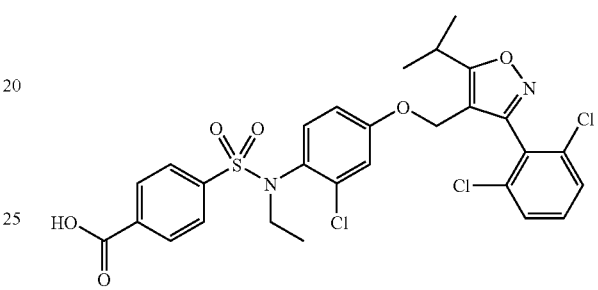

The title compound was prepared from appropriate starting materials using the synthesis described in Example 35.

$^1$H NMR (CDCl$_3$, 400 MHz) δ 8.18 (d, 2H), 7.82 (d, 2H), 7.44-7.39 (m, 2H), 7.37-7.31 (m, 1H), 7.05-7.00 (m, 1H), 6.80-6.76 (m, 1H), 6.68-6.62 (m, 1H), 4.71 (s, 2H), 3.75-3.48 (m, 2H), 3.37-3.25 (m, 1H), 1.43 (d, 6H), 1.08 (t, 3H); MS (ESP+) m/e 625 (MH$^+$).

Example 66

4-{[(4-{[3-(2,6-Dichlorophenyl)-5-isopropylisoxazol-4-yl]methoxy}-2-methylphenyl)-(ethyl)amino]sulfonyl}benzoic acid

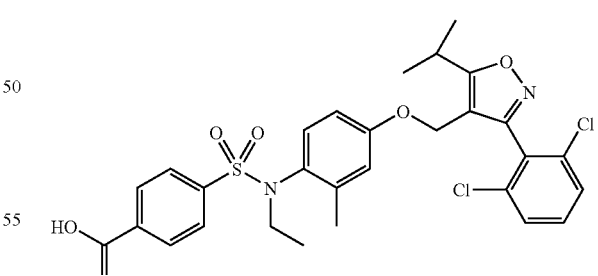

The title compound was prepared from appropriate starting materials using the synthesis described in Example 35.

$^1$H NMR (CDCl$_3$, 400 MHz) δ 8.20 (d, 2H), 7.77 (d, 2H), 7.43-7.38 (m, 2H), 7.36-7.30 (m, 1H), 6.69-6.65 (m, 1H), 6.48-6.43 (m, 1H), 6.40-6.35 (m, 1H), 4.69 (s, 2H), 3.83-3.72 (m, 1H), 3.38-3.21 (m, 2H), 2.27 (s, 3H), 1.42 (d, 6H), 1.03 (t, 3H); MS (ESP+) m/e 605 (MH$^+$).

Example 67

4-{[(4-{[3-(2,6-Dichlorophenyl)-5-isopropylisoxazol-4-yl]methoxy}phenyl)(ethyl)amino]-sulfonyl}benzoic acid

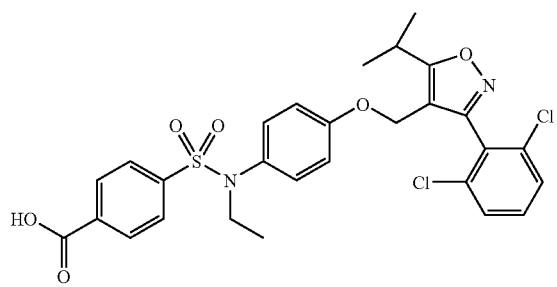

The title compound was prepared from appropriate starting materials using the synthesis described in Example 35.

$^1$H NMR (CDCl$_3$, 400 MHz) δ 8.17 (d, 2H), 7.69 (d, 2H), 7.43-7.38 (m, 2H), 7.36-7.30 (m, 1H), 6.86 (d, 2H), 6.69 (d, 2H), 4.71 (s, 2H), 3.56 (q, 2H), 3.37-3.26 (m, 1H), 1.42 (d, 6H), 1.06 (t, 3H); MS (ESP+) m/e 589 (M$^+$).

Example 68

3-({[2-Chloro-4-({5-isopropyl-3-[2-(trifluoromethoxy)phenyl]isoxazol-4-yl}methoxy)-phenyl]amino}sulfonyl)benzoic acid

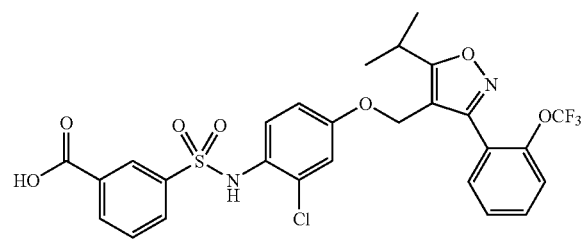

The title compound was prepared from appropriate starting materials using the synthesis described in Example 35.

$^1$H NMR (CDCl$_3$, 400 MHz) δ 8.49-8.42 (m, 1H), 8.28-8.19 (m, 1H), 7.86-7.78 (m, 1H), 7.55-7.44 (m, 3H), 7.39-7.31 (m, 2H), 6.83-6.73 (m, 1H), 6.68-6.55 (m, 2H), 4.73 (s, 2H), 3.31-3.19 (m, 1H), 1.36 (d, 6H); MS (ESP+) m/e 611 (MH$^+$).

Example 69

3-({[4-({5-Isopropyl-3-[2-(trifluoromethoxy)phenyl]isoxazol-4-yl}methoxy)-2-methyl-phenyl]amino}sulfonyl)benzoic acid

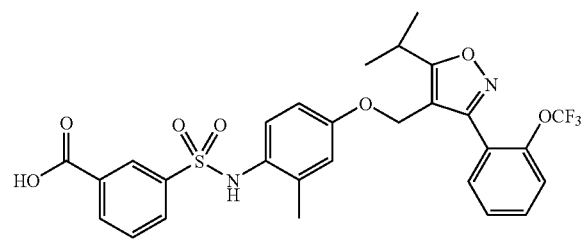

The title compound was prepared from appropriate starting materials using the synthesis described in Example 35.

$^1$H NMR (CDCl$_3$, 400 MHz) δ 8.56-8.47 (m, 1H), 8.27-8.18 (m, 1H), 7.81-7.69 (m, 1H), 7.56-7.44 (m, 3H), 7.39-7.30 (m, 2H), 6.96-6.87 (m, 1H), 6.53-6.41 (m, 2H), 4,72 (s, 2H), 3.32-3.20 (m, 1H), 1.90 (s, 3H), 1.36 (d, 6H); MS (ESP+) m/e 591 (MH$^+$).

Example 70

Methyl 3-{[[2-chloro-4-({5-isopropyl-3-[2-(trifluoromethoxy)phenyl]-isoxazol-4-yl}methoxy)phenyl](methyl)amino]sulfonyl}benzoate

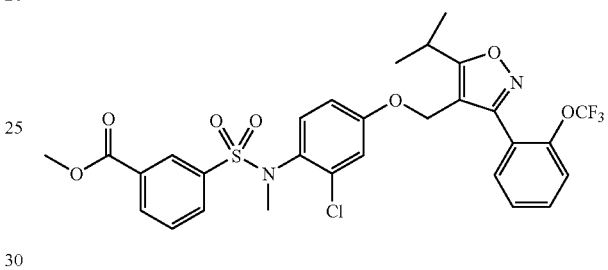

The title compound was prepared from appropriate starting materials using the synthesis described in Example 35.

$^1$H NMR (CDCl$_3$, 400 MHz) δ 8.46-8.41 (m, 1H), 8.27-8.22 (m, 1H), 7.93-7.87 (m, 1H), 7.60-7.48 (m, 3H), 7.42-7.34 (m, 2H), 7.11-7.06 (m, 1H), 6.79-6.75 (m, 6.67-6.62 (m, 1H), 4.74 (s, 2H), 3.93 (s, 3H), 3.34-3.22 (m, 1H), 3.19 (s, 3H), 1.40 (d, 6H); MS (ESP+) m/e 639 (M$^+$).

Example 71

Methyl 3-{[[4-({5-isopropyl-3-[2-(trifluoromethoxy)phenyl]isoxazol-4-yl}methoxy)-2-methylphenyl](methyl)amino]sulfonyl}benzoate

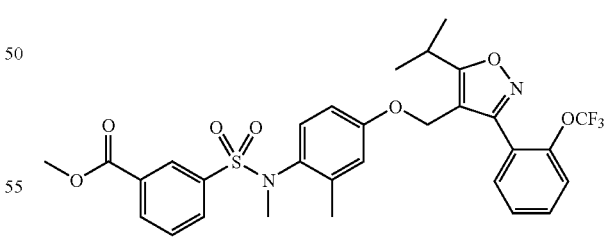

The title compound was prepared from appropriate starting materials using the synthesis described in Example 35.

$^1$H NMR (CDCl$_3$, 400 MHz) δ 8.41-8.38 (m, 1H), 8.29-8.24 (m, 1H), 7.86-7.81 (m, 1H), 7.61-7.48 (m, 3H), 7.41-7.34 (m, 2H), 6.68-6.64 (m, 1H), 6.47-6.39 (m, 2H), 4.73 (s, 2H), 3.93 (s, 3H), 3.34-3.23 (m, 1H), 3.11 (s, 3H), 2.29 (s, 3H); 1.39 (d, 6H); MS (ESP+) m/e 619 (M$^+$).

Example 72

3-{[[2-Chloro-4-({5-isopropyl-3-[2-(trifluoromethoxy)phenyl]isoxazol-4-yl}methoxy)-phenyl](methyl)amino]sulfonyl}benzoic acid

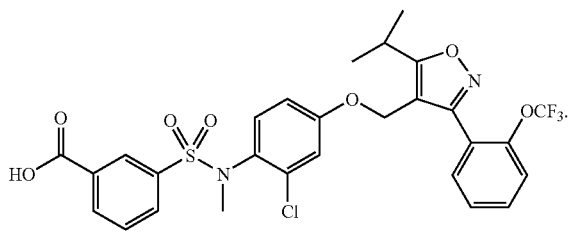

The title compound was prepared from appropriate starting materials using the synthesis described in Example 35.
$^1$H NMR (CDCl$_3$, 400 MHz) δ 8.50 (s, 1H), 8.31 (d, 1H), 7.97 (d, 1H), 7.62 (t, 1H), 7.56-7.50 (m, 2H), 7.41-7.36 (m, 2H), 7.12 (d, 1H), 6.78-6.77 (m, 1H), 6.67-6.64 (m, 1H), 4.75 (s, 2H), 3.31-3.25 (m, 1H), 3.20 (s, 3H), 1.39 (d, 6H); MS (ESP+) m/e 625 (M+).

Example 73

3-{[[4-({5-Isopropyl-3-[2-(trifluoromethoxy)phenyl]isoxazol-4-yl}methoxy)-2-methyl-phenyl](methyl)amino]sulfonyl}benzoic acid

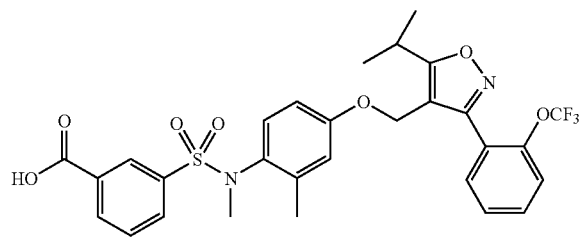

The title compound was prepared from appropriate starting materials using the synthesis described in Example 35.
$^1$H NMR (CDCl$_3$, 400 MHz) δ 8.46 (s, 1H), 8.32 (d, 1H), 7.89 (d, 1H), 7.63 (t, 1H), 7.56-7.49 (m, 2H), 7.40-7.36 (m, 2H), 6.66 (s, 1H), 6.45-6.42 (m, 2H), 4.74 (s, 2H), 3.33-3.25 (m, 1H), 3.12 (s, 3H), 2.30 (s, 3H), 1.38 (d, 6H); MS (ESP+) m/e 605 (M+H+).

Example 74

3-{[(4-{[3-(2,6-Dichlorobenzyl)-5-ethylisoxazol-4-yl]methoxy}-2-methylphenyl)(methyl)-amino]sulfonyl}benzoic acid

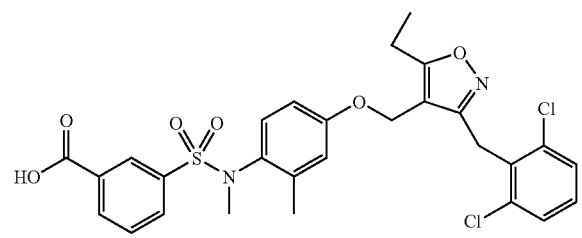

The title compound was prepared from appropriate starting materials using the synthesis described in Example 35.
$^1$H NMR (CDCl$_3$, 400 MHz) δ 8.48-8.45 (s, 1H), 8.36-8.31 (m, 1H), 7.96-7.92 (m, 1H), 7.65 (t, 1H), 7.29-7.25 (m, 2H), 7.11 (t, 1H), 6.83-6.79 (m, 1H), 6.60-6.55 (m, 1H), 6.51-6.47 (m, 1H), 4.78 (s, 2H), 4.32 (s, 2H), 3.16 (s, 3H), 2.77 (q, 2H), 2.37 (s, 3H), 1.27 (t, 3H); MS (ESP+) m/e 589 (M+).

Example 75

Methyl 4-[(2-chloro-4-{[3-(2,6-dichlorophenyl)-5-isopropylisoxazol-4-yl]methoxy}benzyl)oxy]benzoate a) 2-Chloro-4-{[3-(2,6-dichlorophenyl)-5-isopropylisoxazol-4-yl]methoxy}benzaldehyde.

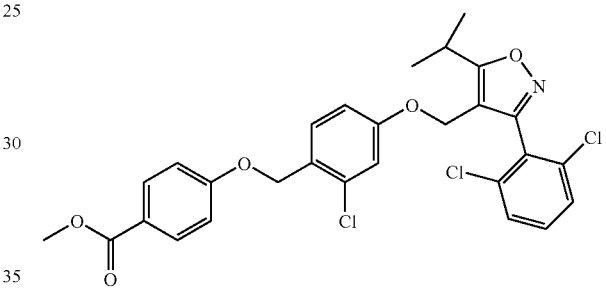

A mixture of 4-(chloromethyl)-3-(2,6-dichlorophenyl)-5-isopropylisoxazole (1 g, 3.28 mmol), 2-chloro-4-hydroxybenzaldehyde (498 mg, 3.18 mmol), potassium carbonate (431 mg, 3.12 mmol), sodium iodide (98 mg, 0.66 mmol) in acetone (20 mL) was refluxed for 5 h. The reaction was concentrated and the residue was partitioned with ethyl acetate and water. The organic layer was washed with brine, dried over anhydrous magnesium sulfate, filtered, and condensed to a residue which was chromatographed on silica gel eluting with 200% ethyl acetate/hexanes. Yield=0.98 g (71%) of 2-chloro-4-{[3-(2,6-dichlorophenyl)-5-isopropylisoxazol-4-yl]methoxy}-benzaldehyde.

b) (2-Chloro-4-{[3-(2,6-dichlorophenyl)-5-isopropylisoxazol-4-yl]methoxy}-phenyl)methanol.

A solution of 2-chloro-4-{[3-(2,6-dichlorophenyl)-5-isopropylisoxazol-4-yl]methoxy}benzaldehyde (50 mg, 120 μmol) in methanol (1.2 mL) was treated with sodium borohydride (4.5 mg, 119 μmol) and stirred at ambient temperature 1 h. The acetate. The filtrate was condensed to leave a residue. Yield=50 mg (98%) of (2-chloro-4-{[3-(2,6-dichlorophenyl)-5-isopropylisoxazol-4-yl]methoxy}phenyl)-methanol.

c) 4-{[3-Chloro-4-(chloromethyl) phenoxy]methyl}-3-(2,6-dichlorophenyl)-5-isopropylisoxazole.

To a solution of (2-chloro-4-{[3-(2,6-dichlorophenyl)-5-isopropylisoxazol-4-yl]methoxy}phenyl)methanol (50 mg, 120 μmol) in dichloromethane (0.35 mL) was added thionyl chloride (10 μL, 140 μmol) and the mixture was let stir 2.5 hours. The solvent was removed in vacuo to leave a residue. Yield=53 mg (100%) of 4-{[3-chloro-4-(chloromethyl)phenoxy]methyl}-3-(2,6-dichlorophenyl)-5-isopropylisoxazole.

d) Methyl 4-[(2-chloro-4-{[3-(2,6-dichlorophenyl)-5-isopropylisoxazol-4-yl]methoxy}benzyl)oxy]benzoate A mixture of 4-{[3-chloro-4-(chloromethyl)phenoxy]methyl}-3-(2,6-dichlorophenyl)-5-isopropylisoxazole (50 mg, 112 μmol), potassium carbonate (16.9 mg, 122 μmol), sodium iodide (18.3 mg, 110 μmol), and methyl 4-hydroxybenzoate (16.7 mg, 110 μmol) in dimethylformamide (0.6 mL) was stirred at ambient temperature overnight. The mixture was filtered, condensed to a residue, and was chromatographed on silica gel eluting with 33% ethyl acetate/hexanes. Yield=41 mg (65%) of methyl 4-[(2-chloro-4-{[3-(2,6-dichlorophenyl)-5-isopropylisoxazol-4-yl]methoxy}benzyl)oxy]-benzoate.

Example 76

Methyl 3-[(2-chloro-4-{[3-(2,6-dichlorophenyl)-5-isopropylisoxazol-4-yl]methoxy}benzyl)-oxy]benzoate

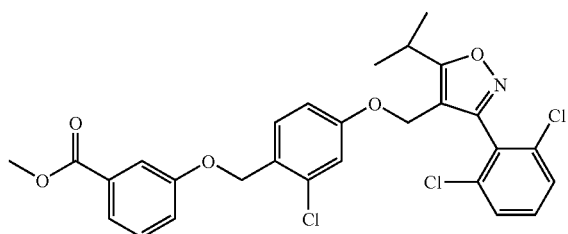

The title compound was prepared from appropriate starting materials using the synthesis described in Example 75.

$^1$H NMR (CDCl$_3$, 400 MHz) δ 7.66-7.62 (m, 2H), 7.41-7.38 (m, 2H), 7.37-7.28 (m, 3H), 7.16-7.12 (m, 1H), 6.83-6.81 (m, 1H), 6.71-6.67 (m, 1H), 5.09 (s, 2H), 4.71 (s, 2H), 3.91 (s, 3H), 3.37-3.25 (m, 1H), 1.42 (d, 6H); MS (ESP+) m/e 584 (M+Na$^+$).

Example 77

3-[(2-Chloro-4-{[3-(2,6-dichlorophenyl)-5-isopropylisoxazol-4-yl]methoxy}benzyl)oxy]-benzoic acid

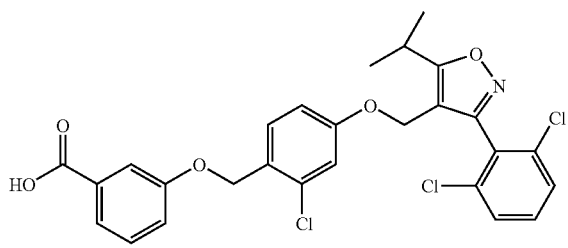

The title compound was prepared from appropriate starting materials using the synthesis described in Example 75.

$^1$H NMR (CDCl$_3$, 400 MHz) δ 7.74-7.68 (m, 2H), 7.41-7.36 (m, 3H), 7.36-7.29 (m, 2H), 7.22-7.18 (m, 1H), 6.84-6.82 (m, 1H), 6.72-6.68 (m, 1H), 5.10 (s, 2H), 4.72 (s, 2H), 3.37-3.25 (m, 1H), 1.42 (d, 6H); MS (ESP+) m/e 548 (M+H$^+$).

Example 78

3-[(2-Chloro-4-{[3-(2,6-dichlorophenyl)-5-isopropylisoxazol-4-yl]methoxy}benzyl)thio]-benzoic acid

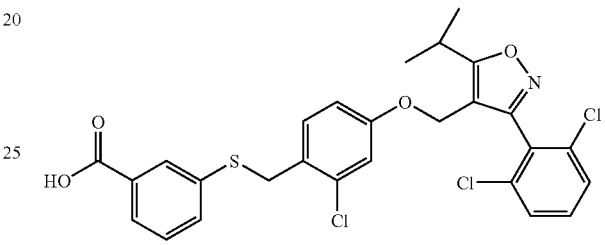

The title compound was prepared from appropriate starting materials using the synthesis described in Example 75.

$^1$H NMR (CDCl$_3$, 400 MHz) δ 8.08-8.05 (m,1H), 7.94-7.89 (m, 1H), 7.53-7.47 (m, 1H), 7.42-7.34 (m, 3H), 7.34-7.28 (m, 1H), 7.13-7.08 (m, 1H), 6.79-6.76 (m, 1H), 6.60-6.54 (m, 1H), 4.69 (s, 2H), 4.18 (s, 2H), 3.35-3.23 (m, 1H), 1.40 (d, 6H); MS (ESP+) m/e 564 (M+H$^+$).

Example 79

3-[(4-{[3-(2,6-Dichlorophenyl)-5-isopropylisoxazol-4-yl]methoxy}-2-methylbenzyl)oxy]-benzoic acid

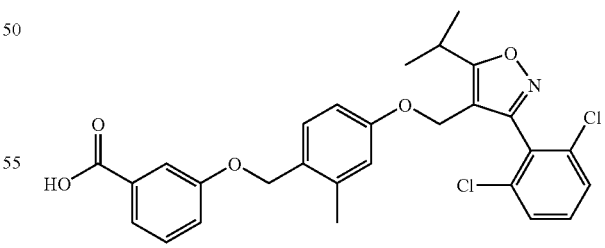

The title compound was prepared from appropriate starting materials using the synthesis described in Example 75.

$^1$H NMR (CDCl$_3$, 400 MHz) δ 7.72-7.68 (m, 2H), 7.40-7.35 (m, 3H), 7.32-7.22 (m, 1H), 7.24-7.17 (m, 2H), 6.64-6.60 (m, 2H), 4.98 (s, 2H), 4.70 (s, 2H), 3.35-3.26 (m, 1H), 2.31 (s, 3H), 1.41 (d, 6H); MS (ESP+) m/e 526 (M$^+$).

Example 80

3-[(4-{[3-(2,6-Dichlorophenyl)-5-isopropylisoxazol-4-yl]methoxy}-2-methylbenzyl)thio]-benzoic acid

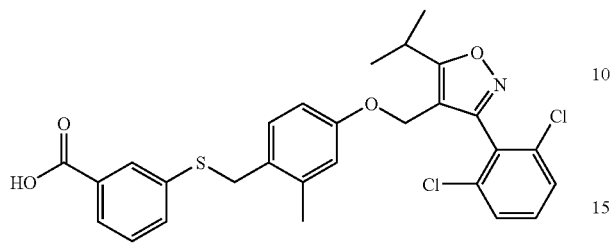

The title compound was prepared from appropriate starting materials using the synthesis described in Example 75.
$^1$H NMR (CDCl$_3$, 400 MHz) δ 8.04 (s, 1H), 7.91-7.89 (m, 1H), 7.49-7.47 (m, 1H), 7.39-7.35 (m, 3H), 7.33-7.28 (m, 1H), 7.02-7.00 (m, 1H), 6.59-6.58 (m, 1H), 6.52-6.49 (m, 1H), 4.68 (s, 2H), 4.08 (s, 2H), 3.34-3.25 (m, 1H), 2.33 (s, 3H), 1.40 (d, 6H); MS (ESP+) m/e 542 (M$^+$).

Example 81

4-[(2-Chloro-4-{[3-(2,6-dichlorophenyl)-5-isopropylisoxazol-4-yl]methoxy}benzyl)oxy]benzoic acid

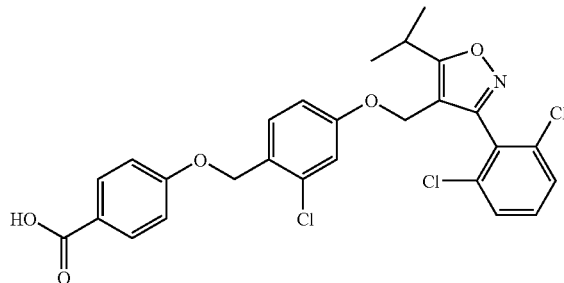

The title compound was prepared from appropriate starting materials using the synthesis described in Example 75.
$^1$H NMR (CDCl$_3$, 400 MHz) δ 8.05 (d, 2H), 7.41-7.37 (m, 2H), 7.35-7.29 (m, 2H), 6.99 (d, 2H), 6.84-6.82 (m, 1H), 6.72-6.67 (m, 1H), 5.12 (s, 2H), 4.71 (s, 2H), 3.37-3.25 (m, 1H), 1.42 (d, 6H); MS (ESP+) m/e 546 (M$^+$).

Example 82

4-[(2-Chloro-{[3-(2,6-dichlorophenyl)-5-isopropyl-isoxazol-4-yl]methoxy}benzyl)thio]-benzoic acid

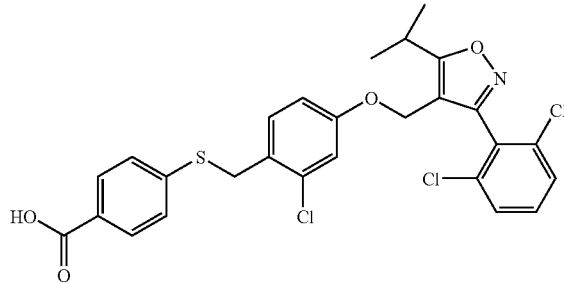

The title compound was prepared from appropriate starting materials using the synthesis described in Example 75.
$^1$H NMR (CDCl$_3$, 400 MHz) δ 7.96 (d, 2H), 7.41-7.37 (m, 2H), 7.34-7.28 (m, 3H), 7.23-7.19 (m, 1H), 6.81-6.78 (m, 1H), 6.62-6.58 (m, 1H), 4.69 (s, 2H), 4.23 (s, 2H), 3.35-3.24 (m, 1H), 1.41 (d, 6H); MS (ESP+) m/e 562 (M$^+$).

Example 83

Methyl 3-{[2-chloro-4-({5-isopropyl-3-[2-(trifluoromethoxy)-phenyl]isoxazol-4-yl}methoxy)benzyl]oxy}benzoate

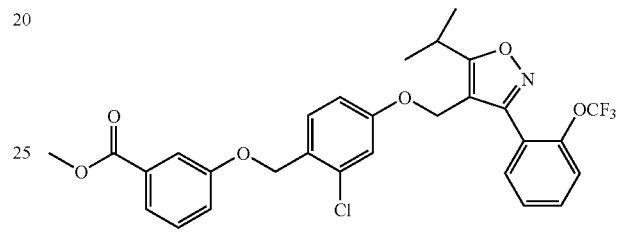

The title compound was prepared from appropriate starting materials using the synthesis described in Example 75.
$^1$H NMR (CDCl$_3$, 400 MHz) δ 7.67-7.63 (m, 2H), 7.58-7.48 (m, 2H), 7.41-7.31 (m, 4H), 7.17-7.12 (m, 1H), 6.83-6.81 (m, 1H), 6.72-6.68 (m, 1H), 5.09 (s, 2H), 4.77 (s, 2H), 3.91 (s, 3H), 3.35-3.23 (m, 1H), 1.40 (d, 6H); MS (ESP+) m/e 576 (M+H$^+$).

Example 84

Methyl 3-{[4-({5-isopropyl-3-[2-(trifluoromethoxy)phenyl]isoxazol-4-yl}methoxy)-2-methylbenzyl]oxy}benzoate

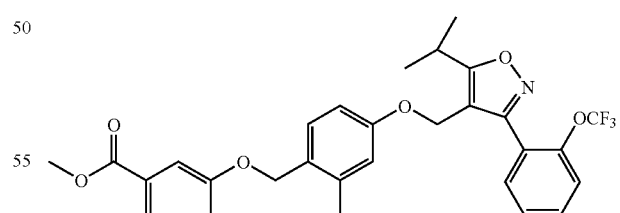

The title compound was prepared from appropriate starting materials using the synthesis described in Example 75.
$^1$H NMR (CDCl$_3$, 400 MHz) δ 7.66-7.62 (m, 2H), 7.60-7.56 (m, 1H), 7.53-7.47 (m, 1H), 7.40-7.31 (m, 3H), 7.27-7.22 (m, 1H), 7.16-7.12 (m, 1H), 6.66-6.60 (m, 2H), 4.97 (s, 2H), 4.77 (s, 2H), 3.91 (s, 3H), 3.36-3.24 (m,1H), 2.30 (s, 3H); 1.40 (d, 6H); MS (ESP+)m/e 556 (M+H$^+$).

Example 85

3-{[2-Chloro-4-({5-isopropyl-3-[2-(trifluoromethoxy)phenyl]isoxazol-4-yl}methoxy)-benzyl]oxy}benzoic acid

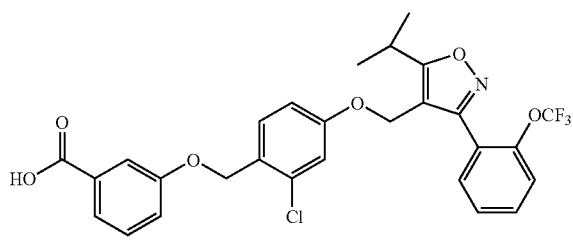

The title compound was prepared from appropriate starting materials using the synthesis described in Example 75.
$^1$H NMR (CDCl$_3$, 400 MHz) δ 7.75-7.69 (m, 2H), 7.59-7.49 (m, 2H), 7.42-7.35 (m, 4H), 7.23-7.19 (m, 1H), 6.85-6.82 (m, 1H), 6.73-6.69 (m, 1H), 5.12 (s, 2H), 4.78 (s, 2H), 3.35-3.24 (m, 1H), 1.41 (d, 6H); MS (ESP+) m/e 562 (M+H$^+$).

Example 86

3-{[4-({5-Isopropyl-3-[2-(trifluoromethoxy)phenyl]isoxazol-4-yl}methoxy)-2-methyl-benzyl]oxy}benzoic acid

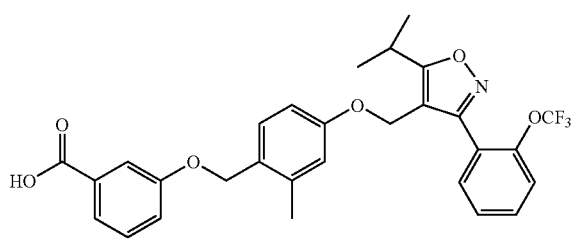

The title compound was prepared from appropriate starting materials using the synthesis described in Example 75.
$^1$H NMR (CDCl$_3$, 400 MHz) δ 7.74-7.70 (m, 2H), 7.60-7.56 (m, 1H), 7.53-7.47 (m, 1H), 7.41-7.36 (m, 3H), 7.27-7.19 (m, 2H), 6.65-6.62 (m, 2H), 5.00 (s, 2H), 4.78 (s, 2H), 3.37-3.25 (m, 1H), 2.32 (s, 3H), 1.40 (d, 6H); MS (ESP+) m/e 542 (M+H$^+$).

Example 87

3-[(2-Chloro-4-{[3-(2,6-dichlorobenzyl)-5-ethylisoxazol-4-yl]methoxy}benzyl)oxy]benzoic acid

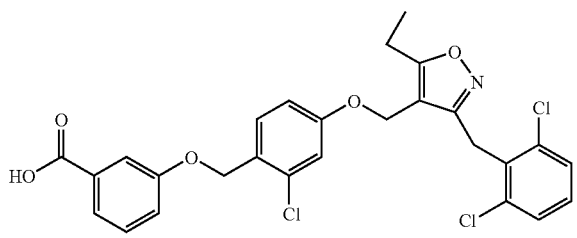

The title compound was prepared from appropriate starting materials using the synthesis described in Example 75.
$^1$H NMR (CDCl$_3$, 400 MHz) δ 7.76-7.71 (m, 2H), 7.46-7.38 (m, 2H), 7.28-7.21 (m, 3H), 7.12-7.07 (m, 1H), 6.97-6.94 (m, 1H), 6.84-6.81 (m, 1H), 5.16 (s, 2H), 4.79 (s, 2H), 4.33 (s, 2H), 2.78 (q, 2H), 1.28 (t, 3H); MS (AP+) m/e 548 (M+H$^+$).

Example 88

Methyl 3-{[2-chloro-4-({5-isopropyl-3-[2-(trifluoromethoxy)phenyl]isoxazol-4-yl}methoxy)benzyl]thio}benzoate

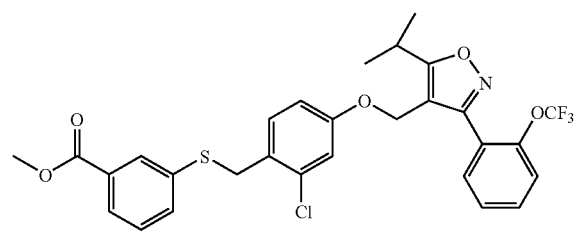

The title compound was prepared from appropriate starting materials using the synthesis described in Example 75.
$^1$H NMR (CDCl$_3$, 400 MHz) δ 8.01-7.99 (m, 1H), 7.87-7.83 (m, 1H), 7.57-7.48 (m, 2H), 7.46-7.42 (m, 1H), 7.40-7.34 (m, 2H), 7.33-7.28 (m, 1H), 7.12-7.08 (m, 1H), 6.79-6.75 (m, 1H), 6.59-6.55 (m, 1H), 4.74 (s, 2H), 4.17 (s, 2H), 3.90 (s, 3H), 3.33-3.22 (m, 1H), 1.39 (d, 6H); MS (ESP+) m/e 593 (M+H$^+$).

Example 89

Methyl 3-{[4-({5-isopropyl-3-[2-(trifluoromethoxy)phenyl]isoxazol-4-yl}methoxy)-2-methylbenzyl]thio}benzoate

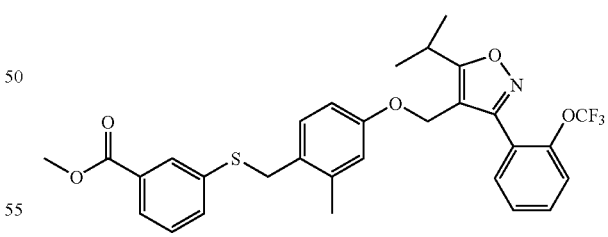

The title compound was prepared from appropriate starting materials using the synthesis described in Example 75.
$^1$H NMR (CDCl$_3$, 400 MHz) δ 8.00-7.98 (m, 1H), 7.86-7.82 (m, 1H), 7.58-7.54 (m, 1H), 7.53-7.41 (m, 2H), 7.40-7.34 (m, 2H), 7.34-7.28 (m, 1H), 7.04-7.00 (m, 1H), 6.60-6.56 (m, 1H), 6.54-6.49 (m, 1H), 4.74 (s, 2H), 4.08 (s, 2H), 3.90 (s, 3H), 3.35-3.23 (m, 1H), 2.32 (s, 3H), 1.39 (d, 6H); MS (ESP+) m/e 572 (M+H$^+$).

Example 90

3-{[2-Chloro-4-({5-isopropyl-3-[2-(trifluoromethoxy)phenyl]isoxazol-4-yl}methoxy)-benzyl]thio}benzoic acid

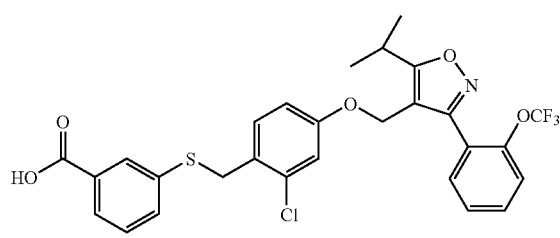

The title compound was prepared from appropriate starting materials using the synthesis described in Example 75.

$^1$H NMR (CDCl$_3$, 400 MHz) δ 8.06 (s, 1H), 7.94-7.89 (m, 1H), 7.57-7.47 (m, 3H), 7.39-7.33 (m, 3H), 7.14-7.09 (m, 1H), 6.79-6.76 (m, 1H), 6.60-6.55 (m, 1H), 4.74 (s, 2H), 4.19 (s, 2H), 3.33-3.22 (m, 1H), 1.39 (d, 6H); MS (ESP+) m/e 579 (M+H$^+$).

Example 91

3-{[4-({5-Isopropyl-3-[2-(trifluoromethoxy)phenyl]isoxazol-4-yl}methoxy)-2-methyl-benzyl]thio}benzoic acid

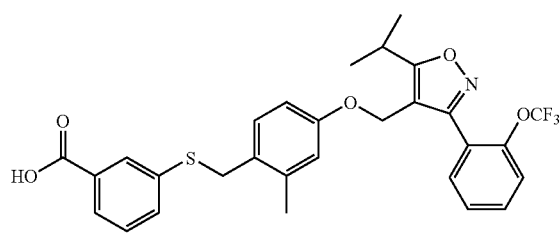

The title compound was prepared from appropriate starting materials using the synthesis described in Example 75.

$^1$H NMR (CDCl$_3$, 400 MHz) δ 8.06 (m, 1H), 7.94-7.89 (m, 1H), 7.58-7.54 (m, 1H), 7.53-7.47 (m, 2H), 7.40-7.32 (m, 3H), 7.06-7.00 (m, 1H), 6.61-6.57 (m, 1H), 6.54-6.50 (m, 1H), 4.74 (s, 2H), 4.10 (s, 2H), 3.35-3.23 (m, 1H), 2.33 (s, 3H), 1.39 (d, 6H); MS (ESP+) m/e 558 (M+H$^+$).

Example 92

Methyl 3-[(2-chloro-4-{[3-(2,6-dichlorophenyl)-5-isopropylisoxazol-4-yl]methoxy}benzyl)(methyl)amino]benzoate

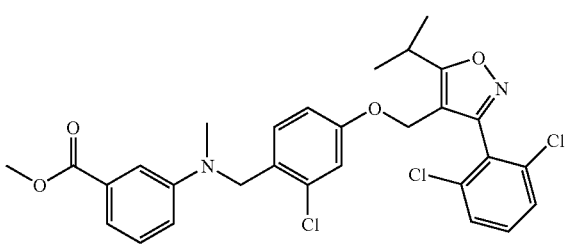

The title compound was prepared from appropriate starting materials using the synthesis described in Example 75.

$^1$H NMR (CDCl$_3$, 400MHz) δ 7.40 (d, 1H), 7.37 (m, 3H), 7.31 (m, 1H), 7.24 (m, 1H), 6.91 (d, 1H), 6.83 (d, 1H), 6.78 (dd, 1H), 6.57 (dd, 1H), 4.69 (s, 2H), 4.52 (s, 2H), 3.88 (s, 3H), 3.31 (m, 1H), 3.06 (s, 3H), 1.42 (d, 6H); MS (ESP+) m/e 595 (M+Na$^+$).

Example 93

3-[(2-Chloro-4-{[3-(2,6-dichlorophenyl)-5-isopropylisoxazol-4-yl]methoxy}benzyl)(methyl)amino]benzoic acid

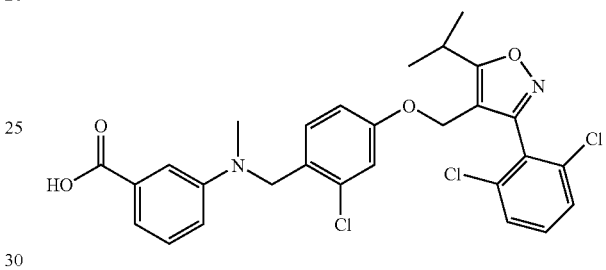

The title compound was prepared from appropriate starting materials using the synthesis described in Example 75.

$^1$H NMR (CDCl$_3$, 400 MHz) δ 7.41 (m, 4H), 7.28(m, 2H), 6.91 (d, 1H), 6.84 (m, 2H), 6.58 (dd, 1H), 4.69 (s, 2H), 4.53 (s, 2H), 3.30 (m, 1H), 3.07 (s, 3H), 1.41 (d, 6H); MS (ESP+) m/e 559 (MH$^+$).

Example 94

3-[(2-Chloro-4-{[3-(2,6-dichlorophenyl)-5-isopropylisoxazol-4-yl]methoxy}benzyl)amino]benzoic acid

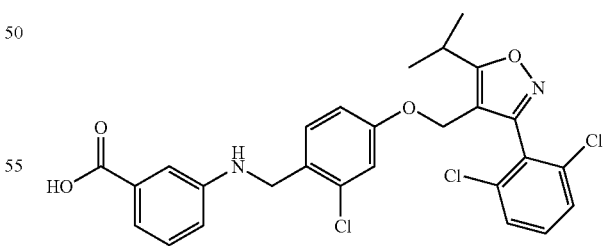

The title compound was prepared from appropriate starting materials using the synthesis described in Example 75.

$^1$H NMR (CDCl$_3$, 400MHz) δ 7.16-7.49 (m, 7H), 6.80 (m, 2H), 6.62 (dd, 1H), 4.70 (s, 2H), 4.36 (s, 2H), 3.31 (m, 1H), 1.41 (d, 6H); MS (ESP+) m/e 567 (M+Na$^+$).

Example 95

Ethyl 3-{[2-chloro-4-({5-isopropyl-3-[2-(trifluoromethoxy)phenyl]-4-isoxazolyl}methoxy)benzyl]amino}benzoate

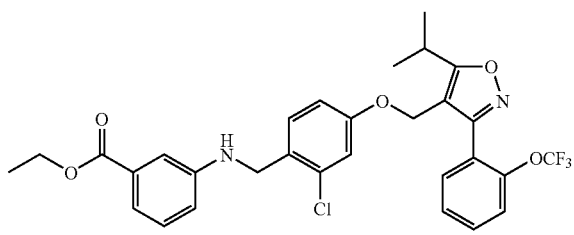

The title compound was prepared from appropriate starting materials using the synthesis described in Example 75.
$^1$HNMR (CDCl$_3$, 400 MHz) δ 7.56 (d, 1H, J=7.64), 7.51 (m, 1H), 7.37 (m, 3H), 7.31 (s, 1H), 7.21 (m, 2H), 6.80 (d, 1H, J=2.57), 6.76 (d, 1H, J=7.95), 6.63 (dd, 1H, J=8.56), 4.75 (s, 2H), 4.37 (s, 2H), 4.33 (q, 2H, J=7.08), 3.28 (m, 1H), 1.39 (d, 6H, J=7.09), 1.36 (t,3H, J=7.19); MS (ESP+) m/e 589 (M).

Example 96

3-{[2-Chloro-4-({5-isopropyl-3-[2-(trifluoromethoxy)phenyl]-4-isoxazolyl}methoxy)benzyl]amino}benzoic acid

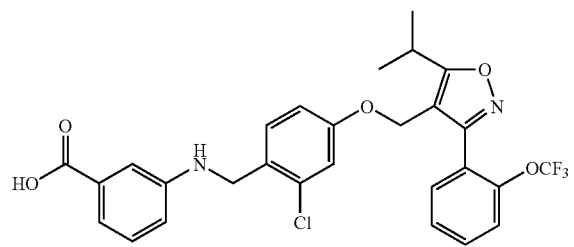

The title compound was prepared from appropriate starting materials using the synthesis described in Example 75.
$^1$HNMR (CDCl$_3$, 400 MHz) δ 7.55 (d, 1H, J=7.46), 7.50 (t, 1H, J=7.76), 7.42 (d, 1H, J=7.61), 7.35 (m, 3H), 7.20 (m, 2H), 6.80 (d, 1H, J=2.53), 6.76 (d, 1H, J=8.51), 6.62 (dd, 1H, J=8.65), 4.75 (s, 2H), 4.34 (s, 2H), 3.28 (m, 1H), 1.38 (d, 6H, J=6.95); MS (ESP+) m/e 561 (M).

Example 97

3-[[2-Chloro-4-({5-isopropyl-3-[2-(trifluoromethoxy)phenyl]-4-isoxazolyl}methoxy)benzyl](methyl)amino]benzoic acid

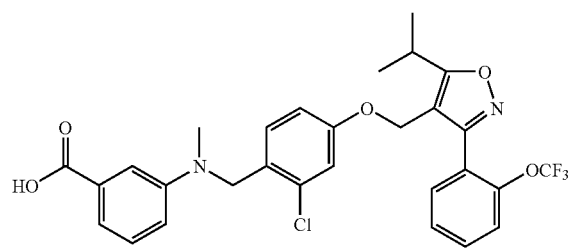

The title compound was prepared from appropriate starting materials using the synthesis described in Example 75.
$^1$HNMR (CDCl$_3$, 400 MHz) δ 7.56 (d, 1H, J=7.68), 7.50 (m, 1H), 7.40 (m, 4H), 7.27 (m, 2H), 6.94 (d, 1H, J=8.64), 6.83 (d, 1H, J=2.62), 6.59 (dd, 1H, J=8.64), 4.74 (s, 2H), 4.54 (s, 2H), 3.2.8 (m, 1H), 3.08 (s, 3H), 1.39 (d, 6H, J=7.02); MS (ESP+) m/e 575 (M).

Example 98

Methyl 4-[(4-{[3-(2,6-dichlorophenyl)-5-isopropylisoxazol-4-yl]methoxy}-2-methylphenoxy)methyl]benzoate

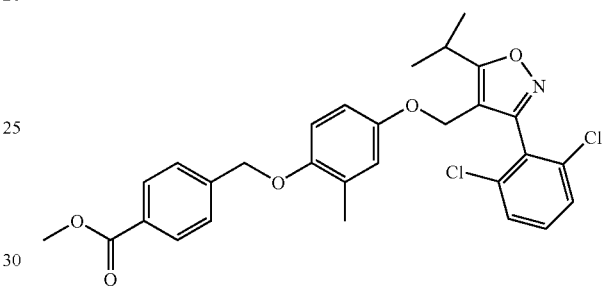

a) 1-(4-{[3-(2,6-Dichlorophenyl)-5-isopropylisoxazol-4-yl]methoxy}-2-methylphenyl)ethanone A mixture of 4-(chloromethyl)-3-(2,6-dichlorophenyl)-5-isopropylisoxazole (104 mg, 340 μmol), 2-methyl-4hydroxyacetophenone (50 mg, 330 μmol), potassium carbonate (45 mg, 320 μmol), sodium iodide (9.9 mg, 66 μmol) in acetone (2.2 mL) was refluxed for 5 h. The reaction was filtered over a plug of silica gel, rinsed with ethyl acetate and condensed to a residue. Yield=138 mg (100%) of 1-(4-{[3-(2,6-dichlorophenyl)-5-isopropylisoxazol-4-yl]methoxy}-2-methylphenyl)ethanone.

b) 4-{[3-(2,6-Dichlorophenyl)-5-isopropylisoxazol-4-yl]methoxy}-2-methylphenyl acetate A mixture of 1-(4-{[3-(2,6-dichlorophenyl)-5-isopropylisoxazol-4-yl]methoxy}-2-methylphenyl)ethanone (138 mg, 330 μmol), 3-chloroperoxybenzoic acid (100 mg, 580 μmol), 4-toluylsulfonic acid (6.6 mg, 35 μmol) in dichloromethane (1.7 mL) was refluxed for 3 hours. After cooling to ambient temperature, the reaction was diluted with dichloromethane (5 mL), was washed with aqueous potassium iodide followed by saturated aqueous sodium bicarbonate (2×5 mL). The organic layer was dried over anhydrous sodium sulfate, filtered, and condensed to a residue. Yield=142 mg (99%) of 4-{[3-(2,6-dichlorophenyl)-5-isopropylisoxazol-4-yl]methoxy}-2-methylphenyl acetate.

c) 4-{[3-(2,6-Dichlorophenyl)-5-isopropylisoxazol-4-yl]methoxy}-2-methylphenol A solution of 4-{[3-(2,6-dichlorophenyl)-5-isopropyl-isoxazol-4-yl]methoxy}-2-methylphenyl acetate (140 mg, 320 µmol) in methanol (2.9 mL) was treated with 0.5M solution of sodium methoxide in methanol (640 µL 320 µmol) and was stirred for 1.5 h. The reaction was neutralized with 1N hydrochloric acid (320 µL, 320 µmol) and the slovent was evaporated. The resulting residue was dissolved in dichloromethane (6 mL), washed with water (2×6 mL), the organic phase was then dried over anhydrous magnesium sulfate, filtered, and condensed to a residue. Yield=122 mg (97%) of 4-{[3-(2,6-dichlorophenyl)-5-isopropylisoxazol-4-yl]methoxy}-2-methylphenol.

d) Methyl 4-[(4-{([3-(2,6-Dichlorophenyl)-5-isopropylisoxazol-4-yl]methoxy}-2-methylphenoxy)methyl]benzoate A mixture of 4-{[3-(2,6-dichlorophenyl)-5-isopropylisoxazol-4-yl]methoxy}-2-methylphenol (40 mg, 102 µmol), methyl 4-bromomethylbenzoate (24.6 mg, 105 µmol), potassium carbonate (42.3 mg, 306 µmol) in acetone (1 mL) was heated at 50° C. overnight. The mixture was filtered through a plug of silica gel, rinsing with acetone, and the filtrate condensed to leave a residue which was chromatographed on silica gel eluting with 33% ethyl acetate/hexanes. Yield=37 mg (67%) of methyl 4-[(4-{[3-(2,6-dichlorophenyl)-5-isopropylisoxazol-4-yl]methoxy}-2-methylphenoxy)methyl]benzoate.

Example 99

Methyl 3-[(2-chloro-4-{[3-(2,6-dichlorophenyl)-5-isopropylisoxazol-4-yl]methoxy}-phenoxy)methyl]benzoate

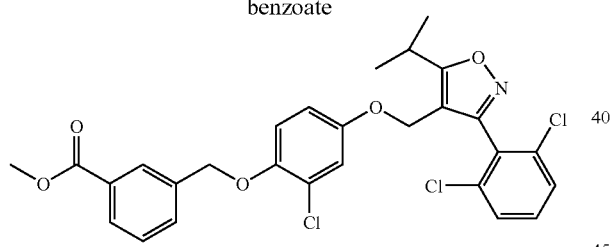

The title compound was prepared from appropriate starting materials using the synthesis described in Example 98.

$^1$H NMR (CDCl$_3$, 400 MHz) δ 8.08 (s, 1H), 7.98 (d, 1H), 7.65 (d, 1H), 7.45 (t, 1H), 7.41-7.37 (m, 2H), 7.34-7.28 (m, 1H), 6.82-6.77 (m, 2H), 6.59-6.55 (m,1H), 5.08 (s, 2H), 4.65 (s, 2H), 3.91 (s, 3H), 3.34-3.22 (m, 1H), 1.40 (d, 6H); MS (ESP+) m/e 562 (M+H$^+$).

Example 100

Methyl 3-[(4-{[3-(2,6-dichlorophenyl)-5-isopropyl-isoxazol-4-yl]methoxy}-2-methyl-phenoxy)methyl]benzoate

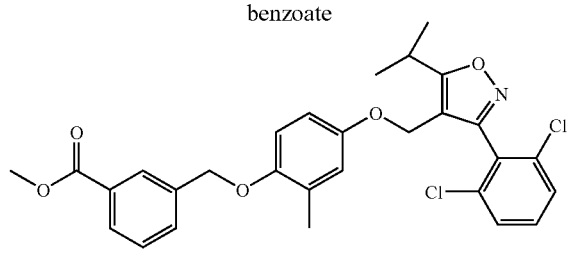

The title compound was prepared from appropriate starting materials using the synthesis described in Example 98.

$^1$H NMR (CDCl$_3$, 400 MHz) δ 8.08 (s, 1H), 7.98 (d, 1H), 7.62 (d, 1H), 7.45 (t, 1H), 7.41-7.37 (m, 2H), 7.33-7.28 (m, 1H), 6.72-6.67 (m, 1H), 6.62-6.59 (m, 1H), 6.55-6.50 (m, 1H), 5.02 (s, 2H), 4.65 (s, 2H), 3.92 (s, 3H), 3.36-3.24 (m, 1H), 2.21 (s, 3H), 1.40 (d, 6H); MS (ESP+) m/e 540 (M$^+$).

Example 101

3-[(2-Chloro-4-{[3-(2,6-dichlorophenyl)-5-isopropylisoxazol-4-yl]methoxy}phenoxy)-methyl]benzoic acid

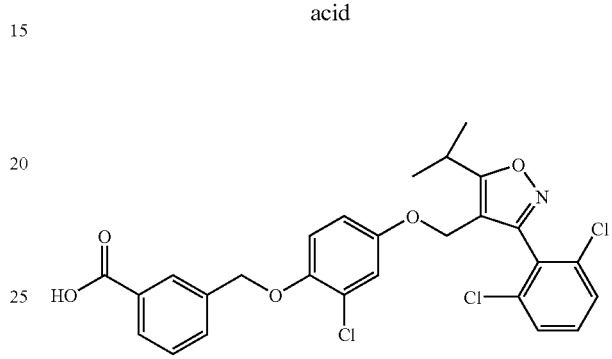

The title compound was prepared from appropriate starting materials using the synthesis described in Example 98.

$^1$H NMR (CDCl$_3$, 400 MHz) δ 8.16 (s, 1H), 8.07 (d, 1H), 7.73 (d, 1H), 7.50 (t, 1H), 7.41-7.38 (m, 2H), 7.34-7.29 (m, 1H), 6.82-6.79 (m, 2H), 6.61-6.57 (m, 1H), 5.11 (s, 2H), 4.67 (s, 2H), 3.32-3.25 (m, 1H), 1.40 (d, 6H); MS (ESP+) m/e 548 (M+H$^+$).

Example 102

3-[(4-{[3-(2,6-Dichlorophenyl)-5-isopropylisoxazol-4-yl]methoxy}-2-methylphenoxy)-methyl]benzoic acid

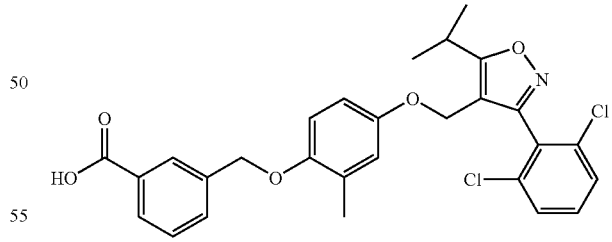

The title compound was prepared from appropriate starting materials using the synthesis described in Example 98.

$^1$H NMR (CDCl$_3$, 400 MHz) δ 8.15 (s, 1H), 8.06 (d, 1H), 7.68 (d, 1H), 7.49 (t, 1H), 7.41-7.37 (m, 2H), 7.34-7.28 (m, 1H), 6.72-6.69 (m, 1H), 6.62-6.60 (m, 1H), 6.56-6.51 (m, 1H), 5.05 (s, 2H), 4.66 (s, 2H), 3.36-3.24 (m, 1H), 2.22 (s, 3H), 1.40 (d, 6H); MS (ESP+) m/e 526 (M$^+$).

Example 103

Methyl 4-[(4-{[3-(2,6-dichlorophenyl)-5-isopropyl-isoxazol-4-yl]methoxy}-2-methyl-phenoxy)methyl]benzoate

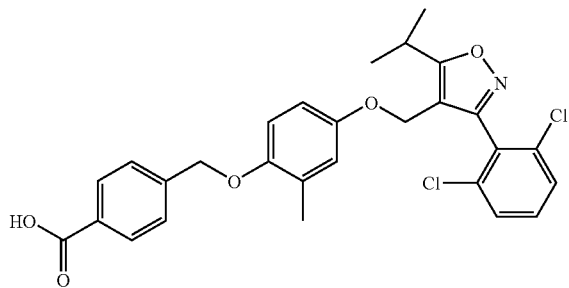

The title compound was prepared from appropriate starting materials using the synthesis described in Example 98.

$^1$H NMR (CDCl$_3$, 400 MHz) δ 8.11 (d, 2H), 7.52 (d, 2H), 7.41-7.37 (m, 2H), 7.34-7.28 (m, 1H), 6.70-6.65 (m, 1H), 6.63-6.60 (m, 1H), 6.55-6.49 (m, 1H), 5.07 (s, 2H), 4.65 (s, 2), 3.35-3.24 (m, 1H), 2.23 (s, 3H), 1.40 (d, 6H); MS (ESP+) m/e 526 (M$^+$).

Example 104

Biological Example

Determination of a ligand mediated cofactor peptide interaction to quantify ligand binding to the nuclear receptor Farnasoid X Receptor (FXR). The method measures the ability of putative ligands to modulate the interaction between the purified bacterial expressed FXRα (LBD) and a synthetic biotinylated peptide based on residues 676-700 of SRC-1(LCD2, 676-700). The sequence of the peptide used was B-CPSSHSSLTERHKILHRLLQEGSPS-CONH2 where the N-terminus was biotinylated (B) and the C-terminus was amidated. Detection of the associated complex is measured by time resolved fluorescence (TRF). The purified LBD of FXR is labeled with biotin then mixed with stoichiometric amounts of APC labeled streptavidin (Molecular Probes). The biotinylated peptide is then mixed with a ½ stoichiometric amount of europium labeled streptavidin (Wallac Inc). Each is then blocked with a 5 fold excess of biotin and allowed to equilibrate for 15 min. Equimolar amounts of receptor and peptide are mixed together and allowed to equilibrate for at least 30 min prior to the addition to either a variable or constant concentrations of the sample for which the affinity is to be determined. After equilibration, the time-resolved fluorescent signal is quantitated using a fluorescent plate reader. The affinity of the test compound is estimated from a plot of fluorescence versus concentration of test compound added.

A basal level of FXR: peptide formation is observed in the absence of added ligand. Ligands that promote the complex formation induce a concentration-dependent increase in time-resolved fluorescent signal. Compounds which bind equally well to both monomeric FXR and to the FXR: peptide complex would be expected to give no change in signal, whereas ligands which bind preferentially to the monomeric receptor would be expected to induce a concentration-dependent decrease in the observed signal.

Methods & Materials

Advance Preparation: Human Farnasoid X Receptor alpha Ligand Binding Domain

Human FXRα Ligand Binding Domain (FXRα LBD) was expressed in *E.coli* strain BL21 (DE3) as an amino-terminal polyhistidine tagged fusion protein. Expression was under the control of an IPTG inducible T7 promoter. DNA encoding this recombinant protein was subcloned into the pRSET-A expression vector (Invitrogen). The coding sequence of Human FXRα LBD was derived from Genbank accession number U 68233 (amino acids 222 to 472).

Ten-liter fermentation batches were grown in Rich PO$_4$ media with 0.1 mg/mL Ampicillin at 25° C. for 12 hours, cooled to 9° C. and held at that temperature for 36 hours to a density of OD$_{600}$=14. At this cell density, 0.25 mM IPTG was added and induction proceeded for 24 hours at 9° C., to a final OD$_{600}$=16. Cells were harvested by centrifugation (20 minutes, 3500 g, 4° C.), and concentrated cell slurries were stored in PBS at −8° C.

Purification of Receptor Ligand Binding Domain

Routinely, 30-40 g cell paste (equivalent to 2-3 liters of the fermentation batch) was resuspended in 200-250 mL TBS, pH 7.2 (25mM Tris, 150 mM NaCl). Cells were lysed by passing 3 times through a French Press and cell debris was removed by centrifugation (30 minutes, 20,000 g, 4° C.). The cleared supernatant was filtered through course pre-filters, and TBS, pH 7.2, containing 500 mM imidazole was added to obtain a final imidazole concentration of 50 mM. This lysate was loaded onto a column (6×8 cm) packed with Sepharose [Ni$^{++}$ charged]Chelation resin (Pharmacia) and pre-equilibrated with TBS pH 7.21 50 mM imidazole. After washing to baseline absorbance with equilibration buffer, the column was washed with one column volume of TBS pH 7.2 containing 90 mM imidazole. FXRαLBD was eluted directly with 365 mM imidazole. Column fractions were pooled and dialyzed against TBS, pH 7.2, containing 0.5 mM EDTA and 5 mM DTT. The dialyzed protein sample was concentrated using Centri-prep 10 K (Amicon) and subjected to size exclusion, using a column (3×90 cm) packed with Sepharose S-75 resin (Pharmacia) pre-equilibrated with TBS, pH 7.2, containing 0.5 mM EDTA and 5 mM DTT.

Biotinylation of FXR

Purified FXRα LBD was desalted/buffer exchanged using PD-10 gel filtration columns into PBS [100 mM NaPhosphate, pH 7.2, 150 mM NaCl]. FXRα LBD was diluted to approximately 10 µM in PBS and five-fold molar excess of NHS-LC-Biotin (Pierce) was added in a minimal volume of PBS. This solution was incubated with gentle mixing for 30 minutes at room temperature. The biotinylation modification reaction was stopped by the addition of 2000× molar excess of Tris-HCl, pH 8. The modified FXRα LBD was dialyzed against 4 buffer changes, each of at least 50 volumes, PBS containing 5 mM DTT, 2 mM EDTA and 2% sucrose. The biotinylated FXRα LBD was subjected to mass spectrometric analysis to reveal the extent of modification by the biotinylation reagent In general, approximately 95% of the protein had at least a single site of biotinylation; and the overall extent of biotinylation followed a normal distribution of multiple sites, ranging from one to nine.

Preparation of Streptavidin-(Europium Chelate)-SRC1: Streptavdin-(APC)-FR Complex Biotinylated SRC-1(LCD2, 676-700) peptide and a ½ stoichiometric amount of streptavidin-conjugated europium chelate were incubated in assay buffer containing 10 mM DTT for at least 30 minutes. A second solution of stoichiometric amounts of biotinylated FXR and streptavidin-conjugated APC were incubated in assay buffer containing 10 mM DTT for at least 30 minutes. Each solution was then blocked with a 5 fold molar excess of biotin and allowed to equilibrate for at least 30 min. The labeled receptor and cofactor were mixed and again allowed to equilibrate for at least 30 min, then added in a one-step addition to the compound plate, utilizing e.g., a Titertek Multidrop 384.

Materials:

Assay Buffer: 50 mM Cl, 0.1 mg/mL BSA, 10 mM DTT, and 50 mM Tris (pH 8) The stock buffer is made by dissolving 2.853 g Tris base, 4.167 g Tris hydrochloride, 3.73 g KCl, and 0.1 g fatty acid free bovine serum albumin, in 1 L of deionized water. The pH is checked and adjusted to 8.0, if necessary, before adjusting to final volume. 0.154 g of solid DTT is added per 100 mL of buffer just before the start of an experiment.

BSA, fatty acid free
DTT
KCl
Europium labeled Streptavidin: (Wallac CR28-100)
Tris Hydrochloride
96 well plates: polypropylene for intermediate dilutions (Costar #3794) and either a clear-bottomed white SPA plates (Costar #3632) or a black Polyfiltronics plate (UP350 PSB) for assays.

Methods:

Experimental Details:

Each well to be assayed contained a previously prepared solution of FXR-APC and Europium labeled SRC1 and the desired concentration of test samples or controls (50 µL total volume). In general, the total volume was held constant by varying the concentration and volume of premixed receptors to compensate for any changes in the volume of a particular set of samples. The plates were incubated for at least 2 hours at room temperature and the fluorescent signal determined in a Wallac Victor Multilabel Fluorescence Reader.

Data Reduction:

For single concentration assays, the results of each test well were expressed as % of control, C, calculated according to eq. 1.

$$C = 100 * \frac{F_{sample} - F_{basal}}{F_{std} - F_{basal}} \quad (1)$$

where $F_{sample}$ is the signal observed in a particular sample well, $F_{total}$ is the signal observed in the presence of control inhibitor and $F_{basal}$ is the count rate observed in the presence of no ligand. The values used for $F_{std}$ and $F_{basal}$ were averages of the corresponding control wells included on every plate. The results are reported in Table 1 below. In Table 1, $+=5<pEC_{50}<5.99$; $++=6<pEC_{50}<6.99$ and $+++=7<pEC_{50}$.

TABLE 1

| Example | Activity (pEC$_{50}$) |
|---------|----------------------|
| 1 | +++ |
| 2 | +++ |
| 3 | ++ |
| 4 | ++ |
| 5 | +++ |
| 6 | ++ |
| 7 | ++ |
| 8 | ++ |
| 9 | ++ |
| 10 | ++ |
| 11 | +++ |
| 12 | +++ |
| 13 | ++ |
| 14 | ++ |
| 15 | ++ |
| 16 | ++ |
| 17 | ++ |
| 18 | +++ |
| 19 | +++ |
| 20 | +++ |
| 21 | +++ |
| 22 | ++ |
| 23 | ++ |
| 24 | ++ |
| 25 | ++ |
| 26 | + |
| 27 | ++ |
| 28 | ++ |
| 29 | ++ |
| 30 | ++ |
| 31 | ++ |
| 32 | ++ |
| 33 | ++ |
| 34 | ++ |
| 35 | ++ |
| 36 | ++ |
| 37 | ++ |
| 38 | ++ |
| 39 | ++ |
| 40 | + |
| 41 | ++ |
| 42 | ++ |
| 43 | + |
| 44 | ++ |
| 45 | + |
| 46 | ++ |
| 47 | +++ |
| 48 | +++ |
| 49 | ++ |
| 50 | +++ |
| 51 | ++ |
| 52 | ++ |
| 53 | ++ |
| 54 | +++ |
| 55 | + |
| 56 | + |
| 57 | ++ |
| 58 | ++ |
| 59 | ++ |
| 60 | + |
| 61 | + |
| 62 | +++ |
| 63 | ++ |
| 64 | ++ |
| 65 | +++ |
| 66 | ++ |
| 67 | ++ |
| 68 | + |
| 69 | ++ |
| 70 | ++ |
| 71 | ++ |
| 72 | ++ |
| 73 | ++ |

TABLE 1-continued

| Example | Activity (pEC$_{50}$) |
|---|---|
| 74 | ++ |
| 75 | ++ |
| 76 | ++ |
| 77 | +++ |
| 78 | +++ |
| 79 | +++ |
| 80 | +++ |
| 81 | +++ |
| 82 | ++ |
| 83 | ++ |
| 84 | + |
| 85 | ++ |
| 86 | ++ |
| 87 | ++ |
| 88 | ++ |
| 89 | ++ |
| 90 | ++ |
| 91 | ++ |
| 92 | ++ |
| 93 | ++ |
| 94 | ++ |
| 95 | ++ |
| 96 | ++ |
| 97 | ++ |
| 98 | + |
| 99 | + |
| 100 | ++ |
| 101 | ++ |
| 102 | ++ |
| 103 | ++ | wherein:

a is 1-5;

each $R^1$ is the same or different and is independently selected from the group consisting of halo, alkyl, alkenyl, —OR$^6$, —S(O)$_f$R$^6$, —NR$^6$R$^7$, —R$^4$OR$^6$, —R$^4$S(O)$_f$R$^6$, —R$^4$NR$^6$R$^7$ and cyano;

b is 0-3;

$R^2$ is selected from the group consisting of alkyl, alkenyl, C$_{3-6}$cycloalkyl, C$_{3-6}$cycloalkenyl, —OR$^6$, —NR$^6$R$^7$, —R$^4$OR$^6$, —R$^4$NR$^6$R$^7$, cyano and nitro;

Y is —O— or —N(R$^8$)—;

c is 0-4;

each $R^3$ is the same or different and is independently selected from the group consisting of halo, alkyl, alkenyl, alkynyl, cycloalkyl, cycloalkenyl, —OR$^6$, —COR$^6$, —CO$_2$R$^6$, —CH(R$^6$)OR$^7$, —S(O)$_f$R$^6$, —NR$^6$R$^7$, —R$^4$cycloalkyl, —R$^4$OR$^6$, —R$^4$COR$^6$, —R$^4$CO$_2$R$^6$, —R$^4$S(O)$_f$R$^6$, —R$^4$NR$^6$R$^7$ and cyano;

Z is selected from the group consisting of —O—R$^4$—, —S(O)$_f$—R$^4$—, —N(R$^8$)—R$^4$—, —R$^4$—N(R$^8$)—, —C(O)R$^4$N(R$^8$)—, —S(O)$_f$N(R$^8$)— and —S(O)$_f$R$^4$N(R$^8$)—;

each $R^4$ is the same or different and is independently selected from the group consisting of alkylene and alkenylene;

What is claimed is:

1. A compound of formula (I):

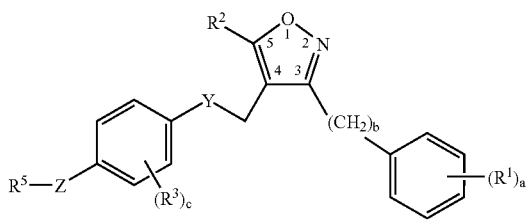

I

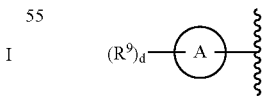

wherein Ring A is aryl or a 5-12 membered heterocycle or heteroaryl;

d is 0-4;

each $R^9$ is the same or different and is independently selected from the group consisting of halo, alkyl, alkenyl, alkynyl, cycloalkyl, —OR$^6$, —COR$^6$, —CO$_2$R$^6$, —CH(R$^6$)OR$^7$, —S(O)$_f$R$^6$, —NR$^6$R$^7$, —R$^4$cycloalkyl, —R$^4$OR$^6$, —R$^4$COR$^6$, $R^5$ is selected from the group consisting of R$^6$O—, R$^6$O$_2$C—, and —$R^4CO_2R^6$, —$R^4S(O)_fR^6$, —$R^4NR^6R^7$, cyano, 5-9 membered heterocycle and 5-9 membered heteroaryl;

each $R^6$ and $R^7$ are the same or different and are each independently selected from the group consisting of H, alkyl, alkenyl, $C_{3-6}$cycloalkyl and $C_{3-6}$cycolalkenyl;

$R^8$ is H or alkyl; and each f is the same or different and is independently selected from the group consisting of 0, 1 and 2;

or a pharmaceutically acceptable salt or solvate thereof.

2. The compound according to claim 1 wherein a is 1-2.

3. The compound according to claim 1 wherein each $R^1$ is the same or different and is independently selected from the group consisting of halo and —$OR^6$.

4. The compound according to claim 1 wherein b is 0 or 1.

5. The compound according to claim 1 wherein $R^2$ is selected from the group consisting of alkyl and $C_{3-6}$cycloalkyl.

6. The compound according to claim 1 wherein Y is —O—.

7. The compound according claim 1 wherein c is 0-2.

8. The compound according to claim 1 wherein each $R^3$ is the same or different and is independently selected from the group consisting of halo and alkyl.

9. The compound according to claim 1 wherein $R^8$ is H or methyl.

10. The compound according to claim 1 wherein $R^5$ is selected from the group consisting of $R^6O_2C$—, and

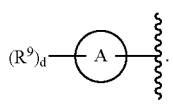

11. The compound according to claim 1 wherein $R^5$ is and Ring A is phenyl or furan.

12. A pharmaceutical composition comprising a compound according to claim 1 and a pharmaceutically acceptable carrier or diluent.

13. A method for the treatment of cardiovascular disease in a subject, said method comprising administering to said subject a therapeutically effective amount of a compound according to claim 1.

14. A method for the treatment of cholestatic liver disease in a subject comprising administering a therapeutically effective amount of a compound according to claim 1.

15. A method for the treatment of organ fibrosis in a subject comprising administering a therapeutically effective amount of a compound according to claim 1.

16. A method for increasing HDL cholesterol in a subject, said method comprising administering a therapeutically effective amount of a compound according to claim 1.

17. A method for lowering triglycerides in a subject, said method comprising administering a therapeutically effective amount of a compound according to claim 1.

18. A process for preparing a compound according to claim 1, said process comprising the steps of:
a) reducing a compound of formula (X):

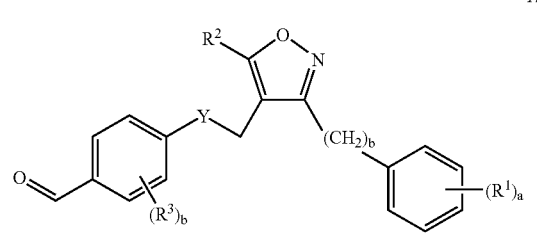

followed by chorination to prepare a compound of formula (XI):

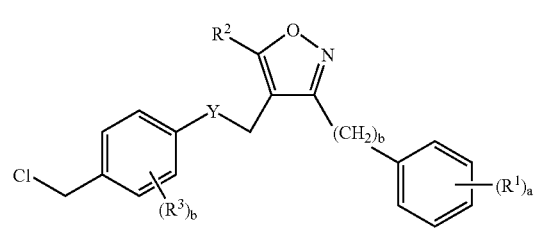

and
b) reacting the compound of formula (XI) with a compound of formula (XII):

$R^5$-$Z^1$     XII wherein $Z^1$ is —O—, —$S(O)_f$— or —$N(R^8)$—;
to prepare a compound of formula (I-A):

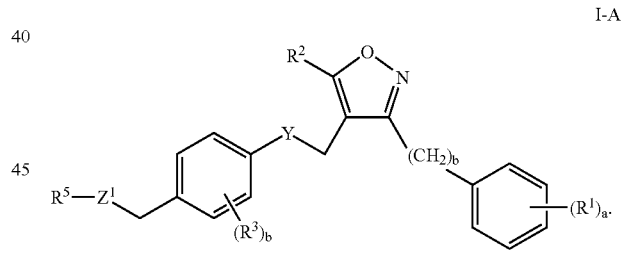

19. A process for preparing a compound according to claim 1, said process comprising the steps of:
a) rearranging the carbonyl functionality of the compound of formula (X):

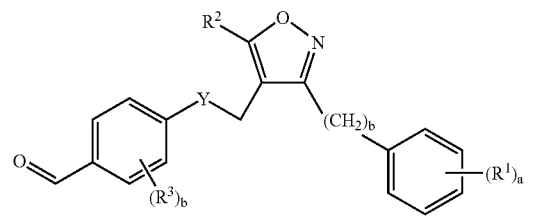

followed by hydrolysis to prepare a compound of formula (XIII):

XIII

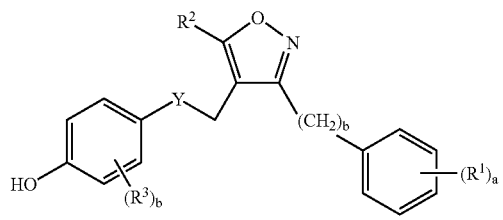

and b) reacting the compound of formula (XIII) with a suitable electrophile to prepare a compound of formula (I-B):

I-B

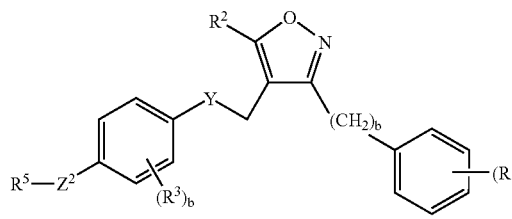

wherein $Z^2$ is —$R^4$—O—.

20. A process for preparing a compound according to claim 1, said process comprising the steps of:
a) reacting a protected compound of formula (XV):

XV

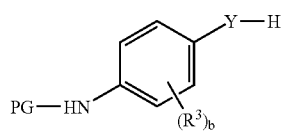

wherein PG is a protecting group;
with a compound of formula (VI):

VI

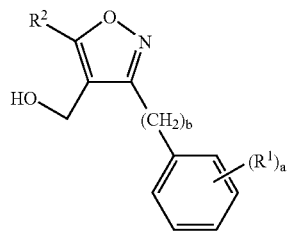

to prepare a compound of formula (XVI):

XVI

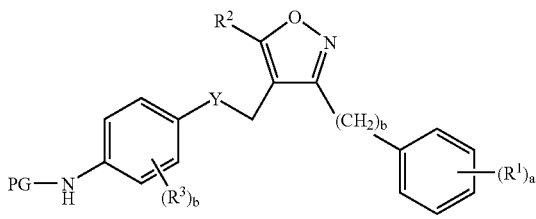

b) optionally alkylating the compound of formula (XVI), followed by deprotecting the compound of formula (XVI) to prepare a compound of formula (XVII):

XVII

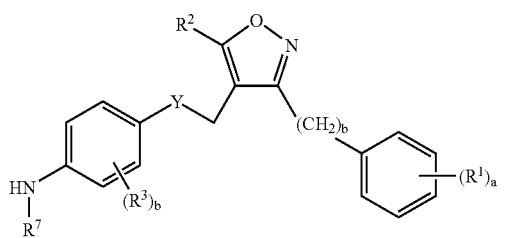

and c) reacting the compound of formula (XVII) with a suitable electrophile to prepare a compound of formula (I-C):

I-C

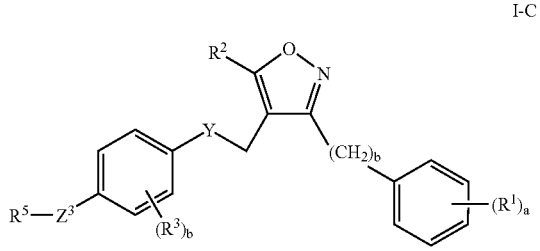

wherein $Z^3$ is selected from the group consisting of —$R^4$—O—, —$R^4$—S(O)$_f$—, —$R^4$—N($R^8$)—, —CON($R^8$)—, —C(O)$R^4$N($R^8$)—, —S(O)$_f$N($R^8$)— and —S(O)$_f R^4$N($R^8$)—.

21. A compound selected from:
3-{[(4-{3-(2,6-Dichlorophenyl)-5-isopropylisoxazol-4-yl]methoxy}-2-methylphenyl)-(methyl)amino]methyl}benzoic acid;

Methyl 4-[(4-{[3-(2,6-dichlorophenyl)-5-isopropyl-4-isoxazolyl]methoxy}-2-dimethylanilino)methyl]benzoate;

3-{[(2-Chloro-4-{[3-(2,6-dichlorophenyl)-5-isopropyl-isoxazol-4-yl]methoxy}-phenyl)amino]methyl}benzoic acid;

5-[(4-{[3-(2,6-Dichlorophenyl)-5-isopropyl-4-isoxazolyl]methoxy}-2-dimethyl-anilino)methyl]-2-furoic acid;

4-[(4-{[3-(2,6-Dichlorophenyl)-5-isopropyl-4-isoxazolyl]methoxy}-2-dimethyl-anilino)methyl]benzoic acid;

Methyl 2-[(4-{[3-(2,6-dichlorophenyl)-5-isopropyl-4-isoxazolyl]methoxy}-2-dimethylanilino)methyl]-3-furoate;

N-(2,1,3-Benzoxadiazol-5-ylmethyl)-4-{[3-(2,6-dichlorophenyl)-5-isopropyl-4-isoxazolyl]methoxy}-N,2-dimethylaniline;

N-(4-{[3-(2,6-Dichlorophenyl)-5-isopropyl-4-isoxazolyl]methoxy}-2-methylphenyl)-N-methyl-N-[4-(1, 2,3-thiadiazol-4-yl)benzyl]amine;

4-[(4-{[3-(2,6-Dichlorophenyl)-5-isopropyl-4-isoxazolyl]methoxy}-2-dimethyl-anilino)methyl]benzonitrile;

2-[(4-{[3-(2,6-Dichlorophenyl)-5-isopropyl-4-isoxazolyl]methoxy}-2-dimethyl-anilino)methyl]-3-furoic acid;

{3-[(4-{[3-(2,6-Dichlorophenyl)-5-isopropyl4-isoxazolyl]methoxy}-2-dimethylanilino)methyl]phenyl}methanol;

{4-[(4-{[3-(2,6-Dichlorophenyl)-5-isopropyl4-isoxazolyl]methoxy}-2-dimethylanilino)methyl]phenyl}methanol;

3-[(4-{[3-(2, 6-Dichlorobenzyl)-5-ethyl4-isoxazolyl]methoxy}-2-dimethylanilino)methyl]benzoic acid;

3-({[4-{[5-Isopropyl-3-(2,4,6-trichlorophenyl)isoxazol-4-yl]methoxy}-2-methylphenyl)-(methyl)amino]methyl}benzoic acid;

3-[(4-{[3-(2, 6-Dichlorobenzyl)-5-isopropyl-4-isoxazolyl]methoxy}-2-dimethylanilino)methyl]benzoic acid;

3-{[(4-{[3-(2-Chlorobenzyl)-5-isopropylisoxazol-4-yl]methoxy}-2-methylphenyl)-(methyl)-amino]methyl}benzoic acid;

3-[(4-([5-Cyclopropyl-3-(2,6-dichlorobenzyl)-4-isoxazolyl]methoxy}-2-dimethylanilino)methyl]benzoic acid;

5-{[4-({5-Isopropyl-3-[2-(trifluoromethoxy)phenyl]-4-isoxazolyl}methoxy)-2-dimethylanilino]methyl}-2-furoic acid;

14-{[4-({5-Isopropyl-3-[2-(trifluoromethoxy)phenyl]-4-isoxazolyl}methoxy)-2-dimethylanilino]methyl}benzoic acid;

3-{[4-({5-Isopropyl-3-[2-(trifluoromethoxy)phenyl]-4-isoxazolyl}methoxy)-2-dimethylanilino]methyl}benzoic acid;

Methyl 5-{[4-({5-isopropyl-3-[2-(trifluoromethoxy)phenyl]-4-isoxazolyl}methoxy)-2-dimethylanilino]methyl}-2-furoate;

Methyl 4-{[4-({5-isopropyl-3-[2-(trifluoromethoxy)phenyl]-4-isoxazolyl4methoxy)-2-dimethylanilino]methyl}benzoate;

4-{[(2-Chloro-4-{[3-(2,6-dichlorophenyl)-5-isopropyl-isoxazol-4-yl]methoxy}phenyl)-amino]carbonyl}benzoic acid;

Methyl 3-[(2-chloro-4-{[3-(2,6-dichlorophenyl)-5-isopropyl-4-isoxazolyl]methoxy}-anilino)carbonyl]benzoate;

Methyl 4-[(2-chloro-4-{[3-(2,6-dichlorophenyl)-5-isopropyl-4-isoxazolyl]methoxy}-anilino)carbonyl]benzoate;

3-[(4-{[3-(2,6-Dichlorophenyl)-5-isopropyl-4-isoxazolyl]methoxy}-2-methylanilino)-carbonyl]benzoic acid;

4-[(4-{[3-(2,6-Dichlorophenyl)-5-isopropyl-4-isoxazolyl]methoxy}-2-methylanilino)-carbonyl]benzoic acid;

3-[(2-Chloro-4-{[3-(2,6-dichlorophenyl)-5-isopropyl-4-isoxazolyl]methoxy}-anilino)carbonyl]benzoic acid;

3-[(4-{[3-(2,6-Dichlorophenyl)-5-isopropyl-4-isoxazolyl]methoxy}-2-dimethylanilino)carbonyl]benzoic acid;

3-[(2-Chloro-4-{[3-(2, 6-dichlorophenyl)-5-isopropyl-4-isoxazolyl]methoxy}-methylanilino)carbonyl]benzoic acid;

4-[(2-Chloro-4-{[3-(2,6-dichlorophenyl)-5-isopropyl-4-isoxazolyl]methoxy}-methylanilino)carbonyl]benzoic acid;

3-{[4-({5-Isopropyl-3-[2-(trifluoromethoxy)phenyl]-4-isoxazolyl}methoxy)-2-dimethylanilino]carbonyl}benzoic acid;

3-{[4-({5-Isopropyl-3-[2-(trifluoromethoxy)phenyl]-4-isoxazolyl}methoxy)-2-methylanilino]carbonyl}benzoic acid;

3-{[2-Chloro-4-({5-isopropyl-3-[2-(trifluoromethoxy)phenyl]-4-isoxazolyl}-methoxy)methylanilino]carbonyl}benzoic acid;

Methyl 3-{[(4-{[3-(2,6-dichlorophenyl)-5-isopropylisoxazol-4-yl]methoxy}-2-methylphenyl)(methyl)amino]sulfonyl}benzoate;

Methyl 3-{[(2-chloro-4-{[3-(2, 6-dichlorophenyl)-5-isopropylisoxazol-4-yl]methoxy}-phenyl)amino]sulfonyl}benzoate;

Methyl 3-{[(4-{[3-(2,6-dichlorophenyl)-5-isopropylisoxazol-4-yl]methoxy}-2-methylphenyl)amino]sulfonyl}benzoate;

Methyl 3-{[(4-{[3-(2,6-dichlorophenyl)-5-isopropylisoxazol-4-yl]methoxy}phenyl)-amino]-sulfonyl}benzoate;

3-{[(4-{[3-(2,6-Dichlorophenyl)-5-isopropylisoxazol-4-yl]methoxy}-2-methylphenyl)-amino]sulfonyl}benzoic acid;

3-{[(4-{[3-(2,6-Dichlorophenyl)-5-isopropylisoxazol-4-yl]methoxyphenyl)amino]-sulfonyl}benzoic acid;

Methyl 3-{[(2-chloro-4-{[3-(2,6-dichlorophenyl)-5-isopropylisoxazol-4-yl]methoxy}-phenyl)(methyl)amino]sulfonyl}benzoate;

Methyl 3-{[(4-{([3-(2,6-dichlorophenyl)-5-isopropyl-isoxazol-4-yl]methoxy}phenyl)-(methyl)amino]sulfonyl}benzoate;

Methyl 3-{[(2-chloro-4-{([3-(2,6-dichlorophenyl)-5-isopropylisoxazol-4-yl]methoxy}-phenyl)(ethyl)amino]sulfonyl}benzoate;

Methyl 3-{[(4-{[3-(2,6-dichlorophenyl)-5-isopropylisoxazol-4-yl]methoxy}-2-methyl-phenyl)(ethyl)amino]sulfonyl}benzoate;

Methyl 3-{[(4-{[3-(2,6-dichlorophenyl)-5-isopropylisoxazol-4-yl]methoxy}phenyl)-(ethyl)-amino]sulfonyl}benzoate;

3-{[(2-Chloro-4-{[3-(2,6-dichlorophenyl)-5-isopropyl-isoxazol-4-yl]methoxy}phenyl)-amino]sulfonyl}benzoic acid;

3-{[(2-Chloro-4-{[3-(2,6-dichlorophenyl)-5-isopropylisoxazol-4-yl]methoxy}phenyl)-(methyl)amino]sulfonyl}benzoic acid;

3-{[(4-{[3-(2, 6-Dichlorophenyl)-5-isopropylisoxazol-4-yl]methoxy}-2-methylphenyl)-(methyl)amino]sulfonyl}benzoic acid;

3-{[(4-{[3-(2,6-Dichlorophenyl)-5-isopropylisoxazol-4-yl]methoxy}phenyl)(methyl)-amino]sulfonyl]benzoic acid;

3-{[(2-Chloro-4-{[3-(2,6-dichlorophenyl)-5-isopropyl-isoxazol-4-yl]methoxy}phenyl)-(ethyl)amino]sulfonyl}benzoic acid;

3-{[(4-{[3-(2,6-Dichlorophenyl)-5-isopropylisoxazol-4-yl]methoxy}-2-methylphenyl)-(ethyl)amino]sulfonyl}benzoic acid;

3-{[(4-{[3-(2,6-Dichlorophenyl)-5-isopropylisoxazol-4-yl]methoxy}phenyl)(ethyl)-aminosulfonyl}benzoic acid;

Methyl 4-{[(2-chloro-4-{([3-(2,6-dichlorophenyl)-5-isopropylisoxazol-4-yl]methoxy}-phenyl)amino]sulfonyl}benzoate;

Methyl 4-{[(4-{[3-(2,6-dichlorophenyl)-5-isopropylisoxazol-4-yl]methoxy}-2-methyl-phenyl)amino]sulfonyl}benzoate;

Methyl 4-{[(4-{[3-(2,6-dichlorophenyl)-5-isopropylisoxazol-4-yl]methoxy}phenyl)-amino]sulfonyl}benzoate;

4-{[(2-Chloro-4-{[3-(2,6-dichlorophenyl)-5-isopropyl-isoxazol-4-yl]methoxy}phenyl)-amino]sulfonyl}benzoic acid;

4-{[(4-{[3-(2,6-Dichlorophenyl)-5-isopropylisoxazol-4-yl]methoxy}-2-methylphenyl)-amino]sulfonyl}benzoic acid;

4-{[(4-{[3-(2,6-Dichlorophenyl)-5-isopropylisoxazol-4-yl]methoxy}phenyl)amino]-sulfonyl}benzoic acid;

Methyl 4-{[(4-{[3-(2,6-dichlorophenyl)-5-isopropylisoxazol-4-yl]methoxy}-2-methyl-phenyl)(methyl)amino]sulfonyl}benzoate;

Methyl 4-{[(4-{[3-(2,6-dichlorophenyl)-5-isopropylisoxazol-4-yl]methoxy}phenyl)-(methyl)amino]sulfonyl}benzoate;

Methyl 4-{[(4-{[3-(2,6-dichlorophenyl)-5-isopropylisoxazol-4-yl]methoxy}phenyl)-(ethyl)amino]sulfonyl}benzoate;

4-{[(2-Chloro-4-{[3-(2,6-dichlorophenyl)-5-isopropyl-isoxazol-4-yl]methoxy}phenyl)-(methyl)amino]sulfonyl}benzoic acid;

4-{[(4-{[3-(2,6-Dichlorophenyl)-5-isopropylisoxazol-4-yl]methoxy}-2-methylphenyl)-(methyl)amino]sulfonyl}benzoic acid;

4-{[(4-{[3-(2,6-Dichlorophenyl)-5-isopropylisoxazol-4-yl]methoxy}phenyl)(methyl)-amino]sulfonyl}benzoic acid;

4-{[(2-Chloro-4-{[3-(2,6-dichlorophenyl)-5-isopropyl-isoxazol-4-yl]methoxy}phenyl)-(ethyl)amino]sulfonyl}benzoic acid;

4-{[(4-{[3-(2,6-Dichlorophenyl)-5-isopropylisoxazol-4-yl]methoxy}-2-methylphenyl)-(ethyl)amino]sulfonyl}benzoic acid;

4-{[(4-{[3-(2,6-Dichlorophenyl)-5-isopropylisoxazol-4-yl]methoxy}phenyl)(ethyl)amino]-sulfonyl}benzoic acid;

3-({[2-Chloro-4-({5-isopropyl-3-[2-(trifluoromethoxy)phenyl]isoxazol-4-yl}methoxy)-phenyl]amino}sulfonyl)benzoic acid;

3-({[4-({5-Isopropyl-3-[2-(trifluoromethoxy)phenyl]isoxazol-4-yl}methoxy)-2-methyl-phenyl]amino}sulfonyl)benzoic acid;

Methyl 3-{[[2-chloro-4-({5-isopropyl-3-[2-(trifluoromethoxy)phenyl]-isoxazol-4-yl}methoxy)phenyl](methyl)amino]sulfonyl}benzoate;

Methyl 3-{[[4-({5-isopropyl-3-[2-(trifluoromethoxy)phenyl]isoxazol-4-yl}methoxy)-2-methylphenyl](methyl)amino]sulfonyl}benzoate;

3-({[[2-Chloro-4-({5-isopropyl-3-[2-(trifluoromethoxy)phenyl]isoxazol-4-yl}methoxy)-phenyl](methyl)amino]sulfonyl}benzoic acid;

3-{[[4-({5-Isopropyl-3-[2-(trifluoromethoxy)phenyl]isoxazol-4-yl}methoxy)-2-methyl-phenyl](methyl)amino]sulfonyl}benzoic acid;

3-{[(4-{[3-(2,6-Dichlorobenzyl)-5-ethylisoxazol-4-yl]methoxy}-2-methylphenyl)(methyl)-amino]sulfonyl}benzoic acid;

Methyl 4-[(2-chloro-4-[3-(2,6-dichlorophenyl)-5-isopropylisoxazol-4-yl]methoxy)-benzyl)oxy]benzoate;

Methyl 3-[(2-chloro-4-{[3-(2,6-dichlorophenyl)-5-isopropylisoxazol-4-yl]methoxy}-benzyl)-oxy]benzoate;

3-[(2-Chloro-4-{[3-(2,6-dichlorophenyl)-5-isopropyl-isoxazol-4-yl]methoxy}-benzyl)oxy]-benzoic acid;

3-[(2-Chloro-4-{[3-(2,6-dichlorophenyl)-5-isopropyl-isoxazol-4-yl]methoxy}-benzyl)thio]-benzoic acid;

3-[(4-{[3-(2,6-Dichlorophenyl)-5-isopropylisoxazol-4-yl]methoxy}-2-methylbenzyl)-oxy]-benzoic acid;

3-[(4-{[3-(2,6-Dichlorophenyl)-5-isopropylisoxazol-4-yl]methoxy}-2-methylbenzyl)-thio]-benzoic acid;

4-[(2-Chloro-4-{[3-(2,6-dichlorophenyl)-5-isopropyl-isoxazol-4-yl]methoxy}benzyl)-oxy]benzoic acid;

4-[(2-Chloro-4-{[3-(2,6-dichlorophenyl)-5-isopropyl-isoxazol-4-yl]methoxy}benzyl)-thio]-benzoic acid;

Methyl 3-{[2-chloro-4-({5-isopropyl-3-[2-(trifluoromethoxy)-phenyl]isoxazol-4-yl}methoxy) benzyl]oxy}benzoate;

Methyl 3-{[4-({5-isopropyl-3-[2-(trifluoromethoxy)phenyl]isoxazol-4-yl}methoxy)-2-methylbenzyl]oxy}benzoate;

3-{[2-Chloro-4-({5-isopropyl-3-[2-(trifluoromethoxy)phenyl]isoxazol-4-yl}methoxy)-benzyl]oxy}benzoic acid;

3-{[4-({5-Isopropyl-3-[2-(trifluoromethoxy)phenyl]isoxazol-4-yl}methoxy)-2-methyl-benzyl]oxy}benzoic acid;

3-[(2-Chloro-4-{([3-(2,6-dichlorobenzyl)-5-ethylisoxazol-4-yl]methoxy}benzyl)oxy]-benzoic acid;

Methyl 3-{[2-chloro-4-({5-isopropyl-3-[2-(trifluoromethoxy)phenyl]isoxazol-4-yl}methoxy) benzyl]thio}benzoate;

Methyl 3-{[4-({5-isopropyl-3-[2-(trifluoromethoxy)phenyl]isoxazol-4-yl}methoxy)-2-methylbenzyl]thio}benzoate;

3-{[2-Chloro-4-({5-isopropyl-3-[2-(trifluoromethoxy)phenyl]isoxazol-4-yl}methoxy)-benzyl]thio}benzoic acid;

3-{[4-({5-Isopropyl-3-[2-(trifluoromethoxy)phenyl]isoxazol-4-yl}methoxy)-2-methyl-benzyl]thio}benzoic acid;

Methyl 3-[(2-chloro-4-{[3-(2,6-dichlorophenyl)-5-isopropylisoxazol-4-yl]methoxy}benzyl)(methyl)amino]benzoate;

3-[(2-Chloro-4-{[3-(2,6-dichlorophenyl)-5-isopropyl-isoxazol-4-yl]methoxy}benzyl)-(methyl)amino]benzoic acid;

3-[(2-Chloro-4-{[3-(2,6-dichlorophenyl)-5-isopropyl-isoxazol-4-yl]methoxy}benzyl)-amino]benzoic acid;

Ethyl 3-{[2-chloro-4-({5-isopropyl-3-[2-(trifluoromethoxy)phenyl]-4-isoxazolyl}-methoxy)benzyl]amino}benzoate;

3-{[2-Chloro-4-({5-isopropyl-3-[2-(trifluoromethoxy)phenyl]-4-isoxazolyl}methoxy)-benzyl]amino}benzoic acid;

3-[[2-Chloro-4-({5-isopropyl-3-[2-(trifluoromethoxy)phenyl]-4-isoxazolyl}methoxy)-benzyl](methyl)amino]benzoic acid;

Methyl 4-[(4-{[3-(2,6-dichlorophenyl)-5-isopropylisoxazol-4-yl]methoxy}-2-methylphenoxy)methyl]benzoate;

Methyl 3-[(2-chloro-4-{[3-(2,6-dichlorophenyl)-5-isopropylisoxazol-4-yl]methoxy}-phenoxy)methyl]benzoate;

Methyl 3-[(4-{([3-(2,6-dichlorophenyl)-5-isopropylisoxazol-4-yl]methoxy}-2-methyl-phenoxy)methyl]benzoate;

3-[(2-Chloro-4-{[3-(2,6-dichlorophenyl)-5-isopropyl-isoxazol-4-yl]methoxy}phenoxy)-methyl]benzoic acid;

3-[(4-{[3-(2,6-Dichlorophenyl)-5-isopropylisoxazol-4-yl]methoxy}-2-methylphenoxy)-methyl]benzoic acid; and Methyl 4-[(4-{[3-(2,6-dichlorophenyl)-5-isopropylisoxazol-4-yl]methoxy}-2-methyl-phenoxy)methyl]benzoate, and pharmaceutically acceptable salts and solvates thereof.

22. A compound of formula (I):

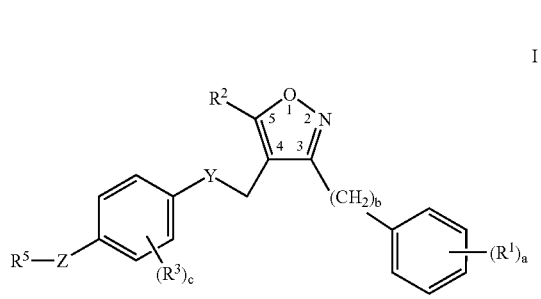

I wherein:
a is 1-5;
each $R^1$ is the same or different and is independently selected from the group consisting of halo, alkyl, alkenyl, —$OR^6$, —$S(O)_fR^6$, —$NR^6R^7$, —$R^4OR^6$, —$R^4S(O)_fR^6$, —$R^4NR^6R^7$ and cyano;
b is 0-3;
$R^2$ is selected from the group consisting of alkyl, alkenyl, $C_{3-6}$cycloalkyl, $C_{3-6}$cycloalkenyl, —$OR^6$, —$NR^6R^7$, —$R^4OR^6$, —$R^4NR^6R^7$, cyano and nitro;
Y is —O— or —$N(R^8)$—;
c is 0-4;
each $R^3$ is the same or different and is independently selected from the group consisting of halo, alkyl, alkenyl, alkynyl, cycloalkyl, cycloalkenyl, —$OR^6$, —$COR^6$, —$CO_2R^6$, —$CH(R^6)OR^7$, —$S(O)_fR^6$, —$NR^6R^7$, —$R^4$cycloalkyl, —$R^4OR^6$, —$R^4COR^6$, —$R^4CO_2R^6$, —$R^4S(O)_fR^6$, —$R^4NR^6R^7$ and cyano;
Z is —C(O)N($R^8$)—;
each $R^4$ is the same or different and is independently selected from the group consisting of alkylene and alkenylene;
$R^5$ is selected from the group consisting of $R^6O_2C$— and

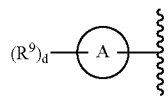

wherein Ring A is aryl or a 5-12 membered heterocycle or heteroaryl;
d is 0-4;
each $R^9$ is the same or different and is independently selected from the group consisting of halo, alkyl, alkenyl, alkynyl, cycloalkyl, —$OR^6$, —$COR^6$, —$CO_2R^6$, —$CH(R^6)OR^7$, —$S(O)_fR^6$, —$NR^6R^7$, —$R^4$cycloalkyl, —$R^4OR^6$, —$R^4COR^6$, —$R^4CO_2R^6$, —$R^4S(O)_fR^6$, —$R^4NR^6R^7$, cyano, 5-9 membered heterocycle and 5-9 membered heteroaryl;
each $R^6$ and $R^7$ are the same or different and are each independently selected from the group consisting of H, alkyl, alkenyl, $C_{3-6}$cycloalkyl and $C_{3-6}$cycolalkenyl;

$R^8$ is H or alkyl; and
each f is the same or different and is independently selected from the group consisting of 0, 1 and 2;
or a pharmaceutically acceptable salt or solvate thereof.

23. A compound of formula (I):

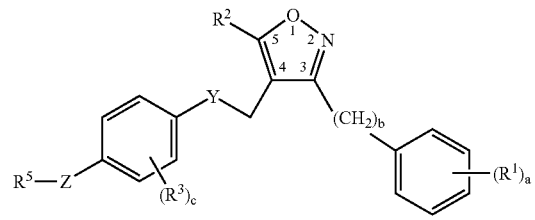

I wherein:
a is 1-5;
each $R^1$ is the same or different and is independently selected from the group consisting of halo, alkyl, alkenyl, —$OR^6$, —$S(O)_fR^6$, —$NR^6R^7$, —$R^4OR^6$, —$R^4S(O)_fR^6$, —$R^4NR^6R^7$ and cyano;
b is 0-3;
$R^2$ is selected from the group consisting of alkyl, alkenyl, $C_{3-6}$cycloalkyl, $C_{3-6}$cycloalkenyl, —$OR^6$, —$NR^6R^7$, —$R^4OR^6$, —$R^4NR^6R^7$, cyano and nitro;
Y is —O— or —$N(R^8)$—;
c is 0-4;
each $R^3$ is the same or different and is independently selected from the group consisting of halo, alkyl, alkenyl, alkynyl, cycloalkyl, cycloalkenyl, —$OR^6$, —$COR^6$, —$CO_2R^6$, —$CH(R^6)OR^7$, —$S(O)_fR^6$, —$NR^6R^7$, —$R^4$cycloalkyl, —$R^4OR^6$, —$R^4COR^6$, —$R^4CO_2R^6$, —$R^4S(O)_fR^6$, —$R^4NR^6R^7$ and cyano;
Z is —$R^4$—O—;
each $R^4$ is the same or different and is independently selected from the group consisting of alkylene and alkenylene;
$R^5$ is

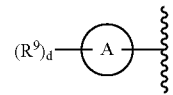

wherein Ring A is aryl or a 5-12 membered heterocycle or heteroaryl;
d is 0-4;
each $R^9$ is the same or different and is independently selected from the group consisting of halo, alkyl, alkenyl, alkynyl, cycloalkyl, —$OR^6$, —$COR^6$, —$CO_2R^6$, —$CH(R^6)OR^7$, —$S(O)_fR^6$, —$NR^6R^7$, —$R^4$cycloalkyl, —$R^4OR^6$, —$R^4COR^6$, —$R^4CO_2R^6$, —$R^4S(O)_fR^6$, —$R^4NR^6R^7$, cyano, 5-9 membered heterocycle and 5-9 membered heteroaryl;
each $R^6$ and $R^7$ are the same or different and are each independently selected from the group consisting of H, alkyl, alkenyl, $C_{3-6}$cycloalkyl and $C_{3-6}$cycolalkenyl;
$R^8$ is H or alkyl; and
each f is the same or different and is independently selected from the group consisting of 0, 1 and 2;
or a pharmaceutically acceptable salt or solvate thereof.

* * * * *

UNITED STATES PATENT AND TRADEMARK OFFICE
CERTIFICATE OF CORRECTION

| | | |
|---|---|---|
| PATENT NO. | : 7,319,109 B2 | Page 1 of 2 |
| APPLICATION NO. | : 10/535228 | |
| DATED | : January 15, 2008 | |
| INVENTOR(S) | : Boggs et al. | |

It is certified that error appears in the above-identified patent and that said Letters Patent is hereby corrected as shown below:

On Cover Page, - Foreign Patent Documents Reads:
-- GB 2293360 A 3/1996 --

Should read:
-- GB2293380 A 3/1996 --

Claim 21, Column 89, line 7
Should read:
-- {3-[(4-{[3-(2,6-Dichlorophenyl)-5-isopropyl-4-isox- --

Claim 21, Column 89, line 10
Should read:
-- {4-[(4-{[3-(2,6-Dichlorophenyl)-5-isopropyl-4-isox- --

Claim 21, Column 89, line 13
Should read:
-- 3-[(4-{[3-(2,6-Dichlorobenzyl)-5-ethyl-4-isoxazolyl] --

Claim 21, Column 89, line 30
Should read:
-- 4-{[4-{5-Isopropyl-3-[2-(trifluoromethoxy)phenyl]-4- --

Claim 21, Column 89, line 40
Should read:
-- nyl]-4-isoxazolyl[methoxyl)-2-dimethylanilino] --

Claim 21, Column 90, line 27
Should read:
-- yl]methoxy}phenyl)amino]-sulfonyl}benzoic acid; --

Claim 21, Column 90, line 34
Should read:
-- Methyl 3-{[2-chloro-4-{[3-(2,6-dichlorophenyl)-5-iso- --

UNITED STATES PATENT AND TRADEMARK OFFICE
CERTIFICATE OF CORRECTION

PATENT NO. : 7,319,109 B2
APPLICATION NO. : 10/535228
DATED : January 15, 2008
INVENTOR(S) : Boggs et al.

It is certified that error appears in the above-identified patent and that said Letters Patent is hereby corrected as shown below:

Claim 21, Column 90, line 65
Should read:
-- Methyl 4-{[(2-chloro-4-{[3-(2,6-dichlorophenyl)-5-iso- --

Claim 21, Column 91, line 62
Should read:
-- Methyl 4-[2(2-chloro-4-{[3-(2,6-dichlorophenyl)-5-isopro- --

Claim 21, Column 92, line 24
Should read:
-- 3-[(2-Chloro-4-{[3-(2,6-dichlorobenzyl)-5-ethylisox- --

Signed and Sealed this

Third Day of November, 2009

David J. Kappos
*Director of the United States Patent and Trademark Office*

SEQUENCE LISTING

<160> NUMBER OF SEQ ID NOS: 1

<210> SEQ ID NO 1
<211> LENGTH: 25
<212> TYPE: PRT
<213> ORGANISM: homo sapien
<220> FEATURE:

<400> SEQUENCE: 1

Cys Pro Ser Ser His Ser Ser Leu Thr Glu Arg His Lys Ile Leu His
1               5                   10                  15

Arg Leu Leu Gln Glu Gly Ser Pro Ser
            20                  25